(12) United States Patent
Düx et al.

(10) Patent No.: US 9,040,732 B2
(45) Date of Patent: May 26, 2015

(54) PROCESS FOR PREPARING DIARYL CARBONATES FROM DIALKYL CARBONATES

(75) Inventors: Andre Düx, Brühl (DE); Guenter Olf, Leverkusen (DE); Kaspar Hallenberger, Leverkusen (DE); Georg Ronge, Düsseldorf (DE); Ricarda Leiberich, Neu-Isenburg (DE); Johan Vanden Eynde, Zwijnaarde (BE); Wim Wuytack, Zele (BE); Pieter Ooms, Krefeld (DE); Johann Rechner, Kempen (DE)

(73) Assignee: Bayer MaterialScience AG (DE)

( * ) Notice: Subject to any disclaimer, the term of this patent is extended or adjusted under 35 U.S.C. 154(b) by 922 days.

(21) Appl. No.: 12/483,669

(22) Filed: Jun. 12, 2009

(65) Prior Publication Data

US 2010/0010252 A1    Jan. 14, 2010

(30) Foreign Application Priority Data

Jun. 21, 2008  (DE) .......................... 10 2008 029 514

(51) Int. Cl.
 *C07C 69/96*  (2006.01)
 *C07C 68/06*  (2006.01)
(52) U.S. Cl.
 CPC ..................... *C07C 68/06* (2013.01)
(58) Field of Classification Search
 None
 See application file for complete search history.

(56) References Cited

U.S. PATENT DOCUMENTS

| | | | |
|---|---|---|---|
| 4,252,737 A | 2/1981 | Krimm et al. | |
| 4,330,665 A | 5/1982 | Krimm et al. | |
| 4,552,704 A | 11/1985 | Mark | |
| 4,554,110 A | 11/1985 | Mark | |
| 5,008,046 A | 4/1991 | Bremus et al. | |
| 5,149,856 A | 9/1992 | Schon et al. | |
| 5,334,742 A * | 8/1994 | Schon et al. | 558/274 |
| 5,344,954 A | 9/1994 | Schon et al. | |
| 5,354,923 A | 10/1994 | Schon et al. | |
| 6,387,222 B1 | 5/2002 | Tragut et al. | |

FOREIGN PATENT DOCUMENTS

| | | | |
|---|---|---|---|
| CA | 2013689 | 10/1991 | |
| DE | 3302525 A1 | 7/1984 | |
| DE | 3445552 A1 | 7/1985 | |
| DE | 3445555 A1 | 7/1985 | |
| DE | 3809417 A1 | 10/1989 | |
| DE | 4006520 A1 | 9/1991 | |
| DE | 4036594 A1 | 5/1992 | |
| DE | 4226755 A1 | 2/1994 | |
| DE | 4226756 A1 | 2/1994 | |
| DE | 19914966 A1 | 10/2000 | |
| EP | 0000879 A1 | 3/1979 | |
| EP | 0000880 A1 | 3/1979 | |
| EP | 0039452 A2 | 11/1981 | |
| EP | 0461274 A1 | 7/1991 | |
| EP | 0338760 B1 | 1/1995 | |
| EP | 0781760 A1 * | 7/1997 | .............. C07C 68/06 |
| EP | 1237842 B1 | 1/2007 | |
| EP | 1762559 A1 | 3/2007 | |
| EP | 1762560 A1 | 3/2007 | |
| EP | 1767516 A1 | 3/2007 | |
| EP | 1767517 A1 | 3/2007 | |
| EP | 1767518 A1 | 3/2007 | |
| EP | 1775280 A1 | 4/2007 | |
| EP | 1795522 A1 | 6/2007 | |
| JP | 54125617 A | 9/1979 | |
| JP | 57176932 A | 10/1982 | |
| JP | 61172852 A | 8/1986 | |
| JP | 64005588 A | 1/1989 | |
| JP | 0193560 A | 4/1989 | |
| JP | 0193580 A | 4/1989 | |
| JP | 200220351 A | 1/2002 | |
| WO | WO-2004016577 A1 | 2/2004 | |
| WO | WO-2004113264 A2 | 12/2004 | |
| WO | WO-2005000776 A2 | 1/2005 | |
| WO | WO-2006033291 A1 | 3/2006 | |

OTHER PUBLICATIONS

R. Agrawal et al. Ind. Eng. Chem. Res., vol. 35, pp. 2801-2807 (1996).*
R. Agrawal, et al., "On the Use of Intermediate Reboilers in the Rectifying Section and Condensers in the Stripping Section of a Distillation Column", Ind. Eng. Chem. Res., vol. 35, pp. 2801-2807 (1996).

* cited by examiner

Primary Examiner — Alicia L Otton
(74) Attorney, Agent, or Firm — Drinker Biddle & Reath LLP

(57) ABSTRACT

The invention provides a process for preparing diaryl carbonates from dialkyl carbonates and aromatic hydroxyl compounds using at least two reaction columns, a process section for recovering the dialkyl carbonate used in the reaction and for removing the alcohol of reaction, one or more process steps for removing the by-products obtained in the process which have a boiling point between that of the dialkyl carbonate and that of the alkyl aryl carbonate formed during the preparation of the diaryl carbonate, and a process step for further purification of the diaryl carbonate obtained from the reaction columns.

27 Claims, 14 Drawing Sheets

PROCESS FOR PREPARING DIARYL CARBONATES FROM DIALKYL CARBONATES

RELATED APPLICATIONS

Figure 1:
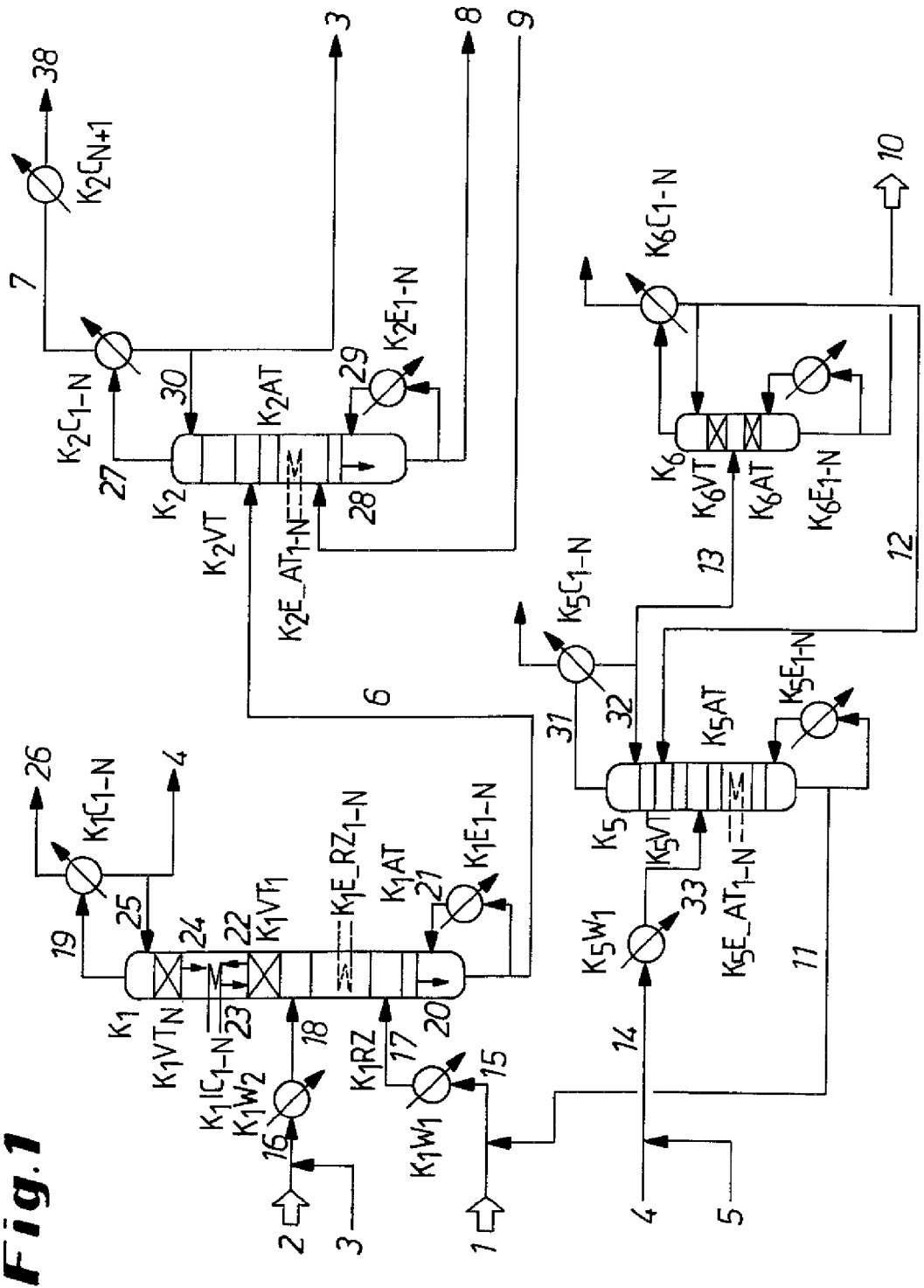

This application claims benefit to German Patent Application No. 10 2008 029 514.0, filed Jun. 21, 2008, which is incorporated herein by reference in its entirety for all useful purposes.

BACKGROUND OF THE INVENTION

The invention provides a process for preparing diaryl carbonates from dialkyl carbonates and aromatic hydroxyl compounds using at least two reaction columns, a process section for recovering the dialkyl carbonate used in the reaction and for removing the alcohol of reaction, one or more process steps for removing the by-products obtained in the process which have a boiling point between that of the dialkyl carbonate and that of the alkyl aryl carbonate formed during the preparation of the diaryl carbonate, and a process step for further purification of the diaryl carbonate obtained from the reaction columns.

The preparation of aromatic and aliphatic-aromatic carbonic esters (carbonates) by transesterification proceeding from aliphatic carbonic esters and aromatic hydroxyl compounds is known in principle. This is an equilibrium reaction wherein the equilibrium position is shifted almost entirely in the direction of the aliphatically substituted carbonates. It is therefore comparatively easy to prepare aliphatic carbonates from aromatic carbonates and alcohols. In order, however, to carry out the reaction in the reverse direction towards aromatic carbonates, it is necessary to shift the very unfavourable equilibrium effectively to the side of the aromatic carbonates, for which not only very active catalysts but also suitable process regimes have to be employed.

It is known that such equilibrium reactions can be carried out in columns and they can be shifted in this way advantageously in the direction of the desired product formation (e.g. U. Block, Chem.-Ing. Techn. 49, 151 (1977); DE-A 38 09 417; B. Schleper, B. Gutsche, J. Wnuck and L. Jeromin, Chem.-Ing.-Techn. 62, 226 (1990); Ullmans Encyclopädie der techn. Chemie, 4th Ed., vol. 3; p. 375 ff. 1973).

In the known processes, the transesterification is therefore also preferably effected continuously in a countercurrent transesterification in one or more reaction columns.

The processes known from the literature, for example EP-A 461 274, DE-A 42 26 755, DE-A 42 26 756, however, generally describe only those process steps in which the reaction to give the diaryl carbonate takes place by transesterification and/or disproportionation. WO-A 2006/033291, EP-A 1 775 280, EP-A 1 767 516, EP-A 1 767 517, EP-A 1767 518, EP-A 1 762 559 and EP-A 1 762 560 additionally give hints with regard to the apparatus configurations of reaction columns for preparation of diaryl carbonates. For the economic viability of a process, however, not just the process sections in the region of the reaction but, in some cases to a much greater degree, the subsequent steps for workup are of relevance. The literature to date contains only very little information on this subject.

Since the preparation of diaryl carbonates by reaction of an aromatic hydroxyl compound with a dialkyl carbonate, as experience has shown, is energetically very demanding, measures for reducing the energy consumption likewise play an important role. The literature currently available also gives very little information on this subject.

EP-A 781 760 describes a continuous process for preparing aromatic carbonates by reacting a dialkyl carbonate with an aromatic hydroxyl compound in the presence of a catalyst, continuously removing the aromatic carbonate formed in the reaction, the alcoholic by-products, the dialkyl carbonate and the aromatic hydroxyl compound, the dialkyl carbonate and the aromatic hydroxyl compound being recycled back into the reaction. However, it is not described how the dialkyl carbonate used in the reaction is separated from the alcoholic by-product (alcohol of reaction). However, experience has shown that this step is very energy-intensive and demanding, especially when dialkyl carbonate and alcohol of reaction are difficult to separate from one another. Moreover, the isolation of the diaryl carbonate after the reaction is not described either, but, owing to the high purity demands thereon, is very complicated. Moreover, no statements regarding possible energy savings are made.

EP-A 1 638 917 describes a process for recovering a product from a waste stream by contacting with an alkyl alcohol, the product recovered comprising diaryl carbonate, aromatic alcohol, alkyl salicylate and alkyl alcohol. One disadvantage of the process described is that the reaction is effected in three stages, which makes it very complicated. Another is that high-boiling waste streams are obtained at two points. Removal of the catalyst before the isolation of the diaryl carbonate gives rise to the first waste stream, and the subsequent workup consisting of two distillation columns to the second waste stream. The workup for isolation of the diaryl carbonate is thus very demanding both in apparatus and energetic terms. In addition, the quality of the diaryl carbonate thus prepared at 99.5% by weight is very poor and suitability for the preparation of polycarbonate is questionable. The separation of the mixture of alcohol of reaction and dialkyl carbonate obtained in the reaction is not described either.

WO-A 2005/1000776 describes a process for preparing an alkyl aryl ether which is formed in the reaction of a dialkyl carbonate with an aromatic hydroxyl compound. In this process, diaryl carbonate is additionally also obtained. The process structure comprises three reaction columns and two further distillation columns for the purpose of isolating the alkyl aryl ether. The fact that a controlled purification of the alkyl aryl ether is an aim in the process described here leads to the conclusion that the amount formed in the reaction is high. In the preparation of diaryl carbonates, however, the recovery of a high-purity alkyl aryl ether is not first priority, and the aim is instead minimum formation of this by-product obtained in the transesterification. Moreover, the reaction regime comprising three reaction stages is very complicated, and no statements are made regarding the workup of the diaryl carbonate and the separation of the mixture which is obtained in the reaction and comprises dialkyl carbonate and alcohol of reaction. EP-A 1 237 842 also describes a comparable process, and therefore the disadvantages already mentioned likewise apply to this.

WO-A 2004/016577 describes a process for preparing aromatic carbonates from dialkyl carbonate and an aromatic hydroxyl compound in the presence of a catalyst in a plurality of separate and series-connected reaction zones of a reactor arrangement, wherein the heat of condensation obtained in the condensation of the vapour stream of the last reaction zone is used to heat the liquid stream introduced into the first reaction zone. However, a disadvantage of this process is the complicated reactor arrangement. In addition, the energetic integration of this process is in need of improvement and is limited only to the process section of reaction. Subsequent steps for the workup are not described.

JP-A 2002-020351 describes a batchwise process for preparing diaryl carbonate, from which heat can be utilized for steam raising. However, disadvantages of this process are the batchwise performance and the reactor arrangement used for the reaction, which has an attached distillation column. Subsequent steps for the workup are not described.

There was accordingly still a need to provide a process for preparing aromatic carbonates, preferably diaryl carbonates, which includes a workup of product and waste streams, which does not have the disadvantages specified above and in which, compared to the known processes specified above, energy integration is possible in an efficient manner and improved energy integration can be achieved.

The object on which the invention was based accordingly consisted in providing a process for preparing aromatic carbonates, preferably diaryl carbonates, which includes a workup of product and waste streams and in which, compared to known processes, energy integration is possible in an efficient manner and improved energy integration can be achieved.

EMBODIMENTS OF THE INVENTION

An embodiment of the present invention is a process for preparing a diaryl carbonate from a dialkyl carbonate and an aromatic hydroxyl compound comprising the steps of:
  (a) reacting a dialkyl carbonate with an aromatic hydroxyl compound in the presence of a transesterification catalyst in a first reaction column, wherein said first reaction column comprises a rectifying section in the upper part of said first reaction column column and a reaction zone below said rectifying section, wherein said reaction zone comprises at least two sectors;
  (b) feeding bottom product produced in said first reaction column in step (a) to a further reaction column, wherein said further reaction column comprises a rectifying section in the upper part of said further reaction column and a reaction zone below said rectifying section, and further reacting said bottom product in said reaction zone;
  (c) separating at least a portion of unconverted dialkyl carbonate from the reaction columns of steps (a) and/or (b) or formed during the reaction from alkyl alcohol formed during the reaction in at least one distillation column;
  (d) feeding at least a portion of vapor comprising said aromatic hydroxyl compound withdrawn from the top of said further reaction column, optionally after condensing said vapor in a condenser, to a distillation column to remove one or more compounds having a boiling point between that of said dialkyl carbonate and that of alkyl aryl carbonate formed during the preparation of said diaryl carbonate; and
  (e) feeding bottom product produced in said further reaction column in step (b), wherein said bottom product comprises diaryl carbonate, to a distillation column for purification, wherein said distillation column comprises a rectifying section in the upper part of said distillation column and a stripping section in the lower part of said distillation column;
wherein at least one of said first reaction column and said further reaction column is equipped with a condenser and the heat of condensation obtained by condensation in said condenser is directly or indirectly recycled back into said process.

Another embodiment of the present invention is the above process, wherein said rectifying section of said first reaction column comprises an intermediate condenser and heat of condensation obtained by condensation in said intermediate condenser is directly or indirectly recycled back into said process.

Another embodiment of the present invention is the above process, wherein said heat of condensation is directly or indirectly used to separate said dialkyl carbonate from said alkyl alcohol in step (c) and/or to evaporate said dialkyl carbonate fed into said first reaction column in step (a).

Another embodiment of the present invention is the above process, wherein said heat of condensation is directly or indirectly used to separate said dialkyl carbonate from said alkyl alcohol in step (c) and to evaporate said dialkyl carbonate fed into said first reaction column in step (a).

Another embodiment of the present invention is the above process, wherein said further reaction column comprises a condenser at the top of said further reaction column and heat of condensation obtained by condensation in said condenser is directly or indirectly recycled back into said process.

Another embodiment of the present invention is the above process, wherein said heat of condensation is directly or indirectly used to separate said dialkyl carbonate from said alkyl alcohol in step (c) and/or to evaporate said dialkyl carbonate fed into said first reaction column in step (a).

Another embodiment of the present invention is the above process, wherein said heat of condensation is directly or indirectly used to separate said dialkyl carbonate from said alkyl alcohol in step (c) and to evaporate said dialkyl carbonate fed into said first reaction column in step (a).

Another embodiment of the present invention is the above process, wherein said further reaction column comprises a condenser at the top of said further reaction column and heat of condensation obtained by condensation in said condenser is directly or indirectly recycled back into said process.

Another embodiment of the present invention is the above process, wherein said heat of condensation is directly or indirectly used to separate said dialkyl carbonate from said alkyl alcohol in step (c) and/or to evaporate said dialkyl carbonate fed into said first reaction column in step (a).

Another embodiment of the present invention is the above process, wherein said heat of condensation is directly or indirectly used to separate said dialkyl carbonate from said alkyl alcohol in step (c) and to evaporate said dialkyl carbonate fed into said first reaction column in step (a).

Another embodiment of the present invention is the above process, wherein at least a portion of said heat of condensation obtained by condensation in said condenser at the top of said further reaction column is used to separate said dialkyl carbonate from said alkyl alcohol in step (c) and at least a portion of said heat of condensation obtained by condensation in said intermediate condenser is directly or indirectly used to evaporate said dialkyl carbonate fed into said first reaction column in step (a).

Another embodiment of the present invention is the above process, wherein said bottom product produced in said further reaction column in step (b) comprises said transesterification catalyst.

Another embodiment of the present invention is the above process, wherein said bottom product produced in said further reaction column in step (b) is fed to a distillation column for purification, wherein a diaryl carbonate-containing sidestream is withdrawn from said distillation column.

Another embodiment of the present invention is the above process, wherein said bottom product produced in said further reaction column in step (b) comprises a compound having a boiling point between that of said diaryl carbonate and that of alkyl aryl carbonate formed as a by-product during the preparation of said diaryl carbonate as an impurity, wherein said compound is withdrawn from said distillation column in a further sidestream and optionally recycled into said first reaction column of step (a) or said further reaction column of step (b).

Another embodiment of the present invention is the above process, wherein said distillation column is a dividing wall column.

Another embodiment of the present invention is the above process, wherein said dialkyl carbonate removed in step (c) is fed back to said first reaction column in step (a), optionally after further purification.

Another embodiment of the present invention is the above process, wherein said one or more compounds having a boiling point between that of said dialkyl carbonate and that of alkyl aryl carbonate formed during the preparation of said diaryl carbonate is said aromatic hydroxyl compound of said vapor and wherein said aromatic hydroxyl compound is fed to said first reaction column in step (a).

Another embodiment of the present invention is the above process, wherein said vapour comprising said aromatic hydroxyl compound is fed to a first distillation column and at least one further distillation column, wherein the bottom product produced in said first distillation column is fed to a second distillation column.

Another embodiment of the present invention is the above process, wherein said aromatic hydroxyl compound is withdrawn from a first and only distillation column as a bottom product or from a second or further distillation column as a sidestream.

Another embodiment of the present invention is the above process, wherein product withdrawn from the top of said first distillation column comprises dialkyl carbonate, wherein at least a portion of said product is fed to said distillation column in step (c).

Another embodiment of the present invention is the above process, wherein at least one of said reaction columns and/or at least one of said distillation columns used in said process comprises a top condenser integrated into said reaction column and/or distillation column, wherein the d/D ratio of the diameter of the vapour line from reaction column and/or distillation column to top condenser is in the range of from 0.2 to 1.

Another embodiment of the present invention is the above process, wherein lines and units which conduct mixtures having a melting point of more than 30° C. are heated to temperatures above this melting point.

Another embodiment of the present invention is the above process, wherein lines and units which conduct mixtures having a melting point of more than 40° C. are heated to temperatures above this melting point.

Another embodiment of the present invention is the above process, wherein
  a. at least a portion of a catalyst-containing stream is obtained from the bottom product produced in said distillation column of step (e) and is recycled, optionally after further purification, back into said process, preferably into process step (a),
  b. at least a portion of a stream comprising an aromatic hydroxyl compound and an alkyl aryl carbonate obtained from said distillation column of step (e) is recycled back into said process, and
  c. at least a portion of one or more compounds having a boiling point above the boiling point of said diaryl carbonate and at least a portion of one or more compounds whose boiling point is between that of said dialkyl carbonate and that of alkyl aryl carbonate formed during the preparation of said diaryl carbonate are discharged from said process, together or separately from one another, from said distillation column of step (e).

Another embodiment of the present invention is the above process, wherein at least a portion of said catalyst-containing stream obtained from the bottom product produced in said distillation column of step (e) is recycled, optionally after further purification, back into process step (a). Another embodiment of the present invention is the above process, wherein at least a portion of said stream comprising an aromatic hydroxyl compound and an alkyl aryl carbonate obtained from said distillation column of step (e) is recycled back into process step (a) or (b).

DESCRIPTION OF THE INVENTION

It has been found that, surprisingly, a process for preparing at least one diaryl carbonate from at least one dialkyl carbonate and at least one aromatic hydroxyl compound, by
  (a) reacting the dialkyl carbonate(s) in the presence of at least one transesterification catalyst with the aromatic hydroxyl compound(s) in a first reaction column comprising at least one rectifying section in the upper part of the column and at least one reaction zone below the rectifying section which has at least two sectors,
  (b) feeding the bottom product of the first reaction column to at least one further reaction column comprising at least one rectifying section in the upper part of the column and at least one reaction zone below the rectifying section, and converting it further therein,
  (c) separating the dialkyl carbonate unconverted in the reaction columns of steps (a) and/or (b) or formed during the reaction fully or partly from the alkyl alcohol formed during the reaction in at least one further process step comprising at least one distillation column,
  (d) feeding the vapour containing aromatic hydroxyl compound(s) withdrawn at the top of at least one reaction column from (b), optionally after condensation in at least one condenser, fully or partly to at least one further process step comprising at least one distillation column to remove compounds whose boiling point is between that of the dialkyl carbonate and that of the alkyl aryl carbonate formed during the preparation of the diaryl carbonate, and
  (e) feeding the bottom product which comprises diaryl carbonate and is obtained in the further reaction column(s) from step (b) to at least one further process step for purification in at least one distillation column comprising at least one rectifying section in the upper part of the column and at least one stripping section in the lower part of the column,
wherein at least one of the reaction column(s) selected from the first reaction column or the further reaction column(s) is equipped with one or more condensers and the heat of condensation obtained by condensation in these condensers is recycled directly or indirectly back into the process, enables both a workup of product and waste streams and efficient energy integration.

The present invention therefore provides a process for preparing at least one diaryl carbonate from at least one dialkyl carbonate and at least one aromatic hydroxyl compound, by
  (a) reacting the dialkyl carbonate(s) in the presence of at least one transesterification catalyst with the aromatic hydroxyl compound(s) in a first reaction column comprising at least one rectifying section in the upper part of the column and at least one reaction zone below the rectifying section which has at least two sectors, (b) feeding the bottom product of the first reaction column to at least one further reaction column comprising at least one rectifying section in the upper part of the column and at least one reaction zone below the rectifying section, and converting it further therein, (c) separating the dialkyl carbonate unconverted in the reaction columns of steps (a) and/or (b) or formed during the reaction fully or partly from the alkyl alcohol formed during the reaction in at least one further process step comprising at least one distillation column, (d) feeding the vapour containing aromatic hydroxyl compound(s) withdrawn at the top of at least one reaction column from (b), optionally after condensation in at least one condenser, fully or partly to at least one further process step comprising at least one distillation column to remove compounds whose boiling point is between that of the dialkyl carbonate and that of the alkyl aryl carbonate formed during the preparation of the diaryl carbonate, and (e) feeding the bottom product which comprises diaryl carbonate and is obtained in the further reaction column(s) from step (b) to at least one further process step for purification in at least one distillation column comprising at least one rectifying section in the upper part of the column and at least one stripping section in the lower part of the column, characterized in that at least one of the reaction column(s) selected from the first reaction column or the further reaction column(s) is equipped with one or more condensers and the heat of condensation obtained by condensation in these condensers is recycled directly or indirectly back into the process.

Diaryl carbonates prepared in the context of the invention are preferably those of the general formula (I)

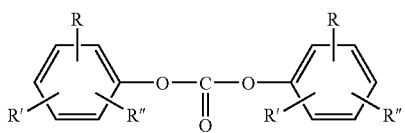
(I)

where R, R' and R" are each independently H, linear or branched, optionally substituted $C_1$-$C_{34}$-alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl, $C_6$-$C_{34}$-aryl or a halogen radical, preferably a chlorine radical, and R, R' and R" on the two sides of the formula (I) may be the same or different. R may also be —COO—R''' where R''' is H, branched or unbranched $C_1$-$C_{34}$-alkyl, preferably $C_1$-$C_6$-alkyl, more preferably $C_1$-$C_4$-alkyl, $C_1$-$C_{34}$-alkoxy, preferably $C_1$-$C_6$-alkoxy, more preferably $C_1$-$C_4$-alkoxy, $C_5$-$C_{34}$-cycloalkyl, $C_7$-$C_{34}$-alkylaryl or $C_6$-$C_{34}$-aryl. Preferably, R, R' and R" on both sides of the formula (I) are the same. Most preferably, R, R' and R" are each H.

Diaryl carbonates of the general formula (I) are, for example: diphenyl carbonate, methylphenyl phenyl carbonates and di(methylphenyl) carbonates, also as a mixture, where the position of the methyl group on the phenyl rings may be as desired, and also dimethylphenyl phenyl carbonates and di(dimethylphenyl) carbonates, also as a mixture, where the position of the methyl groups on the phenyl rings may be as desired, chlorophenyl phenyl carbonates and di(chlorophenyl) carbonates, where the position of the methyl group on the phenyl rings may be as desired, 4-ethylphenyl phenyl carbonate, di(4-ethylphenyl) carbonate, 4-n-propylphenyl phenyl carbonate, di(4-n-propylphenyl) carbonate, 4-isopropylphenyl phenyl carbonate, di(4-isopropylphenyl) carbonate, 4-n-butylphenyl phenyl carbonate, di(4-n-butylphenyl) carbonate, 4-isobutylphenyl phenyl carbonate, di(4-isobutylphenyl) carbonate, 4-tert-butylphenyl phenyl carbonate, di(4-tert-butylphenyl) carbonate, 4-n-pentylphenyl phenyl carbonate, di(4-n-pentylphenyl) carbonate, 4-n-hexylphenyl phenyl carbonate, di(4-n-hexylphenyl) carbonate, 4-isooctylphenyl phenyl carbonate, di(4-isooctylphenyl) carbonate, 4-n-nonylphenyl phenyl carbonate, di(4-n-nonylphenyl) carbonate, 4-cyclohexylphenyl phenyl carbonate, di(4-cyclohexylphenyl) carbonate, 4-(1-methyl-1-phenylethyl)phenyl phenyl carbonate, di[4-(1-methyl-1-phenylethyl)phenyl]carbonate, biphenyl-4-yl phenyl carbonate, di(biphenyl-4-yl) carbonate, 1-naphthyl phenyl carbonate, 2-naphthyl phenyl carbonate, di(1-naphthyl) carbonate, di(2-naphthyl) carbonate, 4-(1-naphthyl)phenyl phenyl carbonate, 4-(2-naphthyl)phenyl phenyl carbonate, di[4-(1-naphthyl)phenyl]carbonate, di[4-(2-naphthyl)phenyl]carbonate, 4-phenoxyphenyl phenyl carbonate, di(4-phenoxyphenyl) carbonate, 3-pentadecylphenyl phenyl carbonate, di(3-pentadecylphenyl) carbonate, 4-tritylphenyl phenyl carbonate, di(4-tritylphenyl) carbonate, (methyl salicylate) phenyl carbonate, di(methyl salicylate) carbonate, (ethyl salicylate) phenyl carbonate, di(ethyl salicylate) carbonate, (n-propyl salicylate) phenyl carbonate, di(n-propyl salicylate) carbonate, (isopropyl salicytate) phenyl carbonate, di(isopropyl salicylate) carbonate, (n-butyl salicylate) phenyl carbonate, di(n-butyl salicylate) carbonate, (isobutyl salicylate) phenyl carbonate, di(isobutyl salicylate) carbonate, (tert-butyl salicylate) phenyl carbonate, di(tert-butyl salicylate) carbonate, di(phenyl salicylate) carbonate and di(benzyl salicylate) carbonate.

Preferred diaryl carbonates are: diphenyl carbonate, 4-tert-butylphenyl phenyl carbonate, di(4-tert-butylphenyl) carbonate, biphenyl-4-yl phenyl carbonate, di(biphenyl-4-yl) carbonate, 4-(1-methyl-1-phenylethyl)phenyl phenyl carbonate and di[4-(1-methyl-1-phenylethyl)phenyl]carbonate.

Particular preference is given to diphenyl carbonate.

In the context of the invention, dialkyl carbonates used with preference are those of the formula (II)

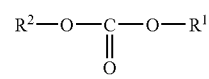
(II)

where $R^1$ and $R^2$ are each independently linear or branched, optionally substituted $C_1$-$C_{34}$-alkyl, preferably $C_1$-$C_6$-alkyl, more preferably $C_1$-$C_4$-alkyl. $R^1$ and $R^2$ may be the same or different. $R^1$ and $R^2$ are preferably the same.

In the context of the invention, $C_1$-$C_4$-alkyl is, for example, methyl, ethyl, n-propyl, isopropyl, n-butyl, sec-butyl, tert-butyl; $C_1$-$C_6$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-2-methylpropyl; $C_1$-$C_{34}$-alkyl is additionally, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical, for example in aralkyl or alkylaryl radicals. Alkylene radicals in the corresponding hydroxyalkyl or aralkyl or alkylaryl radicals are, for example, the alkylene radicals corresponding to the above alkyl radicals.

Aryl is a carbocyclic aromatic radical having 6 to 34 skeleton carbon atoms. The same applies to the aromatic moiety of an arylalkyl radical, also known as aralkyl radical, and also to aryl constituents of more complex groups, for example arylcarbonyl radicals.

Arylalkyl or aralkyl is in each case independently a straight-chain, cyclic, branched or unbranched alkyl radical as defined above, which may be mono-, poly- or persubstituted by aryl radicals as defined above.

The above lists are illustrative and should not be understood as a limitation.

Preferred dialkyl carbonates are dimethyl carbonate, diethyl carbonate, di(n-propyl) carbonate, di(isopropyl) carbonate, di(n-butyl) carbonate, di(sec-butyl) carbonate, di(tert-butyl) carbonate or dihexyl carbonate. Particular preference is given to dimethyl carbonate or diethyl carbonate. Very particular preference is given to dimethyl carbonate.

In the context of the invention, suitable aromatic hydroxyl compounds are preferably those of the general formula (III)

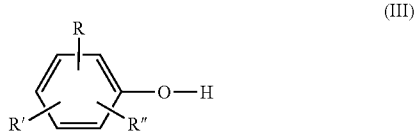

in which R, R' and R" may each independently be as defined for the general formula (I).

Such aromatic hydroxyl compounds are, for example: phenol, o-, m- or p-cresol, also as a mixture of the cresols, dimethylphenol, also as a mixture, where the position of the methyl groups on the phenol ring may be as desired, e.g. 2,4-, 2,6-, or 3,4-dimethylphenol, o-, m- or p-chlorophenol, o-, m- or p-ethylphenol, o-, m- or p-n-propylphenol, 4-isopropylphenol, 4-n-butylphenol, 4-isobutylphenol, 4-tert-butylphenol, 4-n-pentylphenol, 4-n-hexylphenol, 4-isooctylphenol, 4-n-nonylphenol, o-, m- or p-methoxyphenol, 4-cyclohexylphenol, 4-(1-methyl-1-phenylethyl)phenol, biphenyl-4-ol, 1-naphthol, 2-1-naphthol, 4-(1-naphthyl)phenol, 4-(2-naphthyl)phenol, 4-phenoxyphenol, 3-pentadecylphenol, 4-tritylphenol, methylsalicylic acid, ethylsalicylic acid, n-propylsalicylic acid, isopropylsalicylic acid, n-butylsalicylic acid, isobutylsalicylic acid, tert-butylsalicylic acid, phenylsalicylic acid and benzylsalicylic acid.

Preferred diaryl compounds are phenol, 4-tert-butylphenol, biphenyl-4-ol and 4-(1-methyl-1-phenylethyl)phenol.

Particular preference is given to phenol.

Alkyl aryl carbonates obtained as intermediates in the context of the invention are preferably those of the general formula (IV)

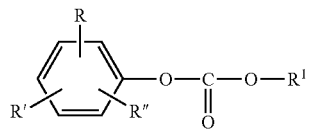

in which R, R' and R" may each be as defined for the general formula (I), and $R^1$ as defined for the general formula (II).

Preferred alkyl aryl carbonates are methyl phenyl carbonate, ethyl phenyl carbonate, propyl phenyl carbonate, butyl phenyl carbonate and hexyl phenyl carbonate, methyl o-cresyl carbonate, methyl p-cresyl carbonate, ethyl o-cresyl carbonate, ethyl p-cresyl carbonate, methyl or ethyl p-chlorophenyl carbonate. Particularly preferred alkyl aryl carbonates are methyl phenyl carbonate and ethyl phenyl carbonate. Very particular preference is given to methyl phenyl carbonate.

Both the dialkyl carbonates suitable for the process according to the invention and the aromatic hydroxyl compounds are known to those skilled in the art and commercially available or can be prepared by processes likewise known to those skilled in the art.

In the process according to the invention, the aromatic hydroxyl compound(s) and the dialkyl carbonate (s) are used in the first reaction column preferably in a molar ratio of 1:0.1 to 1:10, more preferably of 1:0.2 to 1:5, most preferably of 1:0.5 to 1:3. The molar ratio specified here does not take account of the recycling of aromatic hydroxyl compound or dialkyl carbonate into the reaction column via one or more top condenser(s) or one or more bottom evaporator(s) if present.

The process according to the invention is carried out in at least two reaction columns.

Useful first and second reaction columns or any third or further column(s) include columns known to those skilled in the art. These are, for example, distillation and rectification columns, preferably reactive distillation and reactive rectification columns.

The first reaction column comprises at least one rectifying section in the upper part of the column and at least one reaction zone below the rectifying section which has at least two sectors. Each of the two sectors independently has preferably 0 to 20, preferably 0.1 to 20, theoretical plates each. In preferred embodiments, at least one rectifying section of the first reaction column is equipped with at least one intermediate condenser. The intermediate condenser is preferably mounted between the two sectors of the rectifying section. In this case, the rectifying section is divided into an upper rectifying section and a lower rectifying section. In the context of the invention, a "sector" is notable in that a feed and/or withdrawal point is present below and/or above this sector.

The first reaction column is preferably operated in countercurrent, in which case the aromatic hydroxyl compound is preferably conducted in liquid form from the top to the bottom in at least one reaction zone of this column and the dialkyl carbonate is conducted countercurrently to this liquid stream in gaseous form. The first reaction column is preferably operated in such a way that one or more streams comprising the aromatic hydroxyl compound and optionally dissolved transesterification catalyst are metered into at least one reaction zone, preferably into the upper third of the reaction zone, preferably with the temperature existing at this point in the column, in liquid form or with only a low gaseous content, the gaseous content preferably being less than 20% by weight. In addition, one or more streams comprising the dialkyl carbonate are passed into the reaction zone, preferably in the lower third of this reaction zone, the metered addition preferably being effected in gaseous or superheated form. In preferred embodiments, the overheating of the vapour stream may be 0 to 50° C. In addition, the dew point temperature is preferably guided by the pressure which exists in the reaction zone at the metering point of the particular stream comprising dialkyl carbonate.

After passing through the reaction zone(s), the alkyl alcohol formed during the reaction, after passing through the rectifying section(s), is withdrawn at the top of the first reaction column. The alkyl alcohol formed during the reaction, also known as alcohol of reaction, in the context of the invention, is the alcohol released in the course of transesterification, preferably $R^1$—OH and/or $R^2$—OH, where $R^1$ and $R^2$ are each defined as specified for the general formula (II). The stream withdrawn at the top of the first reaction column generally comprises, in addition to the alkyl alcohol formed during the reaction, excess or unconverted dialkyl carbonate and low-boiling secondary compounds, for example carbon dioxide or dialkyl ether. Owing to the rectifying section(s) present, this stream comprises only small amounts of higher-boiling components, for example the aromatic hydroxyl compound. The rectifying section serves to remove the higher-boiling components which are also evaporated in the reaction zone, for example the aromatic hydroxyl compound or alkyl aryl carbonate, from the low-boiling alcohols of reaction or dialkyl carbonates. This has the advantage that the separation of the alkyl alcohols formed during the reaction from the dialkyl carbonates can be performed at a low temperature level.

In preferred embodiments, the first reaction column is operated under reflux conditions. "Reflux conditions" is understood to mean a method in which the vapour stream is condensed fully or partly at the upper end of the rectifying section and the condensate obtained is recycled partly or fully as reflux back to the upper end of the rectifying section. The reflux ratio is preferably 0.1 to 20, more preferably 0.1 to 10 and most preferably 0.1 to 3, the reflux ratio in the context of the invention corresponding to the weight ratio of condensate recycled into the column to vapour withdrawn at the top of the column without recycled condensate.

In preferred embodiments, the first reaction column has at least one stripping section below a reaction zone.

The first reaction column may further preferably be equipped with one or more bottom evaporator(s). When the first reaction column is designed with a stripping section, preference is given to additionally using a bottom evaporator which fully or partly evaporates the liquid effluxing from the stripping section. This fully or partially evaporated liquid stream is recycled fully or partly back into the first reaction column. In the case of an embodiment without a stripping section, in any bottom evaporator used, the liquid effluxing from the reaction zone is evaporated fully or partly and recycled fully or partly back into the first reaction column.

Additionally preferably, the first reaction column may have one or more intermediate heaters or intermediate evaporators in the region of the stripping section and/or of the reaction zone.

In the preferred embodiments in which at least one rectifying section of the first reaction column is equipped with at least one intermediate condenser, the rectifying section of the first reaction column, which is equipped with at least one intermediate condenser, is divided into a lower rectifying section and an upper rectifying section (two sectors), of which the lower rectifying section is present below the intermediate condenser and the upper rectifying section above the intermediate condenser.

The rectifying section(s) with at least one intermediate condenser may, in preferred embodiments, be accommodated in the reaction column together with the reaction section(s) and optionally at least one stripping section. In this case, the vaporous mixture coming from the reaction zone(s) is passed from below into a lower sector of the rectifying section and/or if appropriate into the lower rectifying section, which depletes the aromatic hydroxyl compound. The vaporous mixture coming from this lower sector or if appropriate the lower rectifying section is passed into an intermediate condenser, where it partly condenses out, and the condensate obtained is fed in at the upper end of the lower sector of the rectifying section or if appropriate to the lower rectifying section.

In a further preferred embodiment of the process according to the invention, the intermediate condenser is not integrated into the first reaction column, but configured as a separate intermediate condenser outside the first reaction column.

In a further preferred embodiment of the process according to the invention, intermediate condenser and the upper sector of the rectifying section are not integrated into the reaction column but accommodated separately outside the first reaction column.

Below the reaction zone and any stripping section present, a mixture comprising alkyl aryl carbonate, excess or unconverted phenol, diaryl carbonate, transesterification catalysts, dialkyl carbonate, alcohol of reaction and high-boiling compounds which form in the reaction or are already present in the reactants is obtained. When a stripping section is used, the content of low-boiling compounds, for example dialkyl carbonate and alcohol of reaction, is reduced, forming further alkyl aryl carbonate and/or diaryl carbonate under some circumstances in the presence of the transesterification catalyst. The energy required for this purpose is preferably supplied by one or more evaporators.

In all sections of the first reaction column and also of the columns described hereinafter, i.e. both in rectifying and/or stripping section and/or in the reaction zone, random packings or structured packings can be used to achieve the separating performance in question. The random packings or structured packings for use are those customary for distillations, as described, for example, in Ullmann's Encyclopädie der Technischen Chemie, 4th Ed., Vol. 2, p. 528 ff. Examples of random packings include Raschig or Pall and Novalox rings, Berl, Intalex or Torus saddles, Interpack bodies, and examples of structured packings include sheet metal and fabric packings (for example BX packings, Montz Pak, Mellapak, Melladur, Kerapak and CY packing) made of various materials, such as glass, stoneware, porcelain, stainless steel, plastic. Preference is given to random packings and structured packings which have a large surface area, good wetting and sufficient residence time of the liquid phase. These are, for example, Pall and Novalox rings, Bert saddles, BX packings, Montz Pak, Mellapak, Melladur, Kerapak and CY packings.

In the case of use of random packings and/or structured packings, a sector can be divided into a plurality of parts when the sector has more than 4, preferably more than 10 and more preferably more than 15 theoretical plates.

Alternatively suitable are also column trays, for example sieve trays, bubble-cap trays, valve trays, tunnel-cap trays. In the reaction zone(s) of the reaction column, particular preference is given to column trays with high residence times coupled with good mass transfer, for example bubble-cap trays, valve trays or tunnel-cap trays with high overflow weirs.

The number of theoretical plates of the reaction zone of the first reaction column is preferably 3 to 50, more preferably 10 to 50 and most preferably 10 to 40. The liquid holdup is preferably 1 to 80%, more preferably 5 to 70% and most preferably 7 to 60% of the internal column volume of the reaction zone. The more specific design of the reaction zone (s), of any stripping section to be used and of the rectifying section(s) can be undertaken by the person skilled in the art.

In the first reaction column, the column diameter in the region of the reaction zone is guided by the gas throughput, but only with restrictions. It is also influenced by the hold-up to be achieved.

In the case of use of hold-up trays, the liquid level on the trays should preferably be 50 to 1000, more preferably 100 to 500 and most preferably 100 to 250 mm in order to limit the pressure drop of the column to a sensible degree. The pressure drop of the column should preferably be less than 50, more preferably less than 30 and most preferably less than 25% of the top pressure.

Under these boundary conditions, the F factor in the column is preferably between 0.05 and 2.5, preferably 0.05 to 1.5 and more preferably between 0.08 and 1 $Pa^{0.5}$. The tray separation may be preferably 250 to 1500 mm, more preferably 300 to 1000 and most preferably 500 to 1000 mm. The F factor is a measure of the gaseous hydraulic loading of the column and is calculated as follows:

$$F\ factor = gas\ density^{1/2} \cdot gas\ velocity$$

A suitable column design of the rest of the distillation and/or reaction columns used in the process, which includes the design of the column height and of the column diameter, the selection of the column internals and the dimensioning of the feed and withdrawal lines, is known to those skilled in the art and can be taken from the relevant literature (for example Distillation Design, Henry Z. Kister, McGraw Hill; Distillation Operation, Henry Z. Kister, McGraw Hill; Perry's Chemical Engineering Handbook; Perry & Green).

The temperature of the reaction zone(s) is preferably in the range from 100 to 300° C., more preferably from 120 to 250° C., most preferably from 150 to 240° C. In preferred embodiments, an optimal reaction temperature is established in the reaction zone firstly through the selection of the operating conditions and secondly through additional heat supply in the region of one or more reaction trays. The heat can be supplied to the reaction trays either by means of heat exchangers or via reaction trays with means of introducing heat. It is advantageous to carry out the inventive transesterification not only at atmospheric pressure but also at elevated or reduced pressure. The pressure in the reaction zone is therefore preferably in the range of 0.5 to 20 bar (absolute), more preferably 0.8 to 15 bar (absolute), most preferably 0.9 to 10 bar (absolute).

For the reaction steps which occur in the first reaction column, it is possible to use transesterification catalysts known from the literature. These are transesterification catalysts known from the literature for the dialkyl carbonate-phenol transesterification, for example metal compounds such as $AlX_3$, $TiX_3$, $UX_4$, $TiX_4$, $VOX_3$, $VX_5$, $ZnX_2$, $FeX_3$, $PbX_2$ and $SnX_4$, in which X represents halogen, acetoxy, alkoxy or aryloxy radicals (DE-A 2 58 412). Particularly preferred catalysts usable in accordance with the invention are metal compounds such as $AlX_3$, $TiX_4$, $PbX_2$ and $SnX_4$, for example titanium tetrachloride, titanium tetramethoxide, titanium tetraphenoxide, titanium tetraethoxide, titanium tetraisopropoxide, titanium tetradodecoxide, tin tetraisooctoxide and aluminium triisopropoxide. Very particular preference is given to metal compounds $TiX_4$. The metal compounds mentioned are used preferably in amounts of 0.001 to 5% by weight, preferably of 0.005 to 5% by weight and more preferably of 0.01 to 5% by weight, based on the weight of the reaction mixture to be converted.

In the context of the invention, halogen is fluorine, chlorine or bromine, preferably fluorine or chlorine, more preferably chlorine.

Further catalysts usable in accordance with the invention are organotin compounds of the general formula $(R^{11})_{4-x}$—$Sn(Y)_x$ in which Y is an $OCOR^{12}$, OH or OR radical, where $R^{12}$ is $C_1$-$C_{12}$-alkyl, $C_6$-$C_{12}$-aryl or $C_7$-$C_{13}$-alkylaryl, $R^{11}$, independently of $R^{12}$, is as defined for $R^{12}$, and x is an integer from 1 to 3, dialkyltin compounds having 1 to 12 carbon atoms in the alkyl radical or bis(trialkyltin) compounds, for example trimethyltin acetate, triethyltin benzoate, tributyltin acetate, triphenyltin acetate, dibutyltin diacetate, dibutyltin dilaurate, dioctyltin dilaurate, dibutyltin adipate, dibutyldimethoxytin, dimethyltin glycolate, dibutyldiethoxytin, triethyltin hydroxide, hexaethylstannoxane, hexabutylstannoxane, dibutyltin oxide, dioctyltin oxide, butyltin triisooctoxide, octyltin triisooctoxide, butylstannoic acid and octylstannoic acid, in amounts of 0.001 to 20% by weight (cf. EP 879, EP 880, EP 39 452, DE-A 34 45 555, JP 79/63023), polymeric tin compounds of the formula -[—$R^{11}Sn$—O—]- in which R and $R^{11}$ are each independently as defined above for $R^{12}$, for example poly[oxy(dibutylstannylene)], poly[oxy(dioctylstannylene)], poly[oxy(butylphenylstannylene)] and poly[oxy(diphenylstannylene)] (DE-A 34 45 552), polymeric hydroxystannoxanes of the formula -[—RSn(OH)—O—]-, for example poly(ethylhydroxystannoxane), poly(butylhydroxystannoxane), poly(octylhydroxystannoxane), poly(undecylhydroxystannoxane) and poly(dodecylhydroxystannoxanes) in amounts of 0.001 to 20% by weight, preferably of 0.005 to 5% by weight, based on dialkyl carbonate (DE-A 40 06 520). Further tin compounds usable in accordance with the invention are Sn(II) oxides of the general formula

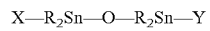

$$X—R_2Sn—O—R_2Sn—Y$$

in which X and Y are each independently OH, SCN, $OR^{13}$, $OCOR^{13}$ or halogen and R is alkyl, aryl, in which $R^{13}$ is as defined above for $R^{12}$ (EP 0 338 760).

As further catalysts usable in accordance with the invention are suitable lead compounds, optionally together with triorganophosphines, a chelate compound or an alkali metal halide, for example $Pb(OH)_2$-$2PbCO_3$, $Pb(OCO—CH_3)_2$, $Pb(OCO—CH_3)_2$-$2LiCl$, $Pb(OCO—CH_3)_2$·$2PPh_3$, in amounts of 0.001 to 1 mol, preferably of 0.005 to 0.25 mol, per mole of dialkyl carbonate (JP 57/176932, JP 01/093580), and also other lead(II) and lead(IV) compounds, such as PbO, $PbO_2$, minium, plumbites and plumbates (JP 01/093560), iron(III) acetate (JP 61/1 72 852), and also copper salts and/or metal complexes, for example of alkali metals, zinc, titanium and iron (JP 89/005588).

In addition, heterogeneous catalyst systems are usable in the processes according to the invention. These are, for example, mixed oxides of silicon and titanium, which are obtainable by combined hydrolysis of silicon and titanium halides (IP 54/125617), or titanium dioxides with a high BET surface area of >20 $m^2/g$ (DE-A 40 36 594). Preferred catalysts for the process according to the invention are the above-specified metal compounds $AlX_3$, $TiX_3$, $UX_4$, $TiX_4$, $VOX_3$, $VX_5$, $ZnX_2$, $FeX_3$, $PbX_2$ and $SnX_4$. Particular preference is given to $AlX_3$, $TiX_4$, $PbX_2$ and $SnX_4$, among which mention should be made by way of example of titanium tetrachloride, titanium tetramethoxide, titanium tetraphenoxide, titanium tetraethoxide, titanium tetraisopropoxide, titanium tetradodecoxide, tin tetraisooctoxide and aluminium triisopropoxide. Very particular preference is given to metal compounds $TiX_4$. Especially preferred are titanium tetramethoxide, titanium tetraphenoxide and titanium tetraethoxide.

The catalyst is preferably introduced into the first reaction column in dissolved or suspended form together with the stream comprising the aromatic hydroxyl compound(s). Alternatively, the catalyst can also be metered in separately, for example, in an alcohol corresponding to the alcohol of reaction or a suitable inert solvent. In the case of use of heterogeneous catalysts, they can be used in a mixture with the random packings mentioned, in a suitable shape in place of random packings or as a bed on any column trays installed.

The energy required for the reaction in the first reaction column can firstly be generated by means of internal or external apparatus, for example heat exchangers, evaporators and/or heatable column trays, and/or secondly introduced either with the liquid stream comprising the aromatic hydroxyl compound(s) or with the stream which comprises dialkyl carbonate and is metered in gaseous form. Especially in the region of the reaction zone(s), heat can be supplied in this way. This heat is preferably supplied in the region of the reaction zone(s) fully or partly by means of evaporators or beatable column trays. It is particularly advantageous to introduce the energy required for the reaction in the first reaction column into the first reaction column at least partly either with the liquid stream comprising the aromatic hydroxyl compound(s) or with the stream which comprises dialkyl carbonate and is metered in gaseous form, and additionally by means of internal and/or external heat exchangers.

In the process according to the invention, the bottom product of the first reaction column is fed to a second reaction column.

The second reaction column comprises at least one rectifying section in the upper part of the column and at least one reaction zone below the rectifying section. The rectifying section has preferably 1 to 50 and more preferably 1 to 25 theoretical plates.

In the second reaction column, the bottom product of the first reaction column, which already comprises alkyl aryl carbonate and diaryl carbonate formed, is fed in liquid form or as a vapour-liquid mixture, preferably to the reaction zone, more preferably to the upper part of the reaction zone, most preferably in the upper third of the reaction zone. In this case, the second reaction column is preferably operated such that the alkyl aryl carbonate is converted partly or fully, for example by further transesterification or disproportionation, preferably by disproportionation, to the diaryl carbonate. In addition to the bottom product of the first reaction column, it is possible to meter in one or more streams comprising alkyl aryl carbonate in the region of the reaction zone in liquid form or as a vapour-liquid mixture. Such additional streams comprising alkyl aryl carbonate may originate, for example, from the further workup and be recycled thus into the process.

At the top of the second reaction column, unconverted aromatic hydroxyl compound, dialkyl carbonate, alcohol of reaction, medium-boiling secondary compounds—for example alkyl aryl ethers—and, to a minor degree, low-boiling secondary compounds are removed. In the context of the invention, medium-boiling secondary compounds are understood to mean those having a boiling point below that of the alkyl aryl carbonate and above that of the dialkyl carbonate. Such medium-boiling secondary compounds are, for example, alkyl aryl ethers, for example anisole or phenetol. The medium-boiling secondary compounds removed in the second reaction column may form in the reaction in the first and/or second reaction column or already have been introduced into the process through the reactants.

The rectifying section of the second reaction column serves to remove the higher-boiling components also evaporated in the reaction zone, for example alkyl aryl carbonate.

In preferred embodiments, the second reaction column is likewise operated under those reflux conditions described for the first reaction column.

The second reaction column may have at least one stripping section below a reaction zone. In preferred embodiments, the reaction zone of the second reaction column may, however, function simultaneously as a stripping section. In this case, the dialkyl carbonate released in the disproportionation is removed by transesterification of alcohol of reaction released and unconverted aromatic hydroxyl compound, and diaryl carbonate and the alkyl aryl carbonate which is depleted essentially through disproportionation are simultaneously concentrated.

The second reaction column may additionally preferably be equipped with one or more bottom evaporator(s).

Additionally preferably, the second reaction column may have, in the region of the stripping section and/or of the reaction zone, one or more intermediate heaters or intermediate evaporators.

In principle, the rectifying section of the second reaction column may likewise be equipped with one or more intermediate condensers. This divides the rectifying section into a lower rectifying section and an upper rectifying section (two sectors), of which the lower rectifying section is present below the intermediate condenser and the upper rectifying section above the intermediate condenser. In a preferred embodiment, the second reaction column does not have an intermediate condenser.

The second reaction column is equipped with one or more condensers. These are preferably one or more condensers at the top of the second reaction column (top condenser(s)). Particular preference is given to using a cascade of top condensers.

In the course of the condensation in the condenser(s) at the top of the second reaction column, the vapours become depleted in relatively high-boiling components, for example aromatic hydroxyl compound. In order to be able to particularly efficiently utilize the heat of condensation obtained for the purposes of thermal integration, the condensation is therefore preferably effected in several stages, more preferably at least two stages, and in preferred embodiments in two or three stages.

In the particularly preferred embodiment of two- or three-stage condensation, the heat of condensation of the first or of the first and second condensation stage is used directly or indirectly to heat a stream or a column within the process, while the heat of condensation obtained from the second or third condensation stage is removed by cooling water or air cooling.

The condensation at the top of the second reaction column can, in further preferred embodiments, additionally be carried out by not condensing a portion of the vapours withdrawn at the top of the second reaction column, in order to be able to selectively discharge medium-boiling secondary compounds.

Below the reaction zone and any stripping section present, a mixture comprising alkyl aryl carbonate, excess or unconverted aromatic hydroxyl compound, diaryl carbonate, transesterification catalyst(s), dialkyl carbonate, alcohol of reaction and medium- or high-boiling secondary compounds formed in the reaction or already present in the reactants is obtained. In the context of the invention, high-boiling secondary compounds are understood to mean those having a boiling point above that of the alkyl aryl carbonate. Such high-boiling secondary compounds can be divided into those whose boiling point is between that of the alkyl aryl carbonate and that of the diaryl carbonate (high boilers), and those whose boiling point is above the boiling point of the diaryl carbonate (very high boilers).

In all sections of the second reaction column, i.e. both in the rectifying section and any stripping section, and in the reaction zone, the random packings or structured packings already cited above for the first reaction column can be used.

The more exact design of the reaction zone(s), of any stripping section to be used and of the rectifying section(s) can be undertaken by the person skilled in the art.

The temperature of the reaction zone(s) is preferably in the range of 100 to 300° C., more preferably of 120 to 250° C., most preferably of 180 to 250° C.

In particular embodiments, an optimal reaction temperature is established in the reaction zone firstly through the selection of the operating conditions and secondly through additional supply of heat in the region of one or more reaction trays. The heat can be supplied to the reaction trays either by means of heat exchangers or via reaction trays with means of introducing heat. It is advantageous to carry out the inventive transesterification not only at standard pressure, but also under elevated or reduced pressure, preferably under reduced pressure. The pressure of the second reaction column is therefore preferably in the range of 0.05 to 20 bar (absolute), more preferably of 0.1 to 10 bar (absolute), most preferably of 0.1 to 2 bar (absolute).

For the reaction steps which occur in the second reaction column, the transesterification catalysts already cited above for the transesterification in the first reaction column can be used. In a preferred embodiment, identical catalysts are used in the first and second reaction columns.

The catalyst is preferably introduced into the second reaction column in dissolved or suspended form together with the bottom product of the first reaction column. Alternatively, the catalyst may also be metered in separately, for example, in an alcohol corresponding to the alcohol of reaction or a suitable inert solvent. In the case of use of heterogeneous catalysts, these can be used in a mixture with the random packings mentioned, in a suitable shape in place of random packings or as a bed on any column trays installed.

The energy required for the reaction in the second reaction column can firstly be generated by means of internal or external apparatus, for example heat exchangers, evaporators and/or heatable column trays, and/or secondly introduced either with the liquid stream comprising the aromatic hydroxyl compound(s). Preference is given to supplying this heat fully or partly by means of evaporators in the region of the reaction zone(s).

The second reaction column may be followed downstream by one or more further reaction columns. For such further reaction columns, the conditions and parameter ranges specified above for the second reaction column apply, although the conditions and parameters of further reaction columns need not be identical to those in the second reaction column, but preferably differ from those in the second reaction column within the aforementioned range of conditions and parameter ranges. Preference is given to operating a reaction column in addition to the second reaction column, for example, at a lower pressure than the second reaction column; reflux ratio and bottom temperature may also be modified compared to those in the second reaction column. In a preferred embodiment, in the process according to the invention, the first reaction column is followed downstream by only one further reaction column, i.e. the aforementioned second reaction column. The reaction columns may, however, be followed downstream by further columns for purification and separation of the components of the streams withdrawn. Such columns for purification and separation of the components are not understood to be reaction columns in the context of the invention, and are referred to as distillation columns.

The condensers with which at least one of the reaction column(s) selected from the first reaction column or the further reaction column(s) are equipped, and from which the heat of condensation obtained can be recycled directly or indirectly back into the process, may be either condensers at the top of the columns—also referred to hereinafter as top condensers—or condensers in the rectifying section of the columns—also referred to hereinafter as intermediate condensers.

In the process according to the invention, preference is given to equipping at least one rectifying section of the first reaction column with at least one intermediate condenser, and the heat of condensation obtained by condensation in this intermediate condenser is recycled directly or indirectly back into the process.

Additionally preferably, in the process according to the invention, the reaction column or at least one of the further reaction column(s) is equipped with one or more condensers at the top of the reaction column(s), and the heat of condensation obtained by condensation in these condensers is recycled directly or indirectly back into the process.

The heat of condensation obtained by condensation in the condenser(s), preferably top condenser(s) of the second reaction column or the further reaction column(s), preferably of the second reaction column, is, according to the invention, recycled directly or indirectly, fully or partly, back into the process. In the case that the first reaction column is equipped with one or more intermediate condensers, the heat of condensation obtained by condensation in the intermediate condenser(s) is, according to the invention, likewise recycled directly or indirectly, fully or partly, back into the process. In the context of the invention, direct recycling of the heat of condensation into the process is understood to mean that this heat of condensation is recycled into the process without an intermediate heating medium, for example to heat either one or more streams or to heat one or more column sections within the process. This can be done, for example, in a heat exchanger. In this case, preference is given to combining either one such heat exchanger with the condenser(s). Indirect recycling of the heat of condensation into the process is understood in the context of the invention to mean that the heat of condensation obtained is first used to generate a heating medium which serves to recycle the heat of condensation into the process. This heating medium can be used, for example, to heat one or more streams or one or more column sections within the process. Useful heating media include gases, vapours or liquids, preferably vaporous or liquid technical heat carrier media, for example water, heat carriers based on mineral oil or synthetic heat carriers (e.g. Diphyl™, Marlotherm®). Particularly preferred heating media are water or water vapour.

Particular preference is given to using the heat of condensation obtained by condensation in the condenser(s), preferably top condenser(s), of the further reaction column(s) and/or any intermediate condenser(s) present in the first reaction column directly or indirectly, fully or partly, to separate the dialkyl carbonate from the alkyl alcohol formed during the reaction and/or to evaporate the dialkyl carbonate introduced into the first reaction column. Very particular preference is given to using the heat of condensation obtained by condensation in the condenser(s), preferably top condenser(s), the further reaction column(s) and/or any intermediate condenser(s) present in the first reaction column directly or indirectly, partly to separate the dialkyl carbonate from the alkyl alcohol formed during the reaction and partly to evaporate the dialkyl carbonate introduced into the first reaction column. In preferred embodiments of the process according to the invention, the heat of condensation obtained by condensation in the condenser(s) of the further reaction column(s) is used directly or indirectly, fully or partly, to separate the dialkyl carbonate from the alkyl alcohol formed during the reaction, and the heat of condensation obtained by condensation in the intermediate condenser(s) of the first reaction column is used directly or indirectly, fully or partly, to evaporate the dialkyl carbonate introduced into the first reaction column.

In the process according to the invention, in the course of transesterification and/or disproportionation in the first reaction column and/or the further reaction column(s), streams comprising alkyl alcohol formed during the reaction (alcohol of reaction) and dialkyl carbonate unconverted or formed during the reaction are obtained and are preferably withdrawn in a mixture in one or more streams. This dialkyl carbonate unconverted in the reaction columns or formed during the reaction is, according to the invention, separated fully or partly in at least one further process step comprising at least one distillation column from the alkyl alcohol formed during the reaction (alcohol of reaction). Preference is given to withdrawing at least one stream comprising dialkyl carbonate unconverted or formed during the reaction and alkyl alcohol formed during the reaction at the top of the first reaction column and separating it by feeding it to at least one further process step comprising at least one distillation column.

Preference is given to feeding the vapour mixture which is withdrawn at the top of the first reaction column and comprises dialkyl carbonate and alkyl alcohol formed during the reaction, after condensation at the top of the first reaction column, fully or partly to at least one further process step comprising at least one distillation column, for separation of dialkyl carbonate and alkyl alcohol—referred to hereinafter as separating distillation column(s). Particular preference is given to feeding the dialkyl carbonate removed, optionally after further purification, back to the first reaction column.

The dialkyl carbonate and the alcohol of reaction are preferably separated by distillation in one or more separating distillation columns or in a combination of distillation and membrane separation—referred to hereinafter as a hybrid process.

When alcohol of reaction and dialkyl carbonate form an azeotrope (e.g. methanol and dimethyl carbonate), preference is given to using an at least two-stage process, for example a two-pressure process, an extractive distillation, a heteroazeotrope distillation with a low-boiling azeotroping agent, or a hybrid process. Particular preference is given to employing the two-pressure process or a hybrid process. Very particular preference is given to employing the two-pressure process. Such processes are known in principle to those skilled in the art (cf., for example, Ullmann's Encyclopedia of Industrial Chemistry, Vol. 7, 2007, Ch. 6.4. and 6.5; Chemie Ingenieur Technik (67) 11/95).

When alcohol of reaction and dialkyl carbonate do not form an azeotrope (e.g. ethanol and diethyl carbonate), the separation is preferably effected in a single separating distillation column.

When alcohol of reaction and dialkyl carbonate form an azeotrope, the distillate of a first separating distillation column of the process step for separating dialkyl carbonate and alkyl alcohol (alcohol of reaction) preferably has virtually azeotropic composition. In this case, it is preferably fed, in a two-pressure process, to at least one further separating distillation column which operates at an operating pressure below that of the first separating distillation column. By virtue of the different operating pressure, the position of the azeotrope shifts toward lower proportions of alcohol of reaction. The bottom product obtained from this second separating distillation column or these further separating distillation column(s) is alcohol of reaction in a purity of 90 to 100% by weight, based on the total weight of the isolated bottom product, and the distillate obtained is a virtually azeotropic mixture. The second separating distillation column or further separating distillation column(s) which work at lower operating pressure is/are, in very particularly preferred embodiments, preferably operated with the heat of condensation of the top condenser(s) of the first separating distillation column.

The two-pressure process makes use of the pressure dependence of the azeotropic composition of a two-substance mixture. In the case of a mixture of alcohol of reaction (alkyl alcohol) and dialkyl carbonate, for example methanol and dimethyl carbonate, the azeotropic composition shifts to a higher alcohol of reaction contents with increasing pressure. When a mixture of these two components is fed to a first separating distillation column (dialkyl carbonate column), the alcohol of reaction content being below the corresponding azeotropic composition for the operating pressure of this column, the distillate obtained is a mixture with virtually azeotropic composition and the bottom product virtually pure dialkyl carbonate. The azeotropic mixture thus obtained is fed to a further separating distillation column (alkyl alcohol column). This works at a lower operating pressure compared to the dialkyl carbonate column. As a result, the position of the azeotrope is shifted toward lower alcohol of reaction contents. This makes it possible to separate the azeotropic mixture obtained in the dialkyl carbonate column into a distillate with virtually azeotropic composition and virtually pure alcohol of reaction. The distillate of the alkyl alcohol column is fed back to the dialkyl carbonate column at a suitable point.

The operating pressure of the alkyl alcohol column is preferably selected such that it can be operated with the waste heat of the dialkyl carbonate column. The operating pressure is between 0.1 and 2 bar, preferably between 0.3 and 1 bar. The operating pressure of the dialkyl carbonate column is in the range of 1 to 50 bar, preferably between 2 and 20 bar.

An illustrative reaction regime in the separation of dialkyl carbonate and alcohol of reaction by the two-pressure process is shown in FIG. 1.

A further preferred process for separating azeotropes of alcohol of reaction and dialkyl carbonate is the hybrid process. In the hybrid process, a two-substance mixture is separated by means of a combination of distillation and a membrane process. This makes use of the fact that the components, owing to their polar properties and their different molecular weight, can be at least partly separated from one another by means of membranes. In the case of a mixture of alcohol of reaction and dialkyl carbonate, for example methanol and dimethyl carbonate, when suitable membranes are used, by means of pervaporation or vapour permeation, a mixture rich in alcohol of reaction is obtained as the permeate and a mixture depleted in alcohol of reaction as the retentate. When a mixture of these two components is fed to a separating distillation column (dialkyl carbonate column), the content of alcohol of reaction being below the corresponding azeotropic composition for the operating pressure of this column, the distillate obtained is a mixture with a significantly increased alcohol of reaction content compared to the feed, and the bottom product virtually pure dialkyl carbonate.

In the case of a hybrid process composed of distillation and vapour permeation, the distillate is withdrawn from the column in vaporous form. The vaporous mixture thus obtained is optionally fed to a vapour permeation after superheating. This vapour permeation is conducted in such a way that approximately the operating pressure of the column is established on the retentate side and a lower pressure on the permeate side. The operating pressure of the column is in the range of 1 to 50 bar, preferably between 1 and 20 and more preferably between 2 and 10 bar. The pressure on the permeate side is between 0.05 and 2 bar. This affords, on the permeate side, a fraction rich in alcohol of reaction with a content of alcohol of reaction of at least 70% by weight, preferably at least 90% by weight, based on the total weight of the fraction. The retentate, which contains a reduced content of alcohol of reaction compared to the distillate of the column, is optionally condensed and fed back to the distillation column.

In the case of a hybrid process composed of distillation and pervaporation, the distillate is withdrawn from the column in liquid form. The mixture thus obtained is, optionally after heating, fed to a pervaporation. This is conducted in such a way that an identical or elevated operating pressure compared to the column is established on the retentate side, and a lower pressure on the permeate side. The operating pressure in the column is 1 to 50 bar, preferably between 1 and 20 and more preferably between 2 and 10 bar. The pressure on the permeate side is between 0.05 and 2 bar. This affords, on the permeate side, a vaporous fraction rich in alcohol of reaction with a content of alcohol of reaction of at least 70% by weight, preferably at least 90% by weight, based on the total weight of the fraction. The liquid retentate, which obtains a reduced content of alcohol of reaction compared to the distillate of the column, is fed back to the separating distillation column. The evaporation of the permeate requires heat, which may not be present to a sufficient degree in the feed stream to the prevaporation. A membrane separation by means of pervaporation may therefore optionally be heated with additional heat exchangers, which are integrated or optionally inserted between a plurality of pervaporation steps connected in series.

In the case of a hybrid process, dialkyl carbonate and alcohol of reaction are more preferably separated by means of a combination of distillation and vapour permeation.

Figure 3:
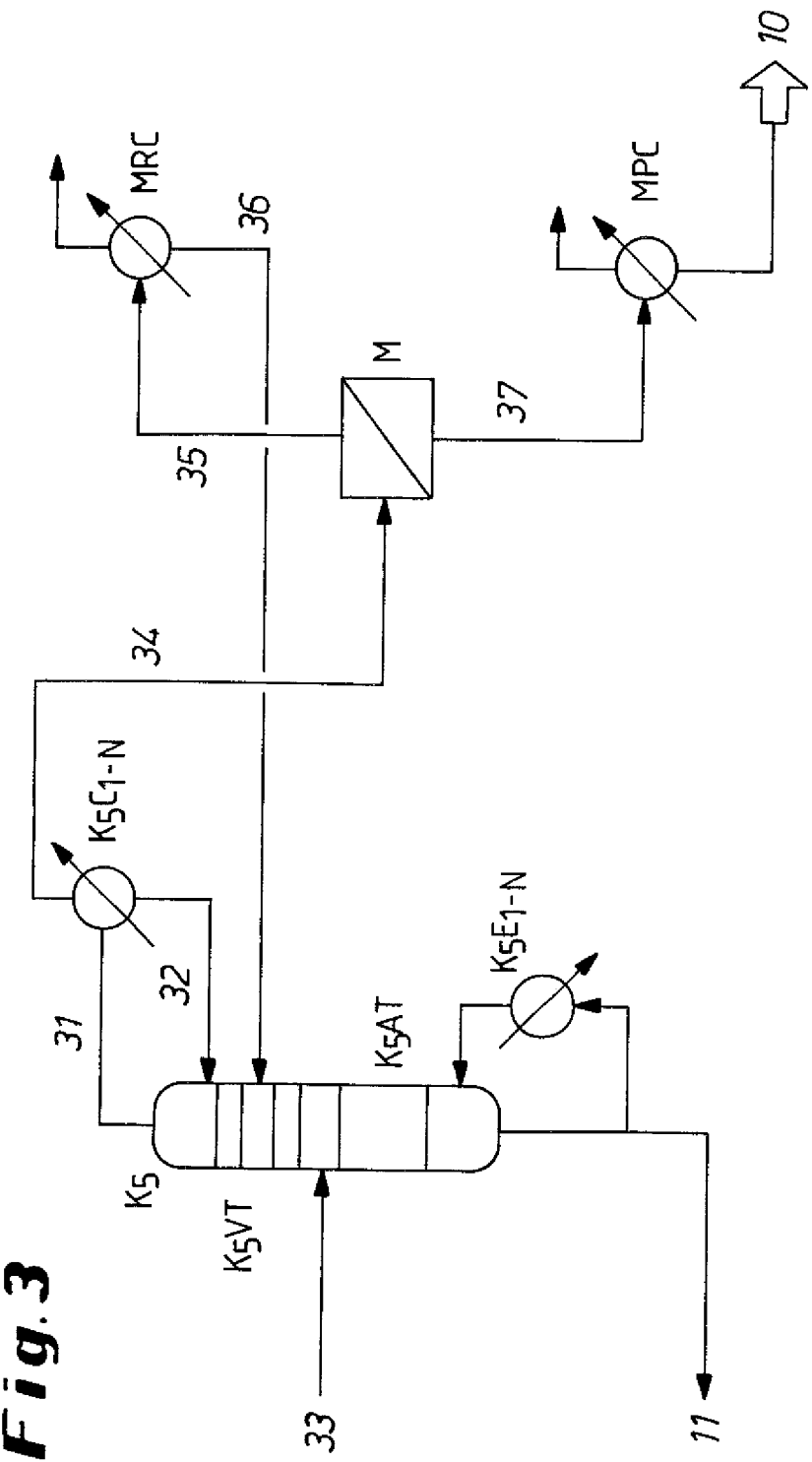

An illustrative embodiment of the separation of dialkyl carbonate and alcohol of reaction by the hybrid process by means of vapour permeation is shown in FIG. 3.

Irrespective of the process selected to separate dialkyl carbonate and alcohol of reaction, the process conditions, such as pressure and temperature, are advantageously selected such that the heat of condensation obtained by condensation in the condenser(s) of the further reaction column(s) and/or any intermediate condenser(s) present in the first reaction column can be utilized effectively.

To this end, the operating pressure and hence also the operating temperature in the separating distillation column(s) of the process step for separation of dialkyl carbonate and alkyl alcohol are adjusted such that the separating distillation column(s) can be operated fully or partly with the heat of condensation in the condenser(s) of the further reaction column(s) and/or any intermediate condenser(s) present in the first reaction column. To this end, the operating pressure in the separating distillation column(s) of the process step for separation of dialkyl carbonate and alkyl alcohol is preferably adjusted such that the evaporation temperature in the bottom of the separating distillation column(s) of the process step for separation of dialkyl carbonate and alkyl alcohol is below the condensation temperature in the condenser(s) of the further reaction column(s) and/or any intermediate condenser(s) present in the first reaction column.

The heat required to separate alcohol of reaction and dialkyl carbonate is supplied at a temperature between 100 and 300° C., preferably between 100 and 230° C. and more preferably between 120 and 200° C. In order to efficiently enable thermal integration with the intermediate condenser of the first reaction column or the condensers of the second reaction column, the condensation in the condenser(s) of the further reaction column(s) and/or any intermediate condenser(s) present in the first reaction column is carried out at a temperature elevated by 1 to 100° C., preferably 2 to 50° C. and more preferably 5 to 40° C.

The heat of condensation from the condenser(s) of the further reaction column(s) and/or any intermediate condenser(s) present in the first reaction column can, for example, be used fully or partly to preheat feed streams to the separating distillation column(s) and/or to heat one or more column sections. In preferred embodiments, the heat of condensation from the condenser(s) of the further reaction column(s) and/or any intermediate condenser(s) present in the first reaction column is used partly to preheat the feed stream(s) to the separating distillation column(s) of the process step for separation of dialkyl carbonate and alkyl alcohol, and partly for evaporating the bottoms in the separating distillation column(s). In a very preferred embodiment of the process according to the invention, in which a cascade of at least two, preferably three, top condensers is used at the top of the second reaction column, the heat of condensation from the first condenser of this cascade serves to evaporate the bottom product of the separating distillation column or of the first separating distillation column of the process step for separation of dialkyl carbonate and alkyl alcohol, and the heat of condensation from the second condenser of the cascade serves to preheat the feed stream to the separating distillation column or the first separating distillation column of the process step for separation of dialkyl carbonate and alkyl alcohol.

The separating distillation column(s) preferably possess (es) a rectifying section having 5 to 40 theoretical plates for concentration of the alcohol of reaction and a stripping section having 5 to 40 theoretical plates for concentration of the dialkyl carbonate.

The utilization of the heat of condensation from the condenser(s) of the further reaction column(s) and if appropriate the intermediate condenser(s) of the first reaction column allows the separation of the alcohol of reaction from excess dialkyl carbonate to be carried out with significantly reduced energy consumption. The cooling performance in the transesterification steps can be reduced to the same degree. A significant advantage of the process according to the invention over the prior art processes therefore lies in the significant reduction of the energy consumption in the preparation of diaryl carbonates and/or alkyl aryl carbonates. At the same time, the process can be performed with simple apparatus, since, owing to the use of column arrangements, no complicated reactor arrangement with a plurality of separate reaction zones connected in series is required.

According to the invention, the bottom product which comprises diaryl carbonate and is obtained in the further reaction column(s) from step (b) is fed to at least one further process step for purification in at least one distillation column—also referred to hereinafter as first diaryl carbonate distillation column—comprising at least one rectifying section in the upper part of the column and at least one stripping section in the lower part of the column. A diaryl carbonate-containing sidestream is preferably withdrawn from this first diaryl carbonate distillation column. Additionally preferably, the bottom product which comprises diaryl carbonate and is obtained in the further reaction column(s) from step (b) comprises compounds having a boiling point between that of the diaryl carbonate and that of the alkyl aryl carbonate formed as an intermediate during the preparation of the diaryl carbonate as an impurity, which are withdrawn from the diaryl carbonate distillation column in a further sidestream and optionally recycled into the reaction column or one of the further reaction column(s) from step (b).

Preferably, the bottom product obtained from step (b) in the further reaction column(s)—also referred to as crude diaryl carbonate—contains 10 to 90% by weight, more preferably 20 to 80% by weight and most preferably 40 to 80% by weight of diaryl carbonate, and 5 to 90% by weight, more preferably 5 to 60% by weight and most preferably 5 to 40% by weight of alkyl aryl carbonate, 1 to 90% by weight, more preferably 1 to 50% by weight and most preferably 1 to 30% by weight of aromatic hydroxyl compound, 0 to 5% by weight, more preferably 0 to 2% by weight and most preferably 0 to 0.5% by weight of high-boiling secondary components, 0 to 5% by weight, more preferably 0.0001 to 2% by weight and most preferably 0.0001 to 1% by weight of medium-boiling secondary components, and 0.01 to 10% by weight, more preferably 0.1 to 5% by weight and most preferably 1 to 5% by weight of catalyst, where the sum of all aforementioned components in the diaryl carbonate to be purified adds up to 100% by weight. The percentages by weight are each based on the total weight of the crude diaryl carbonate to be purified.

By the process according to the invention, it is preferably possible to obtain diaryl carbonates having a purity of, i.e. a content of pure diaryl carbonate of, 99 to 100% by weight, more preferably 99.5 to 100% by weight and most preferably 99.9 to 100% by weight, based on the total weight of the purified diaryl carbonate.

The diaryl carbonate withdrawn in the sidestream of the first diaryl carbonate distillation column can be withdrawn in liquid or vaporous form. The diaryl carbonate withdrawn in the sidestream of the first diaryl carbonate distillation column is preferably withdrawn in vaporous form. In preferred embodiments, however, liquid withdrawal of the diaryl carbonate in the sidestream may be preferred, more particularly owing to construction reasons.

The first diaryl carbonate distillation column has at least two sectors, i.e. a rectifying section in the upper part of the column and a stripping section in the lower part of the column. The rectifying section of the first diaryl carbonate distillation column can preferably be divided into a lower rectifying section and an upper rectifying section. Additionally preferably, the stripping section of the first diaryl carbonate distillation column can be divided into a lower stripping section and an upper stripping section.

In a preferred embodiment of the process according to the invention, the purification of the bottom product which comprises diaryl carbonate and is obtained in the reaction column or the further reaction column(s) from step (b) is carried out in at least one diaryl carbonate distillation column which has at least three sectors. These at least three sectors are at least one rectifying section and at least one stripping section, said stripping section being divided into a lower stripping section and an upper stripping section. More preferably, the first diaryl carbonate distillation column with a rectifying section and a stripping section, the stripping section being divided into a lower stripping section and an upper stripping section, has four sectors, the rectifying section also being divided into a lower rectifying section and an upper rectifying section.

Overall, the first diaryl carbonate distillation column preferably has an overall separating performance of 3 to 160, more preferably of 10 to 90 and most preferably of 13 to 50 theoretical plates. The upper rectifying section preferably has a separating performance of 0 to 40, more preferably 1 to 20 and most preferably 1 to 10 theoretical plates, the lower rectifying section preferably 1 to 40, more preferably 5 to 20 and most preferably 5 to 15 theoretical plates, the upper stripping section preferably 1 to 40, more preferably 2 to 30 and most preferably 5 to 20 theoretical plates, and the lower stripping section preferably 1 to 40, more preferably 2 to 20 and most preferably 2 to 15 theoretical plates.

The evaporation is effected preferably in a temperature range of 100 to 300° C., preferably of 150 to 240° C. and more preferably of 180 to 230° C. in the bottom of the column. The condensation of the vapours at the top of the column can be effected in one or more stages, preferably one or two stages, in a temperature range of preferably 40 to 250° C., preferably 50 to 200° C. and more preferably 60 to 180° C.

The first diaryl carbonate distillation column is preferably operated at a top pressure of 1 to 1000 mbar (absolute), more preferably of 1 to 100 mbar (absolute) and most preferably of 5 to 50 mbar (absolute). The reflux ratio is preferably 0.1 to 10, more preferably 0.5 to 5 and most preferably 0.5 to 2.

In preferred embodiments of the process according to the invention, the first diaryl carbonate distillation column may be a dividing wall column.

Dividing wall columns are likewise suitable for separating a mixture into three fractions, i.e. top product, bottom product and sidestream with high purity. The dividing wall column possesses a generally vertical dividing wall which separates the feed side from the withdrawal side for the sidestream. The dividing wall is preferably not continuous over the entire length of the column. Usually, there is also a rectifying section above the dividing wall and a stripping section below the dividing wall. In the region of the dividing wall, both on the feed side and on the withdrawal side for the sidestream, there are preferably at least two sectors. On the feed side, an upper sector serves to reduce the high boilers present in the feed and a lower sector to reduce the low boilers present in the feed. On the withdrawal side for the sidestream, there is likewise an upper sector above the withdrawal point, which serves to reduce the low boilers from the rectifying section. A lower sector which is arranged below the withdrawal point serves to reduce high boilers which come from the stripping section below the dividing wall.

The division of the liquid effluxing from the rectifying section is guided by the requirements on the specific separation task and can be influenced by both construction and control technology measures. The same applies to the vapour stream coming from the stripping section.

Dividing wall columns are known to those skilled in the art and are described, for example, in DE-A 33 02 525 or DE-A 199 14 966.

The dividing wall column preferably has, in addition to at least one rectifying section in the upper part of the column and at least one stripping section in the lower part of the column, in each case an upper and lower sector on the feed side of the dividing wall and on the withdrawal side of the dividing wall, feed and withdrawal each being effected between the upper and lower sector.

In particularly preferred embodiments of the process according to the invention, the rectifying section of the dividing wall column has two sectors, i.e. a lower rectifying section and an upper rectifying section.

In very particularly preferred embodiments of the process according to the invention, the dividing wall column has at least seven sectors, comprising at least one stripping section in the lower part of the column, in each case an upper and lower sector on the feed side of the dividing wall and on the withdrawal side of the dividing wall, and an upper and lower rectifying section in the upper part of the column.

The dividing wall in such a dividing wall column is preferably arranged in longitudinal direction of the column. It prevents both vaporous and liquid mass transfer between the feed side and withdrawal side.

The purified diaryl carbonate can be withdrawn on the withdrawal side of the dividing wall in liquid or vaporous form. In the column design, the type of withdrawal can in some cases significantly influence the arrangement of the dividing wall within the column. The dividing wall may be arranged within the column shifted to the withdrawal side or to the feed side in each case, and thus decrease or increase the cross section of the particular side compared to the other. In the case of vaporous withdrawal of the purified diaryl carbonate on the withdrawal side of the dividing wall, the cross section of the withdrawal side of the column is preferably greater than the cross section of the feed side, i.e. more vapour passes from the stripping section into the withdrawal side. In the case of liquid withdrawal of the purified diaryl carbonate on the withdrawal side of the dividing wall, the cross section of the feed side of the column is preferably identical to the cross section of the withdrawal side.

The upper rectifying section of such a dividing wall column preferably has a separating performance of 0 to 40, more preferably 1 to 20 and most preferably 1 to 10 theoretical plates, the lower rectifying section preferably 1 to 40, more preferably 5 to 20 and most preferably 5 to 15 theoretical plates, the stripping section preferably 1 to 40, more preferably 2 to 20 and most preferably 2 to 15 theoretical plates. The upper sector and lower sector on the feed side of the dividing wall and the upper sector and lower sector on the withdrawal side of the dividing wall preferably each have a separating performance of 1 to 40, more preferably 2 to 20 and most preferably 5 to 20 theoretical plates.

The bottom product of the first diaryl carbonate distillation column has a residue content of diaryl carbonate of less than 95% by weight, preferably less than 90% by weight and more preferably less than 75% by weight.

To prevent catalyst losses, the bottom product of the first diaryl carbonate distillation column can be recycled fully or partly, preferably to an extent of at least 50% by weight, more preferably to an extent of at least 80% by weight and most preferably to an extent of at least 90% by weight, back into the transesterification from at least one dialkyl carbonate and at least one aromatic hydroxyl compound. The remaining portion of the bottom product of the first diaryl carbonate distillation column can be fed to a workup stage, referred to hereinafter as residue concentration, for the purpose of concentrating the residue and partially recovering the diaryl carbonate still present in the bottom product of the first diaryl carbonate distillation column. The diaryl carbonate recovered in the residue concentration can, in a particular embodiment of the process, be fed in liquid or vaporous form, preferably in vaporous form, back to the first diaryl carbonate distillation column. The concentrated residue from the residue concentration can either be discharged from the process or sent to a further workup stage for the purpose of recovering the catalyst. It is therefore possible with preference to obtain, from the bottom product of at least one diaryl carbonate distillation column from process stage (e), a catalyst-containing stream which is recycled fully or partly, optionally after further purification, back into the process, preferably into process step (a). This allows both losses of expensive catalysts and losses of desired diaryl carbonate to be avoided and hence the process according to the invention additionally to be configured more economically viably.

In a preferred embodiment of the process according to the invention,
(f) a catalyst-containing stream is obtained from the bottom product of at least one diaryl carbonate distillation column from process step (e) and is recycled fully or partly, optionally after further purification, back into the process, preferably into process step (a),
(g) a stream comprising aromatic hydroxyl compound(s) and alkyl aryl carbonate is obtained from at least one diaryl carbonate distillation column from process step (e) and is recycled fully or partly back into the process, preferably into process step (a) or (b), and
(h) compounds having a boiling point above the boiling point of the diaryl carbonate and compounds whose boiling point is between that of the dialkyl carbonate and that of the alkyl aryl carbonate formed during the preparation of the diaryl carbonate are discharged fully or partly from the process together or separately from one another from at least one diaryl carbonate distillation column from process step (e).

The discharge described under (h) can preferably be effected as a liquid sidestream from the rectifying section of at least one diaryl carbonate distillation column and/or of a substream of the distillate of this column.

According to the invention, the vapour which comprises aromatic hydroxyl compound(s) and is withdrawn at the top of at least one reaction column from (b), if appropriate after condensation in at least one condenser, is fed fully or partly to at least one further process step comprising at least one distillation column, which removes compounds whose boiling point is between that of the dialkyl carbonate and that of the alkyl aryl carbonate formed during the preparation of the diaryl carbonate—also referred to hereinafter as medium-boiling secondary compounds. The distillation column(s) used in this process step for removal of compounds whose boiling point is between that of the dialkyl carbonate and that of the alkyl aryl carbonate formed during the preparation of the diaryl carbonate are also referred to hereinafter as intermediate boiler distillation columns.

In a preferred embodiment of the process according to the invention, the vapour which comprises aromatic hydroxyl compound(s) and is withdrawn at the top of at least one reaction column from (b), if appropriate after condensation in at least one condenser, is fed to at least one further process step comprising at least two intermediate boiler distillation columns, the bottom product of the first intermediate boiler distillation column being fed to a second intermediate boiler distillation column.

Preferably, the aromatic hydroxyl compound(s) obtained from the process step(s) for removal of compounds whose boiling point is between that of the dialkyl carbonate and that of the alkyl aryl carbonate formed during the preparation of the diaryl carbonate from the vapour which comprises aromatic hydroxyl compound(s) and is withdrawn fully or partly at the top of at least one reaction column from (b), optionally after condensation in at least one condenser, is/are fed back to the first reaction column. The aromatic hydroxyl compound(s) obtained after the removal is/are preferably withdrawn from a first and only intermediate boiler distillation column as a bottom product, or from a second or further intermediate boiler distillation column as a sidestream or bottom product.

Preferably, the product withdrawn at the top of the first intermediate boiler distillation column comprises dialkyl carbonate and is fed fully or partly to process step (c) comprising at least one separating distillation column for removal of the alkyl alcohol.

Figure 6:
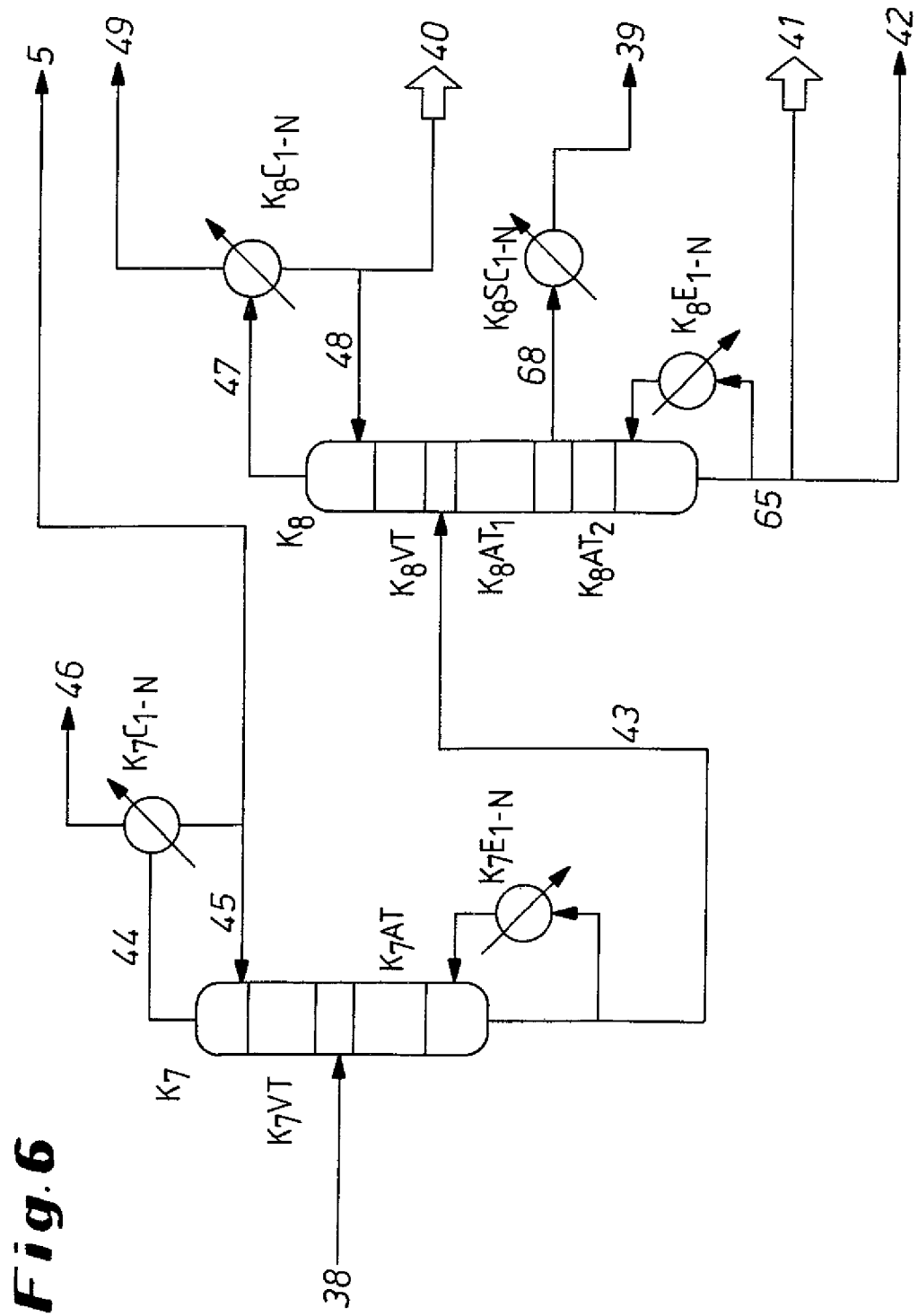

In a preferred embodiment, in the first intermediate boiler distillation column(s), alcohol of reaction, dialkyl carbonate and optionally a portion of the medium-boiling secondary components are removed as the top product (cf., for example, FIG. 6). In this case, this column preferably possesses a rectifying section having 5 to 40 theoretical plates for concentration of the alcohol of reaction and of the dialkyl carbonate, and a stripping section having 5 to 40 theoretical plates for concentration of the medium-boiling secondary compounds. The operating pressure is preferably between 0.05 and 3 bar absolute, more preferably between 0.1 and 2 bar absolute and most preferably between 0.5 and 1.5 bar absolute. The reflux ratio is preferably 0.1 to 10, more preferably 0.5 to 5 and most preferably 0.5 to 2.

In the case of the abovementioned preferred embodiment of the first intermediate boiler distillation column, the aromatic hydroxyl compound is withdrawn as a bottom product or sidestream, more preferably as a sidestream, medium-boiling secondary compounds having a boiling point above the aromatic hydroxyl compound at the bottom, and medium-boiling secondary compounds having a boiling point below the aromatic hydroxyl compound as the distillate. In the case of this preferred embodiment, the column preferably possesses a rectifying section having at least one sector and a separating performance of 5 to 40 theoretical plates, a stripping section having preferably at least one sector, more preferably having at least two sectors, with a separating performance of 5 to 60 theoretical plates. The operating pressure is preferably between 0.05 and 3 bar absolute, more preferably between 0.1 and 2 bar absolute and most preferably between 0.5 and 1.5 bar absolute. The reflux ratio is preferably 1 to 1000, more preferably 10 to 500 and most preferably 50 to 200.

In the case of a particularly preferred embodiment of the second intermediate boiler distillation column, the aromatic hydroxyl compound is withdrawn as a vaporous sidestream. The heat obtained in the condensation of the vaporous sidestream can be utilized either to generate a heat carrier medium or directly to heat other process steps for preparation of diaryl carbonates.

Figure 12:
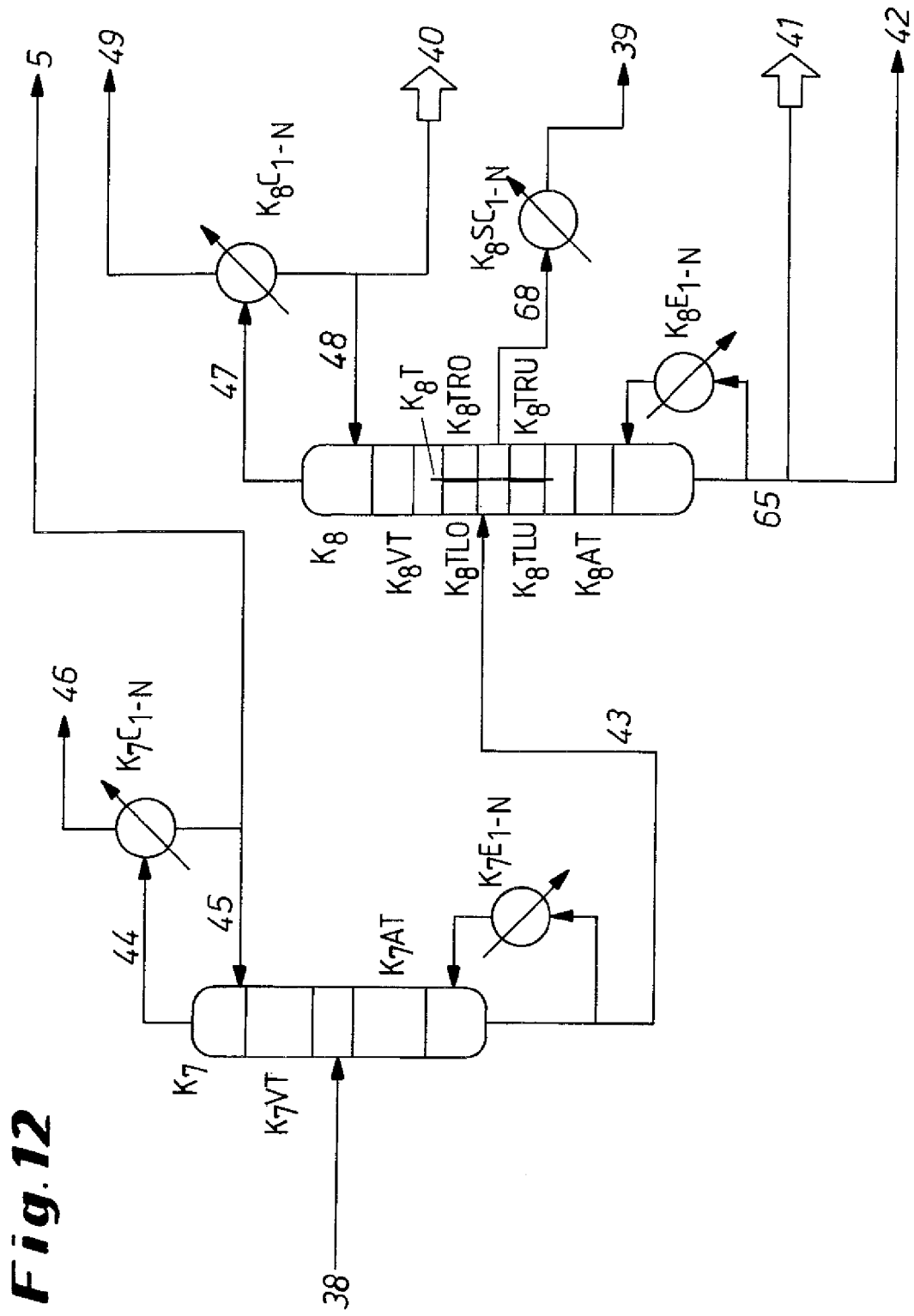

In a further preferred embodiment, the aromatic hydroxyl compound is removed in the second intermediate boiler distillation column with a dividing wall column (cf., for example, FIG. 12). In the case of such an embodiment of the process according to the invention, the dividing wall column preferably has at least 6 sectors, comprising at least one stripping section in the lower part of the column, in each case an upper and lower sector on the feed side of the dividing wall and on the withdrawal side of the dividing wall, and a rectifying section in the upper part of the column. The sectors preferably have a separating performance of 5 to 40 plates, and the sectors may each be different with regard to their separating performance.

The dividing wall in such a dividing wall column is preferably arranged in longitudinal direction of the column. It prevents both vaporous and liquid mass transfer between the feed side and withdrawal side.

When dialkyl carbonate and aromatic hydroxyl compound form a maximum azeotrope, a different separating sequence may be advantageous for the removal of the medium-boiling secondary compounds. In such a further embodiment of the first intermediate boiler distillation column, alcohol of reaction, dialkyl carbonate and medium-boiling secondary compounds are withdrawn as distillate, and an azeotropic mixture of dialkyl carbonate and aromatic hydroxyl compound as the bottom product.

In the case of this embodiment, the first intermediate boiler distillation column preferably possesses a rectifying section with at least one sector and a separating performance of 5 to 40 theoretical plates, a stripping section with at least one sector and a separating performance of 5 to 40 theoretical plates. The operating pressure is preferably between 0.05 and 3 bar absolute, more preferably between 0.1 and 2 bar absolute and most preferably between 0.1 and 1.5 bar absolute. The reflux ratio is preferably 0.1 to 10, preferentially 0.2 to 5 and more preferably between 0.4 and 2.

In the case of a removal of dialkyl carbonate, alcohol of reaction and medium-boiling secondary compounds as a distillate of the first intermediate boiler distillation column, the medium-boiling secondary compounds are preferably removed in a second intermediate boiler distillation column as the bottom product. In this case, the distillate obtained from the second intermediate boiler distillation column is a mixture of alcohol of reaction and dialkyl carbonate. In the case of this embodiment, the second intermediate boiler distillation column preferably likewise possesses of a rectifying section with at least one sector and a separating performance of 5 to 40 theoretical plates, a stripping section with at least one sector and a separating performance of 5 to 40 theoretical plates. The operating pressure is preferably between 0.05 and 10 bar absolute, more preferably between 0.05 and 2 bar absolute and most preferably between 0.08 and 1 bar absolute. The reflux ratio is preferably 0.1 to 10, preferentially 0.2 to 5 and more preferably between 0.4 and 2.

In preferred embodiments of the process according to the invention, at least one of the reaction columns used in the process and/or at least one of the distillation columns used in the process may have one or more top condensers which are integrated into the column, where the d/D ratio of diameter of the vapour line from the column to the top condenser(s) (d) to column diameter of the column (D) is in the range of 0.2 to 1, preferably in the range of 0.5 to 1. In a particularly preferred embodiment, the top condenser may be integrated into the distillation column, such that no vapour line is required between distillation column and top condenser. The d/D ratio in this case is 1. In this case, the column cross section after entry into the top condenser can also be adjusted to the progress of condensation under some circumstances. Such preferred embodiments are shown section by section and in a manner illustrative of a diaryl carbonate distillation column in FIGS. 5a and 5b. Corresponding arrangements are also possible for the other distillation columns and/or reaction columns used in the process. Preferably, a plurality of the reaction columns and/or distillation columns used in the process have one of the aforementioned top condensers.

Figure 5A:
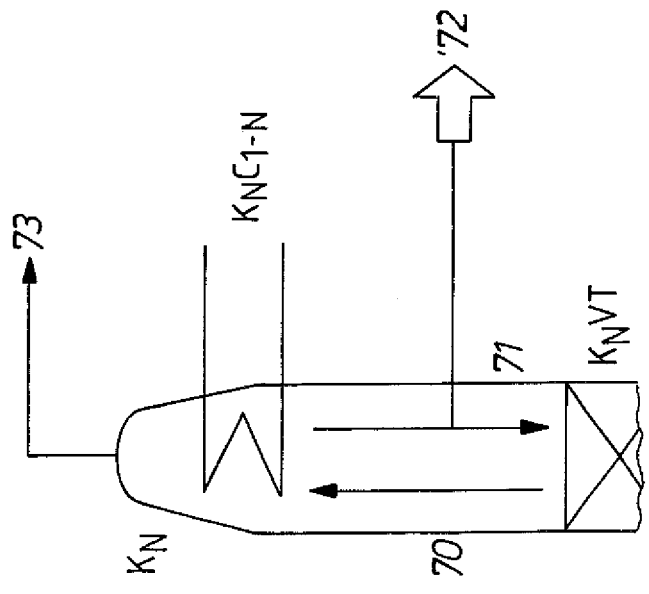

In the embodiment shown in FIG. 5a, the column diameter remains unchanged in the region of the condensation. The vapours (70) which ascend out of the rectifying section, if present preferably the upper rectifying section $K_N VT$, are condensed in the integrated top condenser(s) $K_N C_{1-N}$. A portion of the condensate is introduced as reflux (71) back to the upper column sector. The remaining portion of the condensate is discharged from the column as distillate (72). Inert and/or uncondensed vapours (73) are withdrawn at the top of the column.

In some condenser types, it may be advantageous to configure the column cross section variably. When the vapours to be condensed are guided, for example, from the bottom upward, the amount of vapour decreases in the upward direction. A reduction in the column diameter in the direction of the top of the column allows the column cross section available for the vapour to be adjusted to the amount of vapour which decreases in the upward direction. Such an embodiment is shown by way of example in FIG. 5b. In this case, the uncondensed vapours need not necessarily be withdrawn at the top. When, for example, a construction in which a plate bundle or tube bundle is inserted into the column from the top is selected, the withdrawal point of the uncondensed vapours may also be at the side.

In preferred embodiments of the process according to the invention, lines and units which conduct mixtures having a melting point of more than 30° C., preferably more than 40° C., may be heated to temperatures above this melting point, preferably to temperatures of more than 1° C. above this melting point, more preferably to temperatures of more than 5° C. above this melting point. This prevents precipitation of solids within these lines and units and considerably eases the restart of the corresponding systems after shutdowns.

The process according to the invention is preferably performed continuously.

The process according to the invention is described by way of example with reference to FIGS. 1 to 14.

FIG. 1 describes a first transesterification step by means of reactive rectification in a first reaction column with an intermediate condenser in general, a second reaction step for transesterification or for disproportionation of alkyl aryl carbonate in a second reaction column and a separation of the mixture which comprises dialkyl carbonate and alcohol of reaction and is obtained as the top product in the first reaction column in a further process step comprising at least one separating distillation column.

Figure 2:
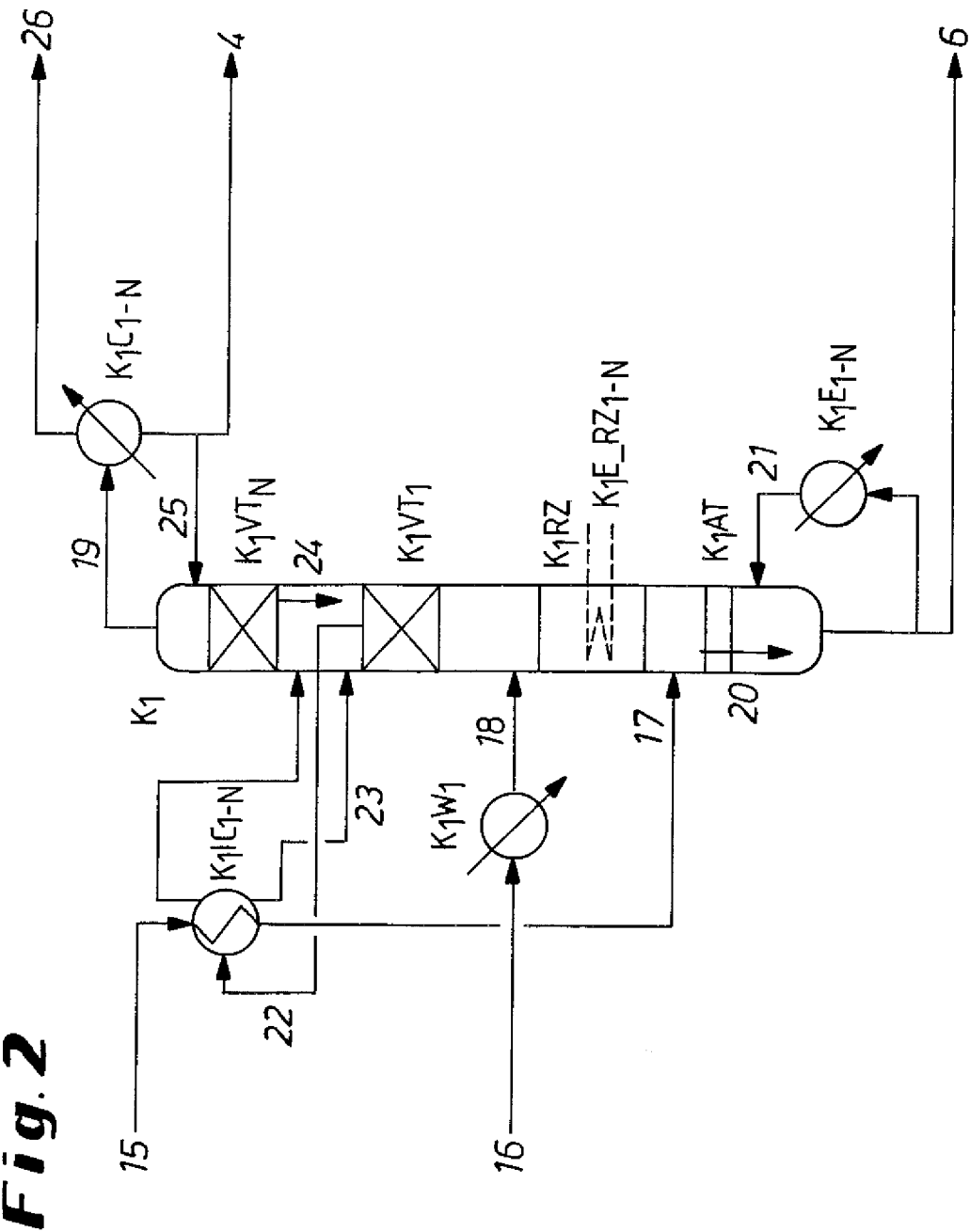

FIG. 2 describes a particularly preferred embodiment of a first reaction column (reactive rectification column) with external arrangement of an intermediate condenser and combination with the evaporation of the dialkyl carbonate to recycle the heat of condensation obtained.

FIG. 3 describes a preferred embodiment of the separation of dialkyl carbonate and alcohol of reaction by the hybrid process.

Figure 4:
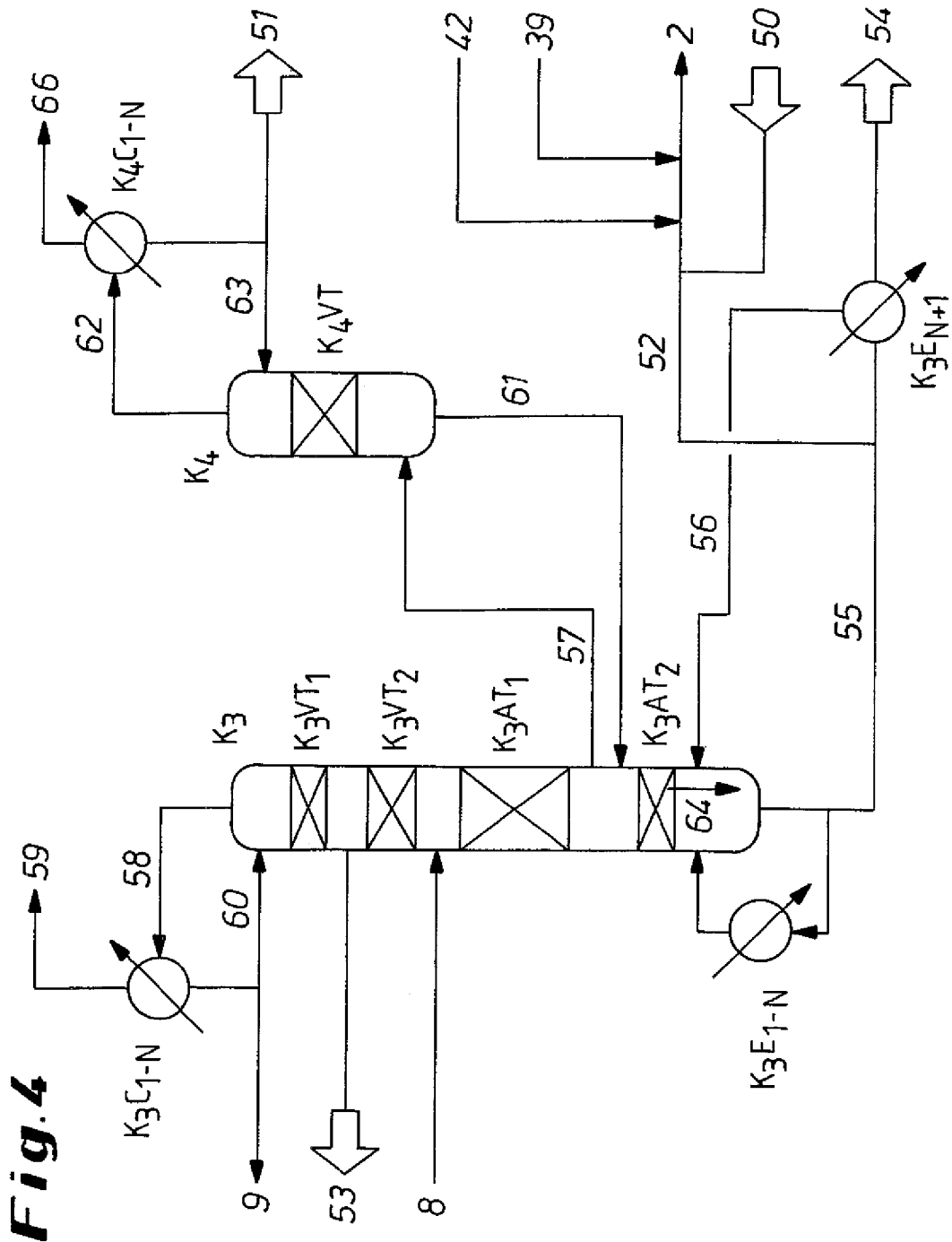

FIG. 4 describes a preferred embodiment of process section (e) for purification of the diaryl carbonate obtained in a two-stage reaction.

FIG. 5a describes sections of the condensation at the top of a reaction or distillation column used in the process, the column diameter remaining unchanged in the region of the condensation.

Figure 5B:
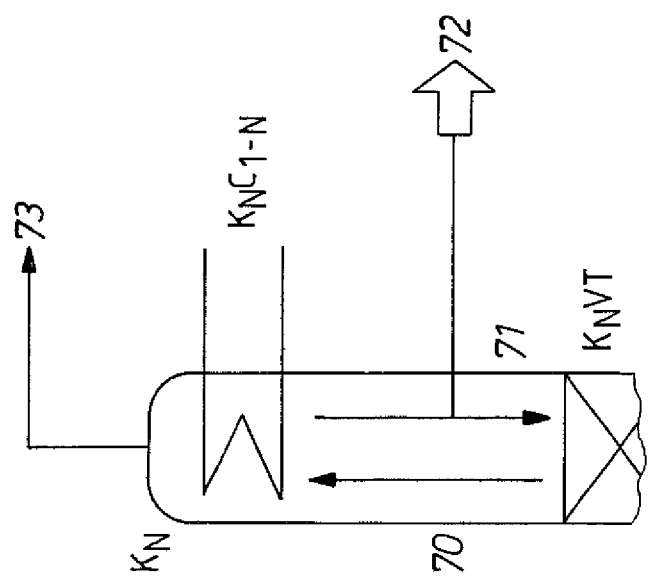

FIG. 5b describes sections of the condensation at the top of a reaction or distillation column used in the process, with a reduction in the column diameter in the direction of the top of the column.

FIG. 6 describes process section (d) for removal of medium-boiling secondary compounds whose boiling point is between that of the dialkyl carbonate used and that of the alkyl aryl carbonate formed in the reaction.

Figure 7:
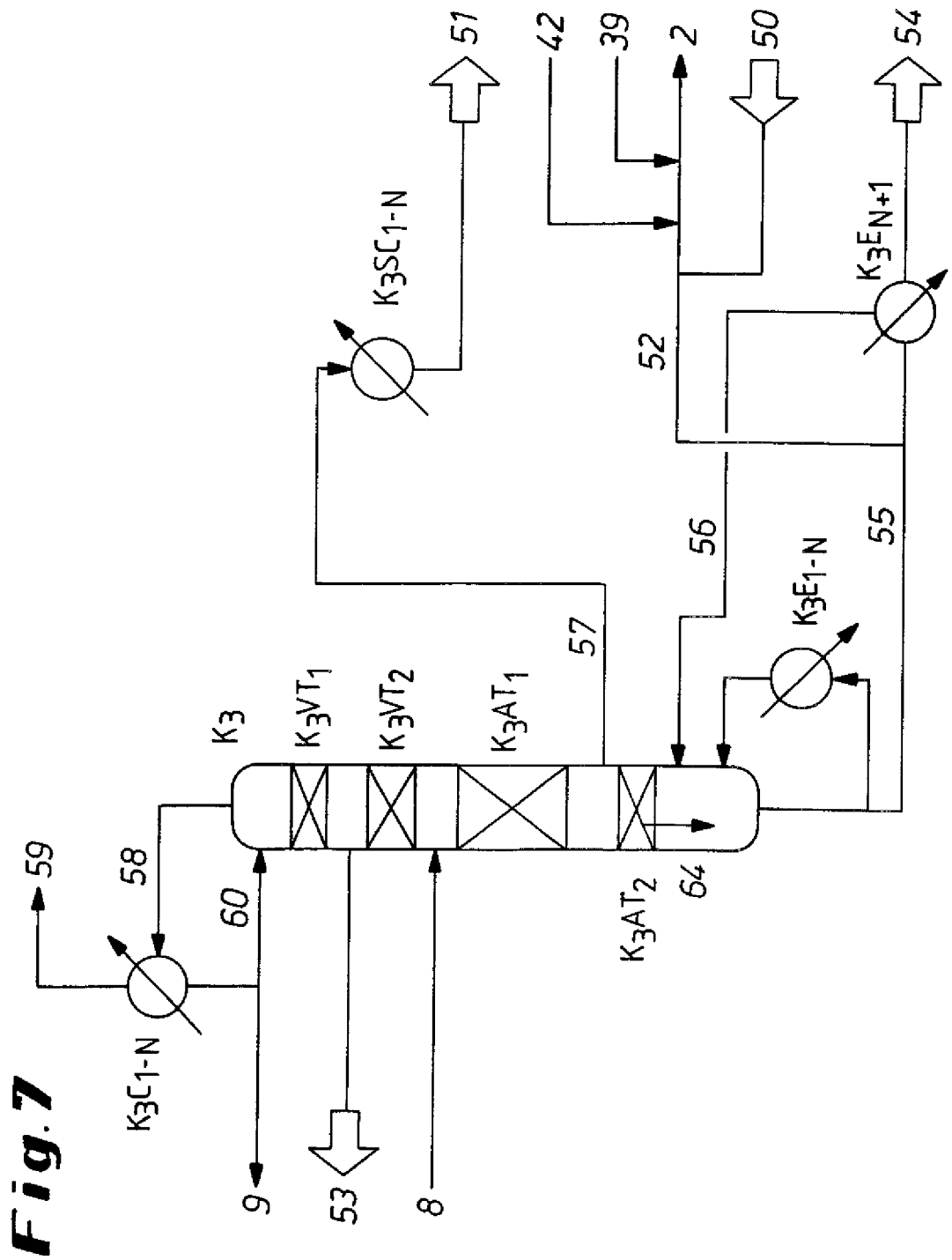

FIG. 7 describes a preferred embodiment of process section (e) for purification of the diaryl carbonate obtained in an at least two-stage reaction, process section (e) having only one single distillation column.

Figure 8:
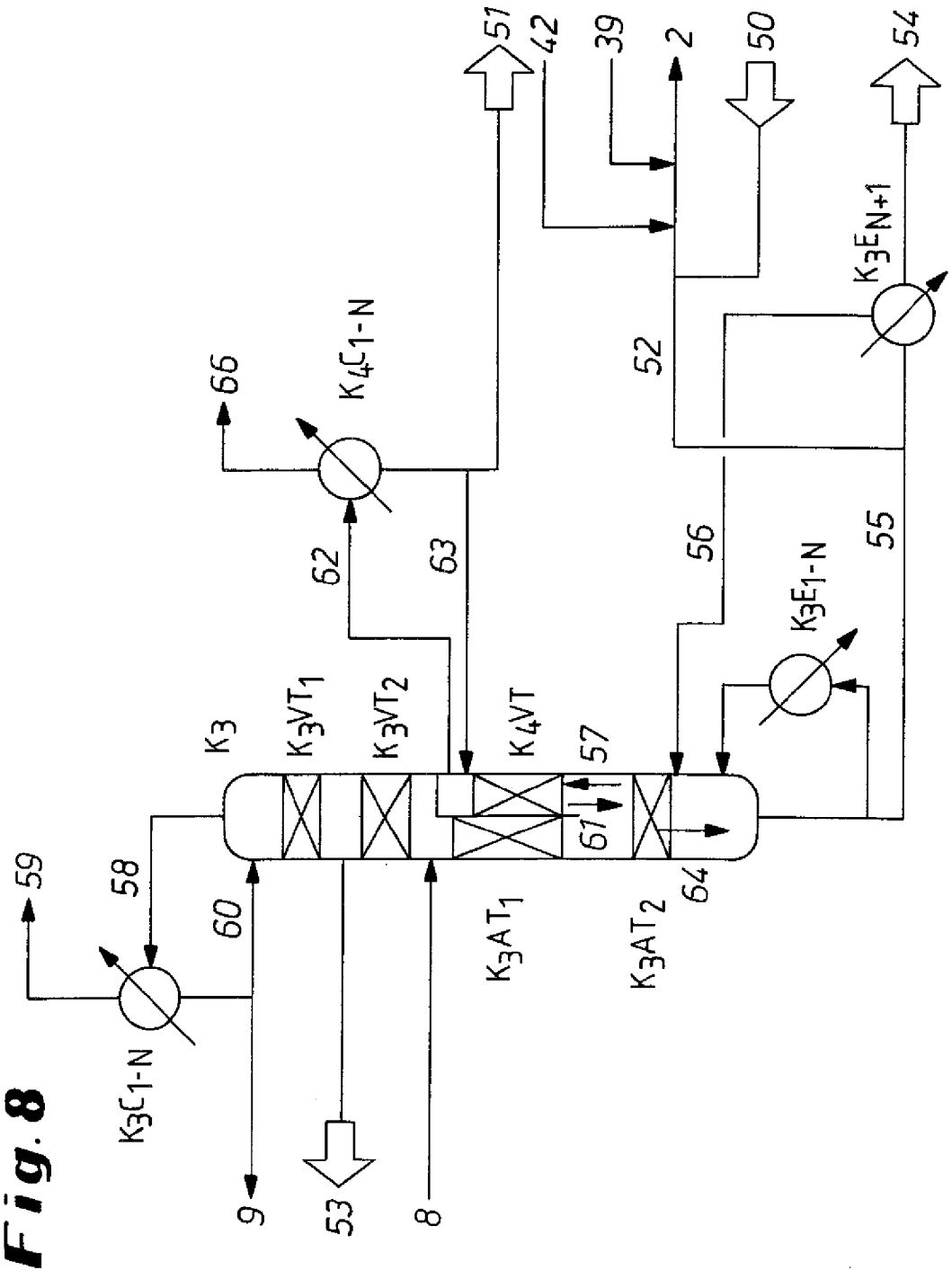

FIG. 8 describes a further preferred embodiment of process section (e) for purification of the diaryl carbonate obtained in an at least two-stage reaction with an integrated sidestream column.

Figure 9:
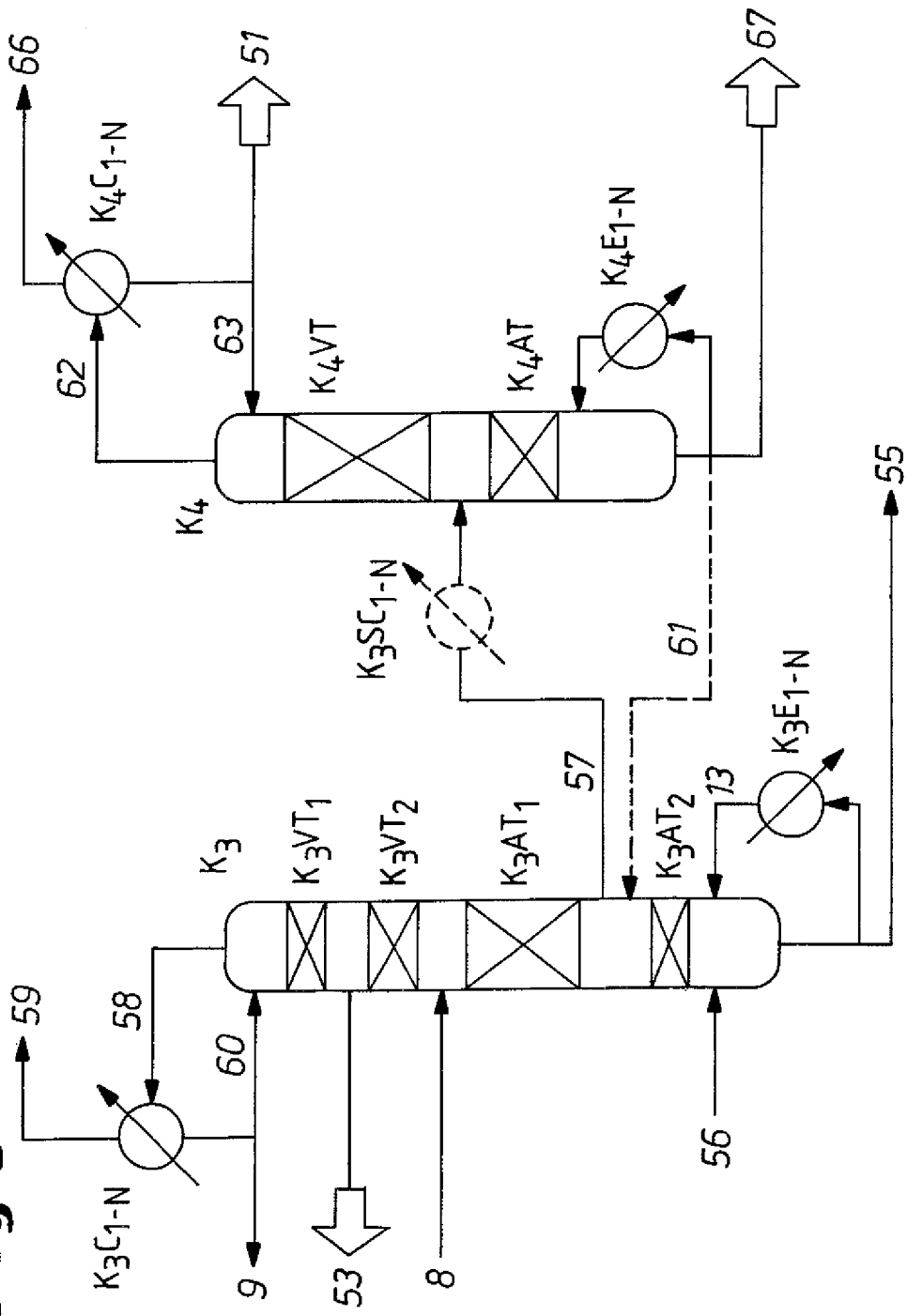

FIG. 9 describes a further preferred embodiment of process section (e) for purification of the diaryl carbonate obtained in an at least two-stage reaction with a sidestream column, said sidestream column possessing both a rectifying section and a stripping section.

Figure 10:
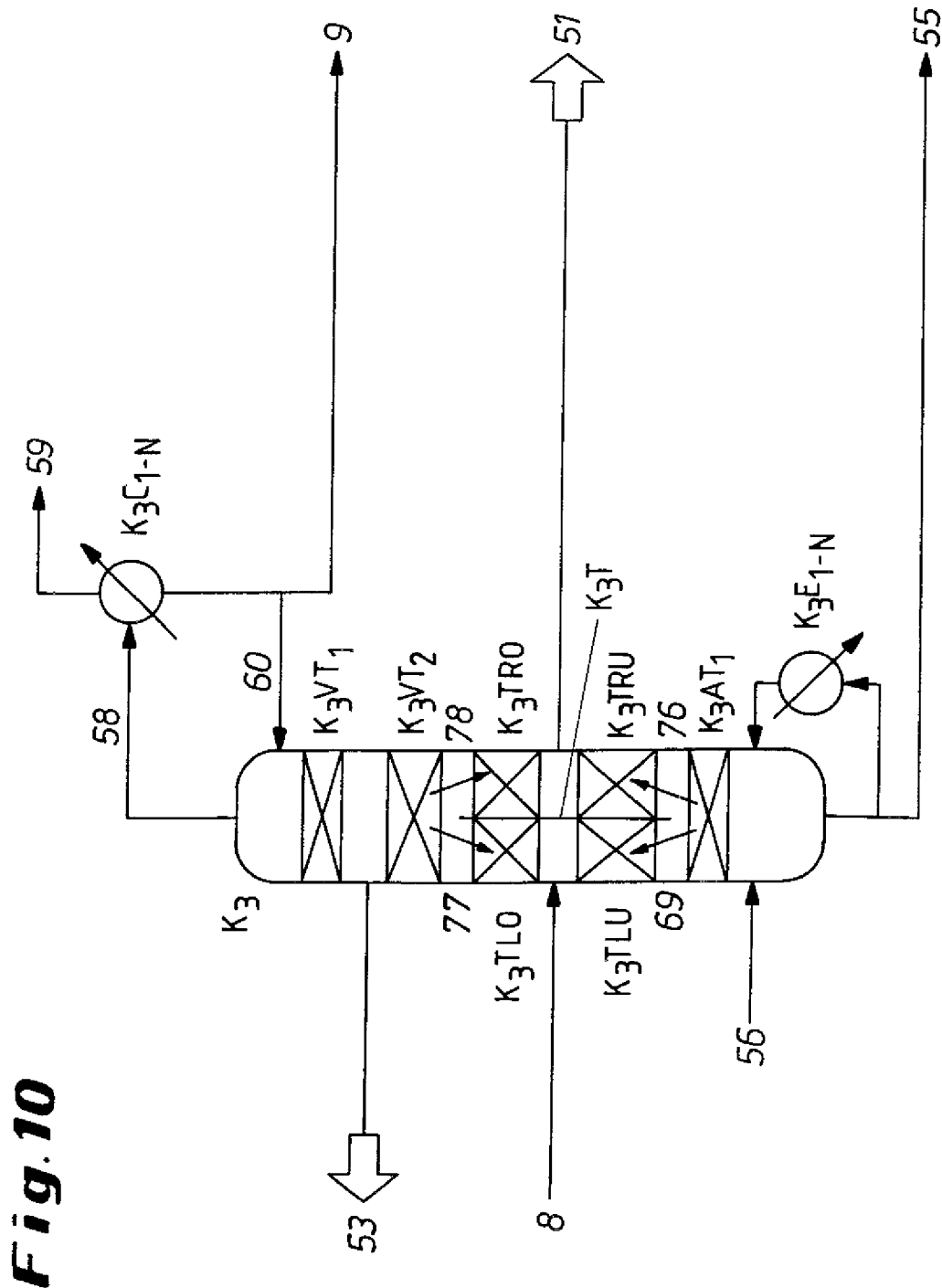

FIG. 10 describes a further preferred embodiment of process section (e) for purification of the diaryl carbonate obtained in an at least two-stage reaction, the distillation column being designed as a dividing wall column with liquid sidestream withdrawal.

Figure 11:
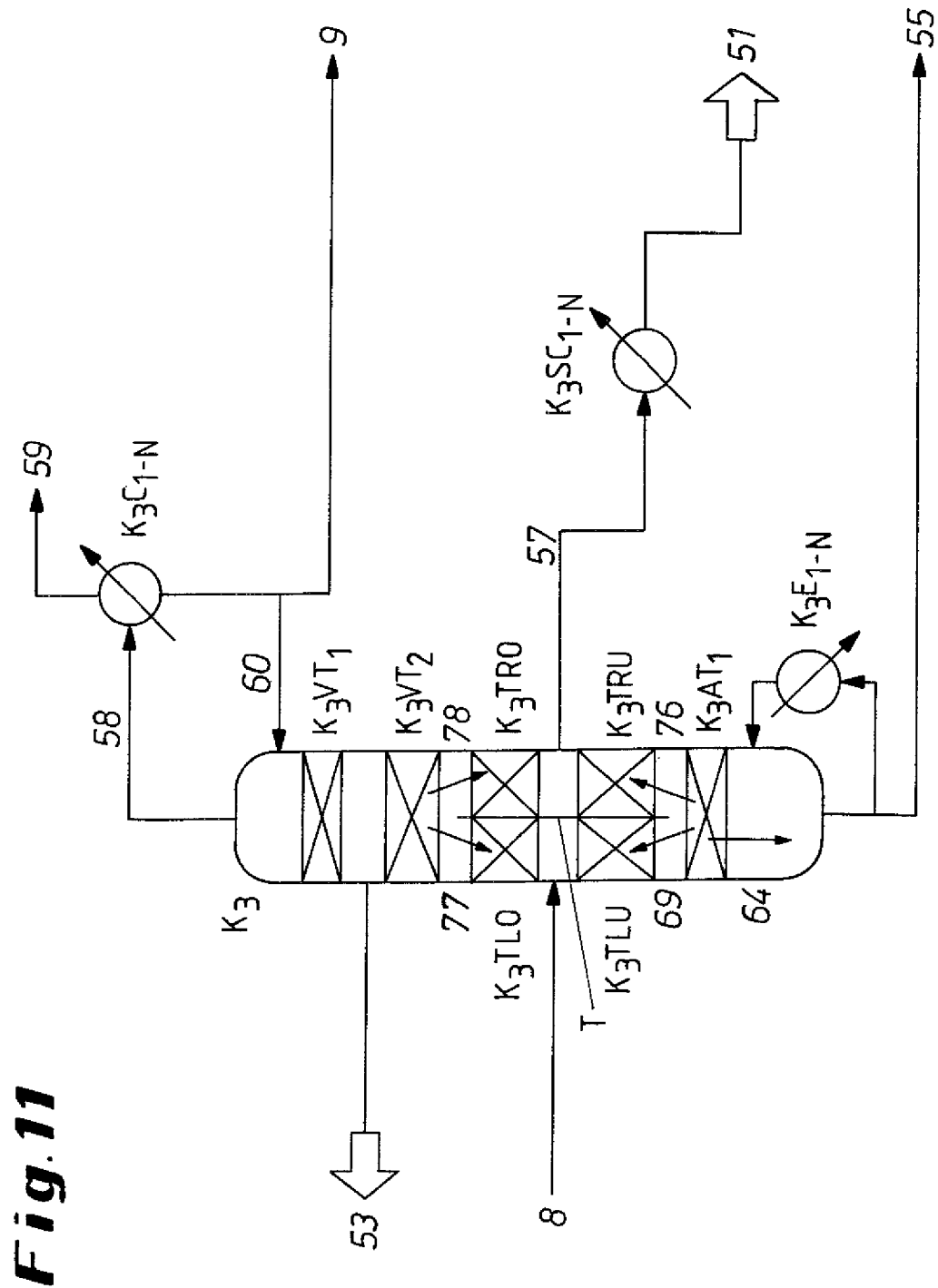

FIG. 11 describes a further preferred embodiment of process section (e) for purification of the diaryl carbonate obtained in an at least two-stage reaction, the distillation column being designed as a dividing wall column with vaporous sidestream withdrawal.

FIG. 12 describes a preferred embodiment of process section (d) for removal of medium-boiling secondary compounds whose boiling point is between that of the dialkyl carbonate used and that of the alkyl aryl carbonate formed in the reaction, in which the second intermediate boiler distillation column is designed as a dividing wall column.

Figure 13:
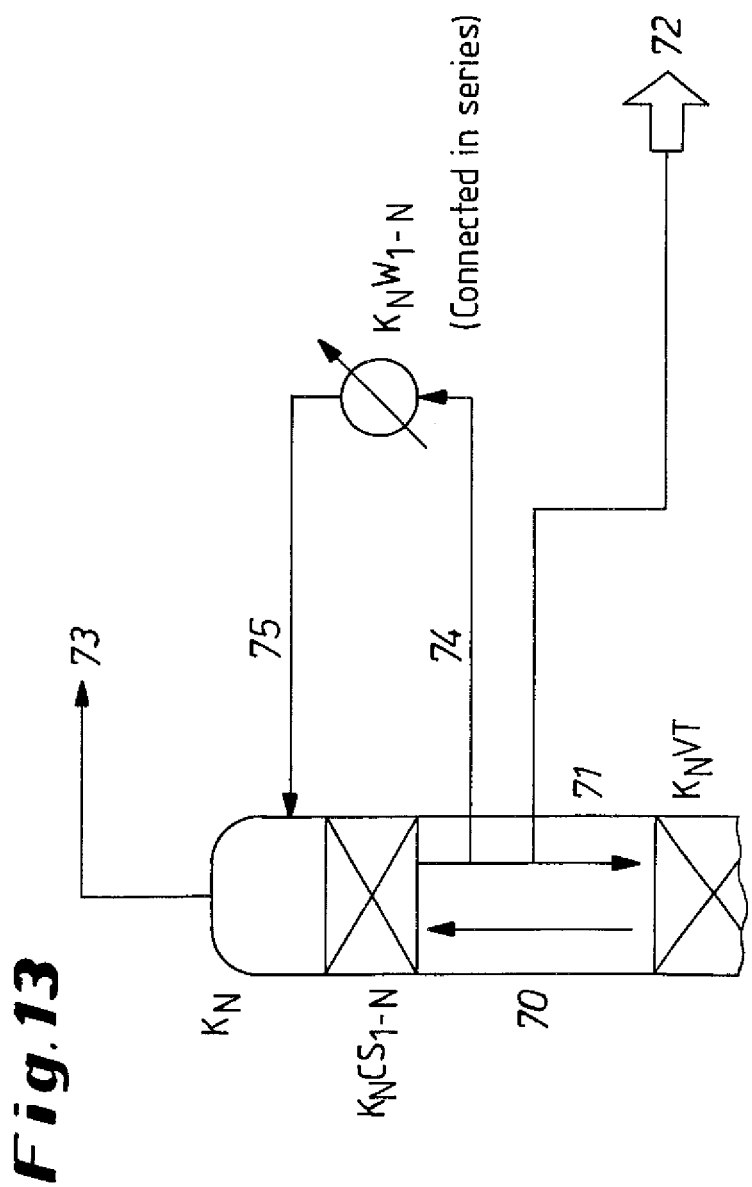

FIG. 13 describes a section of a further preferred embodiment of the condensation at the top of a reaction or distillation column used in the process, the condensation being effected in a further column sector and the heat of condensation being removed via an external heat exchanger.

Figure 14:
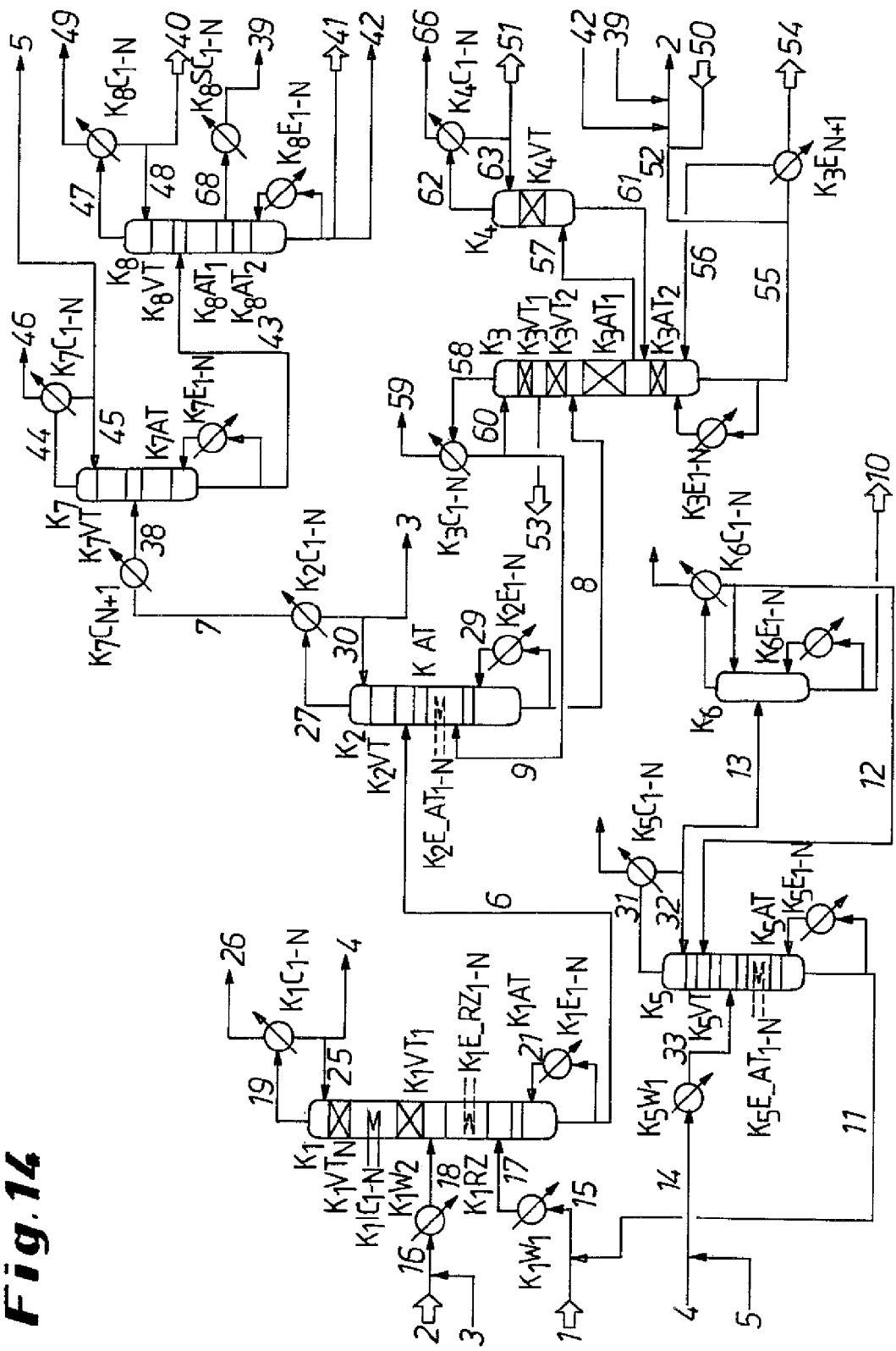

FIG. 14 describes a preferred embodiment of the overall process comprising process steps (a) to (e).

The figures serve to illustrate the invention by way of example and should not be interpreted as a restriction.

In FIGS. 1 to 14, the meanings are:

$K_1$ Alkyl aryl carbonate reaction column (first reaction column)
$K_1C_{1-N}$ N Top condenser(s) 1 to N of $K_1$
$K_1E_{1-N}$ Evaporator(s) 1 to N of $K_1$
$K_1IC_{1-N}$ Intermediate condenser(s) 1 to N of $K_1$
$K_1VT_1$ Lower rectifying section of $K_1$
$K_1VT_N$ Upper rectifying section of $K_1$
$K_1W_1$ Preheater/evaporator/superheater of $K_1$ for dialkyl carbonate-comprising stream
$K_1W_2$ Preheater/evaporator of $K_1$ for reactant stream comprising aromatic hydroxyl compound
$K_1RZ$ Reaction zone of $K_1$
$K_1AT$ Stripping section of $K_1$
$K_1E\_RZ_{1-N}$ Intermediate evaporator(s) 1 to N in the region of the reaction zone of $K_1$
$K_2$ Diaryl carbonate reaction column (second reaction column)
$K_2C_{1-N}$ Top condenser(s) 1 to N of $K_2$
$K_2C_{N+1}$ Condenser for residue vapour stream from $K_2C_{1-N}$ comprising medium-boiling secondary compounds
$K_2E_{1-N}$ Evaporator(s) 1 to N of $K_2$
$K_2VT$ Rectifying section of $K_2$
$K_2AT$ Stripping section and reaction zone of $K_2$
$K_2E\_AT_{1-N}$ Intermediate evaporator(s) 1 to N in the stripping section of $K_2$
$K_3$ Diaryl carbonate fine distillation column (first diaryl carbonate distillation column)
$K_3C_{1-N}$ Optional multistage top condenser(s) 1 to N of $K_3$
$K_3E_{1-N}$ Optional multistage evaporator(s) 1 to N of $K_3$
$K_3E_{N+1}$ Additional evaporator for concentration of the bottom product stream not recycled into the process from the bottom of column $K_3$ and/or of the column evaporator(s) $K_3E_{1-N}$
$K_3SC_{1-N}$ Optional multistage condenser(s) 1 to N for vaporous sidestream of $K_3$
$K_3VT_1$ Upper rectifying section of $K_3$
$K_3VT_2$ Lower rectifying section of $K_3$
$K_3AT_1$ Upper stripping section of $K_3$
$K_3AT_2$ Lower stripping section of $K_3$
$K_3T$ Dividing wall of $K_3$
$K_3TLO$ Rectifying section on the feed side of the dividing wall of $K_3$
$K_3TLU$ Stripping section on the feed side of the dividing wall of $K_3$
$K_3TRU$ Rectifying section on the withdrawal side of the dividing wall of $K_3$
$K_3TRO$ Stripping section on the withdrawal side of the dividing wall of $K_3$ $K_4$ Diaryl carbonate sidestream column (second diaryl carbonate distillation column)
$K_4C_{1-N}$ Optional multistage top condenser(s) 1 to N of $K_4$
$K_4$VT Rectifying section of $K_4$
$K_4$AT Stripping section of $K_4$
$K_4E_{1-N}$ Optional multistage evaporator(s) 1 to N of $K_4$
$K_5$ Dialkyl carbonate distillation column
$K_5$VT Rectifying section of $K_5$
$K_5$AT Stripping section of $K_5$
$K_5W_1$ Preheater/evaporator of $K_5$ for stream comprising alcohol of reaction and dialkyl carbonate
$K_5C_{1-N}$ Top condenser(s) 1 to N of $K_5$
$K_5E_{1-N}$ Evaporator(s) 1 to N of $K_5$
$K_5E\_AT_{1-N}$ Intermediate evaporator(s) 1 to N in the stripping section of $K_5$
$K_6$ Alcohol of reaction distillation column
$K_6C_{1-N}$ Top condenser(s) 1 to N of $K_6$
$K_6E_{1-N}$ Evaporator(s) 1 to N of $K_6$
$K_6$VT Rectifying section of $K_6$
$K_6$AT Stripping section of $K_6$
M Membrane separation (vapour permeation or prevaporation)
MRC Condenser for retentate after the membrane separation
MPC Condenser for permeate after the membrane separation
$K_7$ Alkyl aryl ether preconcentration column (first intermediate boiler column)
$K_7C_{1-N}$ Optional multistage top condenser(s) 1 to N of $K_7$
$K_7E_{1-N}$ Optional multistage evaporator(s) 1 to N of $K_7$
$K_7$VT Rectifying section of $K_7$
$K_7$AT Stripping section of $K_7$
$K_8$ Alkyl aryl ether column (second intermediate boiler column)
$K_8C_{1-N}$ Optional multistage top condenser(s) 1 to N of $K_8$
$K_8SC_{1-N}$ Optional multistage condenser(s) 1 to N for vaporous sidestream of $K_8$
$K_8E_{1-N}$ Optional multistage evaporator(s) 1 to N of $K_8$
$K_8$VT Rectifying section of $K_8$
$K_8AT_1$ Upper stripping section of $K_8$
$K_8AT_2$ Lower stripping section of $K_8$
$K_8$T Dividing wall of $K_8$
$K_8$TLO Rectifying section on the feed side of the dividing wall of $K_8$
$K_8$TLU Stripping section on the feed side of the dividing wall of $K_8$
$K_8$TRU Rectifying section on the withdrawal side of the dividing wall of $K_8$
$K_8$TRO Stripping section on the withdrawal side of the dividing wall of $K_8$
$K_N$ One of the reaction or distillation columns $K_1$ to $K_8$
$K_NC_{1-N}$ Optional multistage top condenser(s) 1 to N of $K_N$
$K_N$VT Rectifying section of $K_N$
$K_NCS_{1-N}$ Column segment(s) 1 to N of $K_N$ with direct condensation
$K_NW_{1-N}$ Heat exchanger(s) 1 to N for cooling of a circulation stream for the condensation in $K_NCS_{1-N}$ of $K_N$ Additionally named in FIGS. 1 to 14 are the following streams:
1 Reactant feed stream comprising dialkyl carbonate
2 Reactant feed stream comprising aromatic hydroxyl compound
3 Distillate of $K_2$
4 Distillate of $K_1$
5 Stream comprising dialkyl carbonate and alcohol of reaction
6 Bottom product of $K_1$
7 Intermediate boiler purge
8 Bottom product of $K_2$
9 Stream comprising alkyl aryl carbonate and aromatic hydroxyl compound
10 Discharge of alcohol of reaction from $K_6$
11 Dialkyl carbonate-comprising stream from $K_5$
12 Distillate of $K_6$
13 Distillate of $K_5$
14 Stream comprising dialkyl carbonate and alcohol of reaction
15 Dialkyl carbonate-comprising stream to $K_1$
16 Aromatic hydroxyl compound-comprising stream to $K_1$
17 Dialkyl carbonate-comprising stream after evaporation
18 Stream comprising aromatic hydroxyl compound after heating
19 Vapour stream at the top of $K_1$
20 Liquid effluent from the stripping section of $K_1$
21 Vapour-liquid mixture from bottom evaporator of $K_1$
22 Vapour mixture from lower rectifying section of $K_1$
23 Condensate of the intermediate condenser(s) of $K_1$
24 Efflux of liquid mixture from upper rectifying section of $K_1$
25 Reflux of $K_1$
26 Remaining vapour mixture from condensation of $K_1$
27 Vapour stream at the top of $K_1$
28 Efflux of liquid mixture from reaction zone or if appropriate stripping section of $K_2$
29 Vapour-liquid mixture from bottom evaporator of $K_2$
30 Reflux of $K_2$
31 Vapour stream at the top of $K_5$
32 Reflux of $K_5$
33 Feed mixture to $K_5$
34 Distillate $K_5$ to membrane separation (M)
35 Membrane separation (M) retentate to condenser (MRC)
36 Liquid retentate to $K_5$
37 Permeate of membrane separation (M) to condenser (MPC)
38 Stream comprising medium-boiling secondary compounds
39 Stream comprising aromatic hydroxyl compound from $K_8$
40 Distillate stream comprising intermediate boilers
41 Bottom product comprising intermediate boilers for disposal
42 Bottom product of $K_8$ to $K_1$ or $K_2$
43 Bottom product comprising aromatic hydroxyl compound and medium-boiling secondary compounds
44 Vapour stream at the top of $K_7$
45 Reflux of $K_7$
46 Residue vapour stream after condensation in $K_7C_{1-N}$
47 Vapour stream at the top of $K_8$
48 Reflux of $K_8$
49 Residual vapour stream after condensation in $K_8C_{1-N}$
50 Stream comprising aromatic hydroxyl compound and catalyst
51 Stream comprising diaryl carbonate with high purity
52 Stream comprising high-boiling secondary compounds and catalyst
53 Stream comprising medium-boiling secondary compounds
54 Stream comprising high-boiling secondary compounds and catalyst for disposal
55 Stream comprising high-boiling secondary compounds and catalyst
56 Vapour stream comprising diaryl carbonate to $K_3$
57 Vapour stream comprising diaryl carbonate to $K_4$
58 Vapour stream of $K_3$ 59 Residual vapour stream after condensation in $K_3C_{1-N}$
60 Reflux of $K_3$
61 Bottom product of $K_4$
62 Vapour stream of $K_4$
63 Reflux of $K_4$
64 Efflux of liquid from the lower stripping section of $K_3$
65 Bottom product of $K_8$
66 Residual vapour stream after condensation in $K_4C_{1-N}$
67 Purge stream from the bottom product of $K_4$
68 Sidestream comprising aromatic hydroxyl compound from $K_8$
69 Vapour stream from stripping section of $K_3$ to the feed side (embodiment as a dividing wall column)
70 Vapour stream from rectifying section of $K_N$ to the condensation
71 Reflux to rectifying section of $K_N$
72 Distillate
73 Residual vapour stream after condensation
74 External circulation in the case of condensation in a column segment before cooling
75 External circulation in the case of condensation in a column segment after cooling
76 Vapour stream from stripping section of $K_3$ to withdrawal side (embodiment as a dividing wall column)
77 Liquid from rectifying section of $K_3$ to the feed side (embodiment as a dividing wall column)
78 Liquid from stripping section of $K_3$ to the withdrawal side (embodiment as a dividing wall column)

FIG. 1 shows, inter alia, a first reaction column $K_1$, into which the two reactant streams, i.e. a stream 16 comprising the aromatic hydroxyl compound and a stream 15 comprising the dialkyl carbonate, are conducted counter to one another in the manner of a countercurrent transesterification in the region of a reaction zone RZ, and converted to alkyl aryl carbonates and small proportions of diaryl carbonates.

The stream 15 comprising the dialkyl carbonate may—especially in continuous processes—as well as the dialkyl carbonate, also comprise portions of the aromatic hydroxyl compound, the aliphatic hydroxyl compound $R^1$—OH and/or $R^2$—OH (alcohol of reaction) obtained in the reaction, very small amounts of the alkyl aryl carbonate and/or diaryl carbonate obtained in the transesterification, and undesired secondary components formed in the reaction. The stream 15 comprising the dialkyl carbonate may, for example, comprise 0 to 5% by weight, preferably 0.05 to 3% by weight and more preferably 0.05 to 2% by weight of the alcohol of reaction, 0 to 40% by weight, preferably 0 to 10% by weight and more preferably 0 to 5% by weight of the aromatic hydroxyl compound, 0 to 5% by weight of alkyl aryl carbonate, 0 to 5% by weight of diaryl carbonate and 0 to 5% by weight of other secondary compounds obtained in the reaction (for example alkyl aryl ethers) or impurities already present in the reactants, based in each case on the total weight of the stream comprising dialkyl carbonate. The stream 15 comprising the dialkyl carbonate preferably comprises 50 to 100% by weight of dialkyl carbonate based on the total weight of the stream comprising dialkyl carbonate, where the proportions of the individual components mentioned above add up to 100% by weight. The stream 16 comprising the aromatic hydroxyl compound may—especially in continuous processes—as well as the aromatic hydroxyl compound, also comprise portions of the dialkyl carbonate, the alkyl aryl carbonate and/or diaryl carbonate obtained in the transesterification, and very small amounts of the alcohol of reaction and of undesired by-products formed in the reaction. For example, the content of the dialkyl carbonate may be 0 to 50% by weight, the content of the alcohol of reaction 0 to 10% by weight, preferably 0 to 5% by weight, the content of the alkyl aryl carbonate and of the diaryl carbonate in each case 0 to 10% by weight, preferably 0 to 5% by weight, and the content of the undesired by-product 0 to 5% by weight, preferably 0 to 1% by weight, based in each case on the total weight of the stream comprising the aromatic hydroxyl compound. The catalyst can additionally be fed into the reaction column with the stream 16 comprising the aromatic hydroxyl compound. In this case, the content of catalyst is preferably 0 to 5% by weight, based on the total weight of the stream comprising the aromatic hydroxyl compound. The stream 16 comprising the aromatic hydroxyl compound preferably comprises 50 to 100% by weight of aromatic hydroxyl compound, based on the total weight of the stream comprising the aromatic hydroxyl compound, where the proportions of the individual components mentioned above add up to 100% by weight.

The stream 15 comprising the dialkyl carbonate, before being introduced into the column $K_1$, is partly or fully evaporated and optionally superheated. The stream 16 comprising the aromatic hydroxyl compound is heated before being introduced into the column $K_1$ and optionally partly evaporated at the same time. The reactant streams 17 and 18, in each case after evaporation and optional superheating or after heating, are conducted in countercurrents to one another in the reaction zone $K_1RZ$, i.e. the stream 18 comprising the aromatic hydroxyl compound is fed in at the upper end of the reaction zone $K_1RZ$ in heated, predominantly liquid form, and the stream 17 comprising the dialkyl carbonate is fed in at the lower end of the reaction zone $K_1RZ$ predominantly in gaseous or optionally slightly superheated form. The aliphatic hydroxyl compound $R^1$—OH and/or $R^2$—OH obtained in the reaction is drawn off in vaporous form (19) together with as yet unconverted dialkyl carbonate at the top of the column, and the less volatile alkyl aryl carbonate is withdrawn together with as yet unconverted amounts of the aromatic hydroxyl compound, diaryl carbonate and any further nonvolatile compounds as the liquid bottom product of $K_1$ (6). The energy required to establish the desired temperature profile can be effected, inter alia, at the bottom of the column by one or more evaporators $K_1E_{1-N}$. To this end, the liquid mixture (20) which effluxes from the stripping section $K_1AT$, or, in the absence of a stripping section, from the reaction zone $K_1RZ$, is partly evaporated. According to the evaporator configuration, only vapour or a vapour-liquid mixture (stream 21) is obtained at the outlet of the evaporator. The vapour present in stream 21 is fed to the stripping section ($K_1AT$) from the bottom or, if no stripping section is present, to the reaction zone $K_1RZ$ from the bottom. In the region of the reaction zone, heat can be supplied by additional intermediate evaporators $K_1E\_RZ_{1-N}$. In the stripping section $K_1AT$ provided between reaction zone $K_1RZ$ and evaporator $K_1E_{1-N}$, the alkyl aryl carbonate formed and the diaryl carbonate are concentrated, in the course of which the disproportionation reaction of alkyl aryl carbonate to diaryl carbonate sets in to an enhanced degree as early as in this part of the column $K_1$ as a result of the depletion of dialkyl carbonate.

In one or more rectifying section(s) present between the condenser(s) $K_1C_{1-N}$ and reaction zone $K_1RZ$, the aliphatic hydroxyl compound (alcohol of reaction) formed in the reaction and the excess dialkyl carbonate are concentrated. This should establish a content of aromatic hydroxyl compound(s) in the distillate 4 of 0 to 40% by weight, preferably 0 to 10% by weight, more preferably 0 to 5% by weight, based on the total weight of the distillate 4. The rectifying section is divided into at least two sectors, the upper and the lower rectifying section, in which case one or more intermediate condenser(s) $K_1IC_{1-N}$, preferably at least one intermediate condenser $K_1IC_1$, is/are present between the upper rectifying section $K_1VT_N$ and the lower rectifying section $K_1VT_1$. This/these intermediate condenser(s) $K_1IC_{1-N}$ or this intermediate condenser $K_1IC_1$ condenses) a portion of the vapours 22 ascending out of the lower rectifying section $K_1VT_1$. The vaporous mixture 22 which enters the intermediate condenser(s) $K_1IC_{1-N}$, preferably at least one intermediate condenser $K_1IC_1$, comprises preferably 10 to 80% by weight of aromatic hydroxyl compound. Owing to comparatively high amounts of aromatic hydroxyl compound, the condensation temperature in the intermediate condenser(s) $K_1IC_{1-N}$ is therefore significantly higher compared to the condensation temperature in the top condenser $K_1C_{1-N}$(N: condenser is optionally multistage). According to the operating pressure and position of the concentration profile, the condensation temperature in the intermediate condenser(s) may preferably be in the range of 100 to 300° C., more preferably of 120 to 250° C., most preferably of 150 to 240° C., and in the top condenser preferably in the range of 0 to 250° C., more preferably of 40 to 200° C. The condensate 23 obtained in the intermediate condenser(s) $K_1IC_{1-N}$ and the liquid 24 which effluxes out of the upper rectifying section $K_1VT_N$ above it is passed to the lower rectifying section $K_1VT_1$. The vaporous mixture downstream of the intermediate condenser(s) passes into the upper rectifying section $K_1VT_N$. The vapour 19 coming from the upper rectifying section $K_1VT_N$ is very substantially condensed in the condenser(s) $K_1C_{1-N}$, and the condensate is partly fed (25) back to the upper rectifying section $K_1VT_N$ as reflux and partly withdrawn as distillate stream 4. The distillate stream 4 comprises essentially the dialkyl carbonate used in excess and the corresponding alkyl alcohol $R^1$—OH and/or $R^2$—OH (alcohol of reaction) formed in the reaction, and optionally small amounts of the aromatic hydroxyl compound. The residual vapour mixture from the condenser(s) $K_1C_{1-N}$ is withdrawn as vapour stream 26.

The heat of condensation released in the intermediate condenser(s) $K_1IC_{1-N}$, preferably at least the intermediate condenser $K_1IC_1$, can, as described above for the process according to the invention, be recycled directly or indirectly back into the process (not shown in FIGS. 1 and 14).

In a preferred embodiment of the process according to the invention, the heat of condensation obtained in the intermediate condenser(s) $K_1IC_{1-N}$, preferably at least the intermediate condenser $K_1IC_1$, is used to heat a heat carrier medium. This is in turn used to evaporate and superheat the dialkyl carbonate-comprising stream 15 used in the countercurrent transesterification in the reaction column $K_1$. This preferred embodiment is an indirect utilization of the heat of condensation.

Another preferred embodiment of the transesterification in the first reaction column in the presence of at least one intermediate condenser is shown in FIG. 2. In this case, the intermediate condenser(s) are configured outside the first reaction column. The heating, evaporation and optional superheating of the dialkyl carbonate-comprising stream 15 are likewise effected in the intermediate condenser. In this case, the vaporous mixture 22 of the lower rectifying section $K_1VT_1$ is passed to the intermediate condenser(s) $K_1IC_{1-N}$, preferably to at least one intermediate condenser $K_1IC_1$, where it condenses partially. The condensate 23 obtained is fed back to the lower rectifying section $K_1VT_1$ and the uncondensed vapours are passed into the upper rectifying section $K_1VT_N$. Otherwise, the process shown in FIG. 2 corresponds to that shown in FIG. 1. The above explanations for FIG. 1 therefore apply analogously.

According to FIG. 1, the bottom product 6 of the first reaction column $K_1$ is fed to a second reaction column $K_2$. This may comprise 0 to 60% by weight of diaryl carbonate, 5 to 80% by weight of alkyl aryl carbonate, 5 to 95% by weight of the aromatic hydroxyl compound, 1 to 80% by weight of dialkyl carbonate, 0 to 5% by weight of catalyst and 0 to 5% by weight of other secondary compounds obtained in the reaction (for example alkyl aryl ethers) or impurities already present in the reactants, based in each case on the total weight of the bottom product stream 6. The percentages are based on the total weight of the bottom product stream 6, the proportions of the individual components mentioned above adding up to 100% by weight.

In addition to the bottom product of the first reaction column, at least one further stream 9 comprising alkyl aryl carbonate may additionally be fed to the second reaction column. This stream 9 may originate, for example, from a workup step for purification of the diaryl carbonate, for example a diaryl carbonate distillation column $K_3$.

This may comprise 0 to 10% by weight of diaryl carbonate, 10 to 100% by weight of alkyl aryl carbonate, 0 to 90% by weight of the aromatic hydroxyl compound, 0 to 20% by weight of dialkyl carbonate and 0 to 20% by weight of other secondary compounds obtained in the reaction (for example alkyl aryl ethers) or impurities already present in the reactants, based in each case on the total weight of the stream comprising dialkyl carbonate. The percentages are based on the total weight of stream 9, the proportions of the individual components mentioned above adding up to 100% by weight.

Streams 6 and 9 are fed to the reaction zone $K_2AT$ of the second reaction column.

The alcohol of reaction $R^1$—OH and/or $R^2$—OH obtained in the transesterification is drawn off in vaporous form (27) at the top of the column $K_2$ together with dialkyl carbonate which is as yet unconverted or has been released in the disproportionation and unconverted aromatic hydroxyl compound, and the less volatile diaryl carbonate is withdrawn (8) as a liquid stream at the bottom of the second reaction column $K_2$ together with as yet unconverted amounts of the aromatic hydroxyl compound, alkyl aryl carbonate and possibly further nonvolatile compounds.

The energy required to establish the desired temperature profile can be effected, inter alia, at the bottom of the column by means of one or more evaporators $K_2E_{1-N}$. To this end, the liquid mixture (28) effluxing from the reaction zone is partially evaporated. According to the evaporator configuration, only vapour or a vapour-liquid mixture (stream 29) is obtained at the outlet of the evaporator. The vapour present in stream 29 is fed from the bottom into the stripping section ($K_2AT$), which simultaneously also functions as a reaction zone and consists of a plurality of sectors. In the region of the reaction zone, additional intermediate evaporators $K_2E\_AT_{1-N}$ may supply heat. In the reaction zone $K_2AT$ and in the evaporator $K_2E_{1-N}$, both reaction (transesterification and/or preferably disproportionation) and removal of the low-boiling reaction products formed (alcohol of reaction and dialkyl carbonate) and of the aromatic hydroxyl compound proceed.

In a rectifying section $K_2VT$ present between the condenser(s) $K_2C_{1-N}$ and reaction zone $K_2AT$, the content of high-boiling compounds, for example alkyl aryl carbonate or diaryl carbonate, is reduced. This preferably establishes a content of alkyl aryl carbonate in the distillate 3 of 0 to 20% by weight preferably 0 to 5% by weight, more preferably of 0 to 2% by weight, based on the total weight of the distillate 3.

The rectifying section may be configured analogously to the first reaction column with one or more intermediate condensers. In the preferred embodiment shown in FIG. 1 and FIG.

14, the rectifying section of $K_2$ is, however, configured without intermediate condenser(s).

The condenser(s) $K_2C_{1-N}$, in a very particularly preferred embodiment a cascade of condensers, at the top of $K_2$ condense(s) a portion of the vapours 27 ascending out of the rectifying section $K_2VT$. The vaporous mixture 27 entering the condenser(s) $K_2C_{1-N}$ comprises preferably 10 to 90% by weight of aromatic hydroxyl compound. The condensation temperature in the condenser(s) $K_2C_{1-N}$ is therefore high owing to comparatively high amounts of aromatic hydroxyl compound. According to the operating pressure and composition of the vaporous mixture 27, the condensation temperature in the condenser(s) may preferably be in the range of 100 to 300° C., more preferably of 120 to 250° C., most preferably of 150 to 240° C. The condensate is partly fed back to the rectifying section $K_2VT$ as reflux 30 and partly withdrawn as distillate stream 3.

The distillate stream 3 comprises essentially aromatic hydroxyl compounds and small amounts of alcohol of reaction, preferably 0 to 5% by weight, and can be fed back to the reactant stream of the first reaction column.

The distillate of the first reaction column (4) is fed to a distillation column $K_5$ (dialkyl carbonate distillation column) for separation of the dialkyl carbonate from the alcohol of reaction formed, optionally together with further streams (5 and/or 12) comprising alcohol of reaction and dialkyl carbonate, optionally after heating and/or partial evaporation, the resulting stream 11 comprising dialkyl carbonate being fed back to the feed stream 15 comprising dialkyl carbonate to the first reaction column, and the alcohol of reaction removed being discharged (10) from the process. Stream 5 may originate, for example, from further purification or by-product removal steps, for example the removal of medium-boiling secondary compounds in $K_7$.

If alcohol of reaction and dialkyl carbonate form an azeotrope, the distillate (13) obtained from the distillation column $K_5$ is preferably an approximately azeotropic mixture. For a complete separation of alcohol of reaction and dialkyl carbonate, at least one further separation step is therefore required.

If alcohol of reaction and dialkyl carbonate do not form an azeotrope, the distillate obtained is preferably alcohol of reaction with a content of 95 to 100% by weight.

The bottom product withdrawn from the distillation column $K_5$ is a mixture comprising dialkyl carbonate with less than 5% by weight of alcohol of reaction.

The dialkyl carbonate distillation column $K_5$ possesses a rectifying section with preferably 5 to 40 theoretical plates for concentration of the alcohol of reaction, and a stripping section with preferably 5 to 40 theoretical plates for concentration of the dialkyl carbonate.

The energy required for the distillation in the dialkyl carbonate distillation column may, inter alia, be effected at the bottom of the column by means of one or more evaporators $K_5E_{1-N}$. In the region of the stripping section $K_5AT$, heat can be supplied by means of additional intermediate evaporators $K_5E\_AT_{1-N}$.

The condenser(s) $K_5C_{1-N}$ condense(s) the vapours 31 ascending out of the rectifying section $K_5VT$. The condensate is partly fed back to the rectifying section $K_5VT$ as reflux 32 and partly withdrawn as distillate stream 13.

The distillate stream 13 comprises alcohol of reaction and dialkyl carbonate in virtually azeotropic composition. When alcohol of reaction and dialkyl carbonate do not form an azeotrope, the distillate obtained is virtually pure alcohol of reaction.

The operating pressure in the dialkyl carbonate distillation column ($K_5$) is adjusted such that the column can be operated with waste heat from the transesterification process. For this purpose, preference is given to utilizing the heat of condensation from the intermediate condenser of the first reaction column and/or the condenser(s) of the second reaction column. Preference is given to adjusting the operating pressure in the column $K_5$ such that the evaporation temperature in the bottom of the column $K_5$ is below the condensation temperature in the intermediate condenser of the first reaction column and/or the condenser(s) of the second reaction column.

If alcohol of reaction and dialkyl carbonate form an azeotrope under the conditions in the distillation column $K_5$, it can be separated by means of entraining agent or extractive rectification, by the two-pressure process or by means of a combination of rectification and membrane separation. Particular preference is given to using the two-pressure process to separate the alcohol of reaction and the dialkyl carbonate, which is likewise illustrated by way of example with reference to FIG. 1.

If the distillate of the distillation column $K_5$ has an azeotropic composition, it is fed to a further column (alcohol of reaction distillation column; $K_6$ in FIGS. 1 and 14), which works at an operating pressure which is below that of the distillation column $K_5$. As a result of the different operating pressure, the position of the azeotrope shifts toward lower proportions of alcohol of reaction. The bottom product 10 obtained in the distillation column $K_6$ is alcohol of reaction having a purity of from 90 to 100% by weight, and the distillate obtained from column $K_6$ is a virtually azeotropic mixture. The column $K_6$ which works at lower operating pressure is, in a particularly preferred embodiment, operated with the heat of condensation of the top condenser(s) of the column $K_5$.

The alcohol of reaction distillation column $K_6$ possesses a rectifying section $K_6VT$ with 5 to 40 theoretical plates for concentration of the alcohol of reaction and a stripping section $K_6AT$ with 5 to 40 theoretical plates for concentration of the dialkyl carbonate.

Additionally preferably, the azeotrope composed of alcohol of reaction and dialkyl carbonate can also be separated by means of a hybrid process in the form of a combination of rectification and membrane separation (cf. FIG. 3). In this case, the distillate of $K_5$ is fed to a membrane separation M whose different embodiments have already been described above. In this case, a fraction 37 which is rich in alcohol of reaction and has an alcohol of reaction content of at least 70% by weight, preferably at least 90% by weight, based on the total weight of the fraction, is obtained on the permeate side and condensed in the condenser MPC. The retentate 35, which comprises a reduced alcohol of reaction content compared to the distillate of column $K_5$, is condensed in the condenser MRC and preferably fed back to the distillation column $K_5$ (36).

FIG. 7 shows, by way of example, a particularly preferred variant of the process according to the invention for purifying the bottom product which comprises diaryl carbonate and is obtained in the further reaction column(s) from step (b). The first diaryl carbonate distillation column $K_3$ of this preferred embodiment has four sectors, a lower stripping section ($K_3AT_2$) and an upper stripping section ($K_3AT_1$), and also a lower rectifying section ($K_3VT_2$) and an upper rectifying section ($K_3VT_1$). The bottom product of the second reaction column (8) is fed to the column between the lower rectifying section $K_3VT_2$ and upper stripping section $K_3AT_1$.

The first diaryl carbonate distillation column additionally has a one-stage or multistage (N-stage) top condenser $K_3C_{1-N}$ and a one-stage or multistage (N-stage) evaporator $K_3E_{1-N}$ for the bottom product. In the case of condensation or evaporation in a plurality of apparatuses (condensers and/or evaporators), both parallel and/or series connections and combinations of parallel and series connection are possible.

With regard to the condensation in the top condenser, different embodiments are conceivable. In addition to the embodiments of the integrated top condenser shown in FIGS. 5a and 5b, FIG. 13 shows a further preferred embodiment of a top condenser, which can likewise also be used in other process sections of the process according to the invention. In this case, the vapours (70) ascending out of the rectifying section are condensed in one or more additional column sector(s) ($K_NCS_{1-N}$) with a condensate cooled in an external circuit. The liquid leaving at the lower end of this column sector is partly withdrawn (71) and fed to one or more external cooler(s) $K_NW_{1-N}$, which may be connected either in series or in parallel, for removal of the heat of condensation obtained. The remaining liquid is either discharged as distillate (72) or introduced into the rectifying section $K_NVT$ as reflux (71). After the cooling, the liquid (75) is fed back to the distillation column above the additional column sector(s) $K_NCS_{1-N}$. In the condensation in the column, it is possible to use the column trays, random packings or structured packings already described above for. The uncondensed vapours or inerts (73) are withdrawn above the column sector(s) $K_NCS_{1-N}$.

The liquid 64 effluxing from the lower stripping section $K_3AT_2$ in the illustrative diagram in FIG. 7 is concentrated by evaporation in a one-stage or multistage (N-stage) evaporation, the vapours of the vapour/liquid mixture obtained being fed back to the lower stripping section $K_3AT_2$. The evaporation is effected preferably in a temperature range of 150 to 300° C., preferably of 160 to 240° C. and more preferably of 180 to 230° C. in the bottom of the column. The temperature at the top of the column is preferably 40 to 250° C., preferably 50 to 200° C. and more preferably 60 to 180° C. This affords a bottom product (55) with a residual content of diaryl carbonate of below 95% by weight, preferably below 90% by weight and more preferably below 75% by weight.

The purified diaryl carbonate is preferably withdrawn as a vaporous sidestream (57) above the lower stripping section $K_3AT_2$ and then condensed in a one-stage or multistage (N-stage) condenser $K_3 SC_{1-N}$ and removed as a liquid (51). The heat of condensation obtained in the condensation in the condenser(s) $K_3SC_{1-N}$ can preferably be used to raise steam or to heat other process sections, for example those in the preparation of diaryl carbonates.

The first diaryl carbonate distillation column $K_3$ is preferably operated at a top pressure of 1 to 1000 mbar (absolute), more preferably of 1 to 100 mbar (absolute) and most preferably of 5 to 50 mbar (absolute). The reflux ratio is preferably adjusted such that the diaryl carbonate content in the distillate 10 is preferably less than 10% by weight, more preferably less than 5% by weight and most preferably less than 1% by weight, based on the total weight of the distillate. To this end, preference is given to establishing a reflux ratio of 0.2 to 5, more preferably 0.2 to 2 and most preferably of 0.3 to 1.6.

If the crude diaryl carbonate comprises compounds having a boiling point between that of the diaryl carbonate and that of the alkyl aryl carbonate formed as a by-product during the preparation of the diaryl carbonate as an impurity, these may, in accordance with the invention, be withdrawn from the first distillation column in a further sidestream (53).

As shown in FIG. 7, the bottom product of the first diaryl carbonate distillation column (55), to prevent catalyst losses, can be recycled (52) to an extent of at least 50%, preferably at least 80% and more preferably at least 90% back into the transesterification of at least one dialkyl carbonate and at least one aromatic hydroxyl compound to prepare the diaryl carbonate. The remaining portion (55) of the bottom product is, in a particularly preferred embodiment, fed to one or more evaporator(s) $K_3E_{N+1}$ connected in series or parallel for the purpose of concentrating the residue and partly recovering the diaryl carbonate still present in the bottom product of the first diaryl carbonate distillation column. The diaryl carbonate (56) recovered in the residue concentration can be fed back to the first distillation column in liquid or vaporous form, preferably in vaporous form. The concentrated residue (54) can either be discharged from the process or fed to a further workup stage for the purpose of recovering the catalyst.

In the case of a discharge of the concentrated residue (54), the loss of diaryl carbonate is less than 5%, preferably less than 2%, more preferably less than 1% and most preferably less than 0.5%, based on the amounts of purified diaryl carbonate.

The above-described workup of the bottom product of the first diaryl carbonate distillation column can optionally also be carried out in all further embodiments presented hereinafter.

In a further particularly preferred embodiment of the process according to the invention, the diaryl carbonate (57) withdrawn in the sidestream of the first diaryl carbonate distillation column is purified in at least one, preferably in a second, diaryl carbonate distillation column. In a particularly preferred variant of this preferred embodiment, this second diaryl carbonate distillation column is configured without a stripping section. Such a particularly preferred variant of this preferred embodiment is shown by way of example in FIG. 4.

In this particularly preferred variant, the diaryl carbonate is purified in a first diaryl carbonate distillation column $K_3$—as has already been described by way of example in connection with FIG. 7—and an additional sidestream column $K_4$. The vaporous sidestream 57 is fed to the second diaryl carbonate distillation column $K_4$, preferably to the lower part thereof. Compared to the configuration in FIG. 7, the distillation column $K_3$ has an additional feed (61) above the lower stripping section $K_3AT_2$, through which the liquid bottom product from the column $K_4$ can be recycled back into $K_3$.

The column $K_4$ preferably has at least one sector. It is more preferably operated, as shown in FIG. 4, as a pure rectifying section $K_4VT_1$ and preferably possesses a separating performance of 1 to 50, more preferably of 2 to 30 and most preferably of 5 to 20 theoretical plates.

The second diaryl carbonate distillation column $K_4$ is operated at a top pressure of 1 to 1000 mbar (absolute), more preferably of 1 to 100 mbar (absolute) and most preferably of 5 to 50 mbar (absolute). The column $K_4$ is preferably operated at a reflux ratio of 0.1 to 10, more preferably of 0.2 to 5 and most preferably of 0.2 to 2.

The condensation of the vapours (62) at the top of the column $K_4$ can be effected in one or more stages in a top condenser $K_4C_{1-N}$. It is preferably effected in one or two stages in a temperature range of 70 to 250° C., more preferably of 90 to 230° C. and most preferably of 90 to 210° C. The waste heat obtained in the condensation can preferably be used to raise steam or to heat other process sections, for example those in the preparation of diaryl carbonates. The condensate obtained in the condensation is partly introduced back to the column $K_4$ as reflux (63). The remaining portion of the condensate is withdrawn as distillate (51) (purified diaryl carbonate). Inerts and/or uncondensed vapours (66) are discharged.

With regard to the condensation in the condenser $K_4C_{1-N}$, the same embodiments as already described for the condensation at the top of the first diaryl carbonate distillation column $K_3$ $K_3C_{1-N}$) are suitable.

A further particularly preferred embodiment of the purification of the bottom product which comprises diaryl carbonate and is obtained in the further reaction column(s) from step (b) is shown in FIG. 8. In the case of the particularly preferred variant that the second diaryl carbonate distillation column is configured without a stripping section, the rectifying section of this second diaryl carbonate distillation column may be integrated into the first diaryl carbonate distillation column ($K_3$). In this case, a portion of the vapours (57) coming from the lower stripping section of the first distillation column ($K_3AT_2$) passes into an integrated rectifying section ($K_4VT_1$), in order to reduce the content of very high boilers. The vapours (62) leaving at the top of this integrated sidestream column are condensed in the external condenser(s) $K_4C_{1-N}$ and partly recycled back to the top of the second diaryl carbonate distillation column as reflux (63). The remaining portion of the condensate is withdrawn as distillate (51) (purified diaryl carbonate). Uncondensed vapours (66) are discharged.

In a further particularly preferred variant of the particularly preferred embodiment of the process according to the invention using a second diaryl carbonate distillation column, this second diaryl carbonate distillation column is configured both with at least one rectifying section and with at least one stripping section. Such a particularly preferred variant of this preferred embodiment is shown by way of example in FIG. 9.

The second diaryl carbonate distillation column $K_4$ shown in FIG. 9 has both a stripping section $K_4AT_1$ and a rectifying section $K_4AT_2$. The vapour sidestream 57 of the first diaryl carbonate distillation column $K_3$ may first be condensed in a one-stage or multistage sidestream condenser $K_3SC_{1-N}$ and then fed to the column $K_4$. The second diaryl carbonate distillation column $K_4$ is preferably operated at a top pressure of 1 to 1000 mbar (absolute), preferably 1 to 100 mbar (absolute) and more preferably 5 to 50 mbar (absolute). This gives rise to a temperature in the bottom of 150 to 300° C., preferably of 160 to 240° C. and more preferably 180 to 230° C.

The second diaryl carbonate distillation column $K_4$ according to FIG. 9 has preferably an overall separating performance of 5 to 100 plates, preferably 10 to 80 plates, more preferably 30 to 80 plates, the rectifying section thereof having a separating performance of 1 to 99, preferably of 1 to 79 and more preferably of 2 to 79. The sidestream column $K_4$ is preferably operated at a reflux ratio of 0.5 to 20, preferably 1 to 10 and more preferably 1 to 5.

The condensation of the vapours (62) at the top of $K_4$ can be effected in one or more stages in a top condenser $K_4C_{1-N}$. It is preferably effected in one or two stages in a temperature range of 70 to 250° C., more preferably of 90 to 230° C. and most preferably of 90 to 210° C. The waste heat obtained in the condensation can preferably be used to raise steam or to heat other process sections, for example those in the preparation of diaryl carbonates. The condensate obtained in the condensation is partly introduced back to the second diaryl carbonate distillation column as reflux (63). The remaining portion of the condensate is withdrawn as distillate (51) (purified diaryl carbonate). Uncondensed vapours (66) are discharged.

The evaporation of the liquid effluxing from the stripping section $K_4AT_1$ of the second diaryl carbonate distillation column can likewise be effected in one or more stages in an evaporator $K_4E_{1-N}$.

The bottom product (67) of the second diaryl carbonate distillation column $K_4$ can subsequently be discharged fully or partly from the process and/or fed (61) fully or partly back to the first diaryl carbonate distillation column $K_3$.

The above-described particularly preferred embodiment of the process according to the invention using a second diaryl carbonate distillation column is suitable especially for the purification of diaryl carbonates with increased demands with regard to their quality. Such increased demands may lie, for example, in a reduced proportion of high-boiling secondary components, the proportion of which in the diaryl carbonate can be reduced by 10 to 100% by weight, preferably 20 to 90% by weight and more preferably 25 to 85% by weight compared to the process with only one distillation column.

In a further particularly preferred embodiment of the process according to the invention, the first diaryl carbonate distillation column can be configured as a dividing wall column.

Such an embodiment with a first diaryl carbonate distillation column as a dividing wall column with seven sectors is shown by way of example in FIG. 10. The dividing wall column $K_3$ in FIG. 10 has a stripping section $K_3AT_1$ in the lower part of the column $K_3$, in each case an upper sector $K_3TLO$ and a lower sector $K_3TLU$ on the feed side of the dividing wall T and an upper sector $K_3TRO$ and a lower sector $K_3TRU$ on the withdrawal side of the dividing wall T, and also an upper rectifying section $K_3VT_1$ and lower rectifying section $K_3VT_2$ in the upper part of the column. The crude diaryl carbonate (8) is fed to the column between the upper sector $K_3TLO$ and the lower sector $K_3TLU$ on the feed side of the dividing wall T; the purified diaryl carbonate (51) is withdrawn between the upper sector $K_3TRO$ and the lower sector $K_3TRU$ on the withdrawal side of the dividing wall T of the column.

The upper sector $K_3TLO$ present on the feed side of the dividing wall serves to remove high boilers present in the feed. The lower sector $K_3TLU$ on the feed side of the dividing wall serves to remove low boilers present in the crude diaryl carbonate or in the bottoms of the second reaction column (8). The upper sector $K_3TRO$ present on the withdrawal side of the dividing wall serves to remove low boilers present in the liquid stream (78) leaving the rectifying section $K_3VT_2$ in the upper part of the column. The lower sector of the withdrawal side $K_3TRU$ serves to remove high boilers present in the vapour stream (76) leaving the stripping section $K_3AT_1$.

The withdrawal of the purified diaryl carbonate on the withdrawal side of the dividing wall can be effected in liquid or vaporous form. In the column design, the method of removal may in some cases significantly influence the arrangement of the dividing wall within the column. The dividing wall may in each case be arranged within the column shifted to the withdrawal side or to the feed side, thus decreasing or increasing the cross section of the particular side compared to the other. In the case of vaporous withdrawal of the purified diaryl carbonate on the withdrawal side of the dividing wall, the cross section of the withdrawal side of the column is preferably greater than the cross section of the feed side, i.e. more vapour passes from the stripping section to the withdrawal side. In the case of liquid withdrawal of the purified diaryl carbonate on the withdrawal side of the dividing wall, the cross section of the feed side of the column is preferably identical to the cross section of the withdrawal side.

In the case of liquid withdrawal of the purified diaryl carbonate, which is shown by way of example in FIG. 10, 10 to 90%, preferably 20 to 90%, more preferably 50 to 85%, of the liquid effluxing from the stripping section $K_3TRO$ of the withdrawal side is withdrawn as sidestream 51. The remaining liquid is fed to the lower sector $K_3TRU$ of the withdrawal side. The liquid effluxing from the rectifying section $K_3VT_2$ is introduced (77) to an extent of 5 to 50%, preferably to an extent of 10 to 50% and more preferably 10 to 40%, to the feed side of the dividing wall, i.e. above $K_3TLO$. The remaining liquid is introduced (78) at the upper end of the withdrawal side of the dividing wall, i.e. to $K_3TRO$. The vapour ascending out of the stripping section $K_3AT_1$ is fed (69) to the feed side of the dividing wall to an extent of 5 to 90%, preferably to an extent of 10 to 80% and more preferably to an extent of 20 to 75%.

In the case of vaporous withdrawal of the purified diaryl carbonate, which is shown by way of example in FIG. 11, 10 to 90%, preferably 20 to 90%, more preferably 50 to 85%, of the vapour leaving the lower sector $K_3TRU$ of the withdrawal side is withdrawn as a sidestream (57). The remaining vapour is fed to the upper sector $K_3TRO$ of the withdrawal side. The liquid effluxing from the rectifying section $K_3VT_2$ is introduced (77) to an extent of 5 to 90%, preferably to an extent of 10 to 80% and more preferably 20 to 60% to the feed side of the dividing wall, i.e. above $K_3TLO$. The remaining liquid is introduced (78) at the upper end of the withdrawal side of the dividing wall, i.e. to $K_3TRO$. The vapour ascending out of the stripping section $K_3AT_1$ is fed (69) to the feed side of the dividing wall to an extent of 5 to 90%, preferably to an extent of 10 to 80% and more preferably to an extent of 20 to 60%. In the case of vaporous withdrawal, the sidestream (57) withdrawn in vaporous form is preferably condensed in one or more sidestream condenser(s) $K_3SC_{1-N}$ and removed as a liquid diaryl carbonate stream (51).

The upper rectifying section of such a dividing wall column preferably has a separation performance of 0 to 40, more preferably 1 to 20 and most preferably 1 to 10 theoretical plates, the lower rectifying section of preferably 1 to 40, more preferably 5 to 20 and most preferably 5 to 15 theoretical plates, the stripping section of preferably 1 to 40, more preferably 2 to 20 and most preferably 2 to 15 theoretical plates. The upper sector $K_3TLO$ and lower sector $K_3TLU$ on the feed side of the dividing wall and the upper sector $K_3TRO$ and lower sector $K_3TRU$ on the withdrawal side of the dividing wall preferably each have a separation performance of 1 to 40, more preferably 2 to 20 and most preferably 5 to 20 theoretical plates.

The dividing wall column additionally comprises a one- or multistage (N-stage) top condenser $K_3C_{1-N}$ and a one-stage or multistage (N-stage) evaporator $K_3E_{1-N}$ for the bottom product.

The condensation of the vapours at the top of the dividing wall column can be effected in one or more stages, preferably one or two stages, in a temperature range of 40 to 250° C., preferably of 50 to 200° C. and more preferably of 60 to 180° C. With regard to the condensation in the top condenser, the different embodiments of the condensers already specified above for the distillation columns are possible.

The liquid (64) effluxing from the stripping section $K_3AT_1$ is concentrated by evaporation in a one-stage or multistage (N-stage) evaporation, the vapours of the vapour/liquid mixture obtained being fed back to the lower stripping section $K_3AT_1$. The evaporation is effected preferably within a temperature range of 100 to 250° C., preferably of 150 to 240° C. and more preferably of 180 to 220° C.

The dividing wall column is operated at a top pressure of 1 to 1000 mbar (absolute), more preferably of 1 to 100 mbar (absolute) and most preferably of 5 to 50 mbar (absolute). The reflux ratio is adjusted such that the diaryl carbonate content in the distillate 10 is preferably less than 10% by weight, more preferably less than 5% by weight and most preferably less than 1% by weight, based on the total weight of the distillate.

For this purpose, preference is given to establishing a reflux ratio of 0.2 to 5, more preferably 0.2 to 2 and most preferably of 0.3 to 1.6, the reflux ratio in the context of the invention corresponding to the weight ratio of condensate recycled into the column to vapour withdrawn at the top of the column without recycled condensate.

If the diaryl carbonate to be purified comprises compounds having a boiling point between that of the diaryl carbonate and that of the alkyl aryl carbonate formed as an intermediate during the preparation of the diaryl carbonate as an impurity, they may, in accordance with the invention, be withdrawn from the dividing wall column in a further sidestream (53).

In a preferred embodiment of the process according to the invention, the removal of medium-boiling secondary compounds is effected in two distillation columns. Such a preferred embodiment is shown in FIG. 6.

The first intermediate boiler column shown in FIG. 6 (alkyl aryl ether preconcentration column) $K_7$ has a stripping section $K_7AT$ with 5 to 40 theoretical plates, and also a rectifying section $K_7VT$ with 5 to 40 theoretical plates. The stream 8 which is preferably supplied in liquid form from the second reaction column $K_2$ (38) is fed to column $K_7$ above the stripping section. The first intermediate boiler column $K_7$ is preferably operated at a top pressure of 50 to 3000 mbar (absolute), preferably 100 to 2000 mbar (absolute) and more preferably 500 to 1500 mbar (absolute).

The first intermediate boiler column $K_7$ is additionally preferably operated at a reflux ratio of 0.1 to 10, preferably 0.5 to 5 and more preferably 0.5 to 2.

The condensation of the vapours (44) at the top of $K_7$ can be effected in one or more stages in a top condenser $K_7C_{1-N}$. The condensate obtained in the condensation is partly introduced back to the first intermediate boiler column $K_7$ as reflux (45). The remaining portion of the condensate is withdrawn as distillate (5), comprising alcohol of reaction and dialkyl carbonate. Uncondensed vapours (46) are discharged.

The evaporation of the liquid effluxing from the stripping section $K_7AT$ of the first intermediate boiler column $K_7$ can be effected in one or more stages in an evaporator $K_7E_{1-N}$.

The bottom product (43) of the first intermediate boiler column $K_7$, comprising aromatic hydroxyl compound and medium-boiling secondary compounds, is, in the case of the particular embodiment shown in FIG. 6, fed to a second intermediate boiler column $K_8$ (alkyl aryl ether column).

The second intermediate boiler column $K_8$ has a stripping section with two sectors ($K_8AT_1$ and $K_8AT_2$), each of which has a separating performance of 5 to 40 theoretical plates, and also a rectifying section $K_8VT$ with 5 to 40 theoretical plates. The bottom product of the first intermediate boiler column $K_7$ is fed to the second intermediate boiler column $K_8$ above the upper stripping section $K_8AT_1$. The second intermediate boiler column $K_8$ is preferably operated at a top pressure of 50 to 3000 mbar (absolute), preferably 100 to 2000 mbar (absolute) and more preferably 500 to 1500 mbar (absolute).

The second intermediate boiler column $K_8$ is additionally preferably operated at a reflux ratio of 1 to 1000, preferably 10 to 500 and more preferably 50 to 200.

The condensation of the vapours (47) at the top of $K_8$ can be effected in one or more stages in a top condenser $K_8C_{1-N}$. The condensate obtained in the condensation is partly introduced back to the second intermediate boiler column $K_8$ as reflux (48). The remaining portion of the condensate is withdrawn as distillate (40) comprising medium-boiling secondary compounds with a boiling point below that of the aromatic hydroxyl compound. Uncondensed vapours (49) are discharged.

The evaporation of the liquid effluxing from the stripping section $K_8AT$ of the second intermediate boiler column $K_8$ can be effected in one or more stages in an evaporator $K_8E_{1-N}$.

The bottom product (65) of the second intermediate boiler column $K_8$, comprising aromatic medium-boiling secondary compounds and alkyl aryl carbonate, is, according to the content of medium-boiling secondary compounds having a boiling point above that of the aromatic hydroxyl compounds, discharged (41) from the process or recycled again (42).

The aromatic hydroxyl compound is preferably withdrawn as a sidestream, more preferably as a vaporous sidestream above the lower stripping section $K_8AT_2$. In the case of vaporous sidestream withdrawal, the stream (68) is condensed in the condenser $K_8SC_{1-N}$ and fed (39) back to the reaction in the first reaction column. The heat of condensation obtained in the condensation of the vaporous sidestream (68) can be used to generate a heat carrier or for energy integration in the process.

In a further preferred embodiment, the removal of medium-boiling secondary compounds can be effected in two distillation columns, in which case the second intermediate boiler column is configured as a dividing wall column. Such a particular embodiment is shown in FIG. 12.

In this case, the sidestream (68) is withdrawn in vaporous or liquid form, more preferably in vaporous form.

The dividing wall column $K_8$ preferably has at least six sectors, a stripping section $K_8AT$ in the lower part of column $K_8$, in each case an upper sector $K_8TLO$ and lower sector $K_8TLU$ on the feed side of the dividing wall T and an upper sector $K_8TRO$ and lower sector $K_8TRU$ on the withdrawal side of the dividing wall T, and also a rectifying section $K_8VT$ in the upper part of the column with in each case 5 to 40 theoretical plates.

The explanations for the first intermediate boiler column $K_7$ and regarding the further streams and condensers and evaporators of the second intermediate boiler column $K_8$ according to the preferred embodiment shown in FIG. 6 apply analogously to the preferred embodiment according to FIG. 12.

The example which follows serves to illustrate the invention by way of example and should not be interpreted as a restriction.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Example 1

Inventive

For the example, an overall construction as shown in FIG. 14 can be used.

399.3 kg/h of a mixture (18) of 85.4% by weight of phenol, 9.2% by weight of dimethyl carbonate, 3.2% by weight of diphenyl carbonate, 1.5% by weight of titanium tetraphenoxide, 0.3% by weight of anisole, 0.3% by weight of methyl phenyl carbonate and 0.1% by weight of methanol are metered into the upper end of the reaction zone of a first reaction column ($K_1$) comprising an upper rectifying section ($K_1VT_2$) with 4 theoretical plates, an intermediate condenser ($K_1IC_1$), a lower rectifying section ($K_1VT_1$) with 4 theoretical plates, a reaction zone ($K_1RZ$) with 30 reaction trays (holdup: 12 l), 3 trays being equipped with heating elements ($K_1E\_RZ_{1-3}$), and a stripping section $K_1AT$ with 6 trays (holdup: 12 l). At the lower end of the reaction zone ($K_1RZ$), 539.6 kg/h of a vapour mixture (17), superheated by 5° C., of 98.8% by weight of dimethyl carbonate, 0.9% by weight of phenol, 0.2% by weight of anisole and 0.1% by weight of methanol are fed in.

This affords, at the bottom of the column, 452.4 kg/h of a product mixture (6) of 49.8% by weight of phenol, 28.2% by weight of methylphenylcarbonate, 12.3% by weight of diphenylcarbonate, 8.1% by weight of dimethylcarbonate, 0.2% by weight of anisole and 1.4% by weight of titanium tetraphenoxide.

$K_1$ is operated at a top pressure (above $K_1VT_2$) of 3.6 bar and a reflux ratio of 1.15. A temperature 230° C. is established in the bottom of the column and, in the reaction zone ($K_1RZ$), a mean reaction temperature of 215° C. A bottom evaporator $K_1E_1$ and three intermediate evaporators ($K_1E\_RZ_{1-3}$) in the reaction zone are operated with steam at a vapour pressure of 35 bar, the bottom evaporator ($K_1E_1$) used being a natural circulation evaporator, and heating registers integrated onto the reaction trays being used as intermediate evaporators. The entrance temperature into the intermediate condenser (above $K_1IC_1$) is 205° C., the exit temperature 193° C. and the cooling output 57 kW. The heat of condensation obtained in the intermediate condensation can be used to raise steam with a steam pressure of 8 bar (dew temperature: 170.4° C.). The heating output required to evaporate the dimethyl carbonate-comprising stream (15) is 52 kW. The evaporation and overheating of the dimethyl carbonate are effected at a temperature of 135 to 152° C., for which the vapour used in the intermediate condenser can be used without any problem.

The bottom product (6) of the first reaction column ($K_1$) is fed to a second reaction column ($K_2$) comprising a rectifying section ($K_2VT$) with 10 theoretical plates and a stripping section ($K_2AT$) with 22 theoretical plates.

In addition, 81.9 kg/h of a mixture (9) of 69.9% by weight of methyl phenyl carbonate, 28.3% by weight of phenol, 1.2% by weight of dimethyl carbonate, 0.5% by weight of diphenyl ether and 0.1% by weight of diphenyl carbonate from the diphenyl carbonate fine distillation ($K_3$) are metered in the region of the stripping section ($K_2AT$).

This affords, at the bottom of the second reaction column ($K_2$) 236.6 kg/h of a product mixture (8) of 62.8% by weight of diphenyl carbonate, 24.2% by weight of methyl phenyl carbonate, 9.8% by weight of phenol, 0.4% by weight of dimethylcarbonate, 2.6% by weight of titanium tetraphenoxide and 0.2% by weight of diphenyl ether.

Additionally withdrawn are 238.2 kg/h of liquid distillate (3) comprising 83.5% by weight of phenol, 15.5% by weight of dimethyl carbonate, 0.6% by weight of methyl phenyl carbonate, 0.3% by weight of anisole and 0.1% by weight of methanol.

The vapour mixture coming from the second reaction column ($K_2$) is only partly condensed, and so 60 kg/h of a vaporous product stream (7) are also withdrawn after the condensation ($K_2C_{1-3}$), for the purpose of discharging medium-boiling secondary compounds, especially anisole. This vaporous product stream comprises 59.8% by weight of dimethyl carbonate, 38.2% by weight of phenol, 1.6% by weight of methanol, 0.3% by weight of anisole and 0.1% by weight of methyl phenyl carbonate.

The second reaction column ($K_2$) is operated at a top pressure (above $K_2VT$) of 1 bar and a reflux ratio of 0.65. As a result of the use of structured packings in the rectifying and stripping sections, the pressure drop in the column is less than 50 mbar. The mixture effluxing from stripping section ($K_2AT$) has a temperature of 198° C. and is fed in a two-stage evaporation. The exit temperature downstream of the first evaporation stage ($K_2E_1$) is 209° C. and, downstream of the second evaporator stage ($K_2E_2$), 230° C. The evaporators used are a natural circulation evaporator in the first stage and a kettle-type evaporator in the second stage. The total evaporator output is 66.4 kW. Since the catalyst is nonvolatile, the reaction is limited to the stripping section, the column bottom and the evaporators. Owing to the comparatively low temperatures in the stripping section (188-198° C.), the reaction takes place predominantly in the column bottom and the evaporators.

The condensation of the vapour mixture (27) withdrawn at the top of the second reaction column is effected in 3 stages, specifically at 174-165° C. (45 kW) in the 1st stage, at 165-155° C. (17 kW) in the 2nd stage, and at 155154° C. (1 kW) in the 3rd stage. The heat of condensation of the 1st and 2nd stages is used to separate a mixture of dimethyl carbonate and methanol.

The distillate (4) of the first reaction column $K_1$ with a total amount of 486.6 kg/h comprises 90.6% by weight of dimethyl carbonate, 8.2% by weight of methanol, 1% by weight of phenol and 0.2% by weight of anisole, and is fed together with 36.6 kg/h of a further stream (5) comprising 97.3% by weight of dimethyl carbonate and 2.7% by weight of methanol to a processing step in two distillation columns $K_5$ and $K_5$ for the purpose of removing the methanol and recovering the dimethyl carbonate.

This affords 482 kg/h of a dimethyl carbonate fraction (11) containing 98.75% by weight of dimethyl carbonate, 1% by weight of phenol, 0.2% by weight of anisole and 0.05% by weight of methanol, and 41 kg/h of a methanol fraction (10) containing 99.5% by weight of methanol and 0.5% by weight of dimethyl carbonate.

Since methanol and dimethyl carbonate form an azeotrope, the separation of the mixture is carried out employing the two-pressure process. In this case, the mixture is first heated to 137° C. in a preheater and also partly evaporated at the same time, then separated in a dimethyl carbonate distillation column $K_5$ first into the aforementioned dimethyl carbonate fraction as the bottom product (11) and 113.4 kg/h of a fraction with virtually azeotropic composition (13) containing 76.1% by weight of methanol and 23.9% by weight of dimethyl carbonate as a distillate.

The dimethyl carbonate distillation column ($K_5$) works at a top pressure of 5.5 bar and a reflux ratio of 1.2 and has a rectifying section ($K_5VT$) with 16 theoretical plates and a stripping section ($K_5AT$) with 7 theoretical plates.

This gives rise to a temperature in the bottom of the column of 155.8° C. The heat of evaporation required is 58.2 kW. The bottom product is evaporated in two natural circulation evaporators ($K_5E_{1-2}$), the majority of the heat (45 kW) being exchanged in a circulation evaporator which simultaneously functions as the first condenser of the second reaction column. The remaining heat of evaporation is provided in a second circulation evaporator by means of steam.

The heat exchanger for heating the feed stream of the dimethyl carbonate distillation column ($K_5W_1$) functions simultaneously as a second condenser of the second reaction column, the amount of heat transferred being 17 kW.

In a methanol distillation column ($K_6$) which works at a top pressure of 600 mbar and a reflux ratio of 2.3, methanol is removed as the bottom product (41 kg/h; methanol/dimethylcarbonate 99.5/0.5% by weight). The distillate (12) with a total amount of 72.3 kg/h, 62.4% by weight of methanol and 37.6% by weight of dimethyl carbonate, is fed back to the dimethyl carbonate distillation column.

The methanol distillation column ($K_6$) has a separating performance of 30 theoretical plates, which are divided equally between the rectifying section and stripping section.

The heat required in the evaporator of the methanol distillation column (56 kW) is provided by the condensation of the vapours from the dimethyl carbonate distillation column. The condenser of the dimethyl carbonate distillation column thus functions simultaneously as the evaporator of the methanol distillation column.

The bottoms mixture (6) obtained in the second reaction column ($K_2$) containing 62.7/24.2/9.8/0.4/2.6/0.03% by weight of diphenylcarbonate/methylphenylcarbonate/phenol/dimethylcarbonate/titanium tetraphenolate/salol and a total amount of 236.6 kg/h is fed to a distillative workup for the purpose of isolating the diphenyl carbonate, removing very high boilers and catalyst and low-boiling compounds. This consists of a diphenyl carbonate fine distillation column $K_3$ and a diphenyl carbonate sidestream column $K_4$ worked up according to FIG. 4.

The diphenyl carbonate fine distillation column ($K_3$) consists of four sectors, an upper rectifying section ($K_3VT_1$) with 5 theoretical plates, a lower rectifying section ($K_3VT_2$) with 3 theoretical plates, an upper stripping section ($K_3AT_1$) with 16 theoretical plates and a lower stripping section ($K_3AT_2$) with 9 theoretical plates. The condensation of the vapours leaving at the top of the column in the top condenser ($K_3C_1$) and the partial evaporation of the liquid effluxing from the lower stripping section ($K_3AT_2$) in the evaporator ($K_3E_1$) for the bottom product are each effected in one stage.

The diphenyl carbonate fine distillation column ($K_3$) is operated at a top pressure of 15 mbar and a reflux ratio of 0.7.

This affords, as the distillate (9), a stream containing 69.9/28.3/1.2/0.5% by weight of methylphenylcarbonate/phenol/dimethylcarbonate/DPE. Below the upper rectifying section ($K_3VT_1$), 0.02 kg/h of liquid is withdrawn for the purpose of discharge of intermediate boilers in the sidestream (53). In addition, below the upper rectifying section ($K_3VT_1$), 201 kg/h of a vaporous sidestream (57) containing 99.9% by weight of diphenylcarbonate are withdrawn. The bottom product (55) obtained is 20.6 kg/h of a mixture containing 70/29.8/0.2% by weight of diphenylcarbonate/titanium tetraphenolate/salol.

The vaporous sidestream (57) is fed to a sidestream column ($K_4$). This possesses only a rectifying section ($K_4VT$) with 9 theoretical plates.

The sidestream column ($K_4$) is operated under identical pressure conditions to the diphenylcarbonate fine distillation column ($K_3$) and at a reflux ratio of 0.5.

The vapours (62) leaving at the top of the sidestream column ($K_4$) are condensed in a two-stage condensation in the condensers ($K_4C_{1-2}$), the heat of condensation being used either to raise steam or to heat other process sections of the diphenylcarbonate preparation.

This affords a distillate (51) containing 99.96% by weight of diphenylcarbonate and only 300 ppm of salol. The liquid (61) effluxing at the bottom of the sidestream column is fed to the diphenyl carbonate fine distillation column ($K_3$) above the lower stripping section ($K_3AT_2$).

The vapour mixture remaining after the condensation of the second reaction column ($K_2C_{1-3}$) is optionally first condensed ($K_2C_4$) and then sent to a further workup to remove medium-boiling secondary compounds, especially anisole.

The workup is effected in two distillation columns. In an anisole preconcentration column ($K_7$), a low boiler fraction is withdrawn as the top product. This comprises 97.3% by weight of dialkyl carbonate and 2.7% by weight of alcohol of reaction, and has a total amount of 36.6 kg/h. The bottom product withdrawn is 23 kg/h of a mixture comprising and 99.0/0.1/0.65% by weight of phenol/dimethylcarbonate/anisole.

The anisole preconcentration column ($K_7$) has a rectifying section ($K_7VT$) with 8 theoretical plates and a stripping section ($K_7AT$) with 14 theoretical plates. The condensation ($K_7C_1$) of the vapours (44) withdrawn at the top of the column is effected in one stage at a condensation temperature of 88 to 80° C. The column is operated at a top pressure of 1 bar and a reflux ratio of 0.8. The energy is supplied in the bottom of the column by means of natural circulation evaporators ($K_7E_1$).

The bottom product (43) of the anisole preconcentration column ($K_7$) is fed to the anisole column ($K_8$). The distillate withdrawn from the anisole removal (5) is 0.2 kg/h of a mixture of 46.4/41.3/9.8/2.5% by weight of phenol/anisole/dimethylcarbonate/other medium-boiling secondary compounds. The sidestream withdrawal (68) is effected in vaporous form. The vapour stream withdrawn comprises phenol with a purity of 99.7% by weight. This is condensed and fed back to the first reaction column ($K_1$), after mixing with further streams comprising the phenol and optionally the catalyst. The heat of condensation obtained in the condensation ($K_8SC_1$) is used to raise steam with a steam pressure of 7 bar absolute.

In the bottom of the anisole removal, 0.1 kg/h (41) is withdrawn and discharged completely from the process.

The anisole column ($K_8$) has a rectifying section ($K_8VT$) with 14 theoretical plates and a stripping section ($K_8AT$) with 14 theoretical plates, the stripping section consisting of an upper stripping section ($K_8AT_1$) with 10 theoretical plates and a lower stripping section ($K_8AT_2$) with 4 theoretical plates. The sidestream is withdrawn above the lower stripping section ($K_8AT_2$). The condensation ($K_8C_1$) of the vapours (47) withdrawn at the top of the column is effected in one stage. The column is operated under reflux conditions at a reflux ratio of 84. The energy is supplied in the bottom of the column by means of a falling-film evaporator ($K_8E_1$). The top pressure of the column is 1 bar absolute.

The example shows in an impressive manner how the energy consumption in the preparation of diphenyl carbonate can be reduced significantly by efficient thermal integration.

For instance, in the first reaction column the use of an intermediate condenser allows the heat demand including the heating and evaporation of the reactants, evaporation in the bottom of the column and heating of the reaction zone to be reduced from 183.3 to 131.3 kW, i.e. by 28.4%. At the same time, the coolant consumption is reduced from 183.2 to 126.2 kW, i.e. by 31.1%.

The thermal integration of the second reaction column with the separation of the methanol/dimethyl carbonate mixture allows the heating medium requirement for separation of methanol and dimethyl carbonate to be reduced from 76 kW to 13 kW, i.e. by 83%. At the same times the coolant requirement of the second reaction column is reduced from 64 to 1 kW, i.e. by 98.4%.

The invention claimed is:

1. A process for preparing a diaryl carbonate from a dialkyl carbonate and an aromatic hydroxyl compound comprising the steps of:

(a) reacting a dialkyl carbonate with an aromatic hydroxyl compound in the presence of a transesterification catalyst in a first reaction column, wherein said first reaction column comprises a rectifying section in the upper part of said first reaction column column and a reaction zone below said rectifying section, wherein said reaction zone comprises at least two sectors;

(h) feeding bottom product produced in said first reaction column in step (a) to a further reaction column, wherein said further reaction column comprises a rectifying section in the upper part of said further reaction column and a reaction zone below said rectifying section, and further reacting said bottom product in said reaction zone;

(c) separating at least a portion of unconverted dialkyl carbonate formed during the reaction in the reaction columns of steps (a) and/or (b) from alkyl alcohol formed during the reaction in at least one distillation column;

(d) feeding at least a portion of vapor comprising said aromatic hydroxyl compound withdrawn from the top of said further reaction column in step (b), optionally after condensing said vapor in a condenser, to a distillation column to remove one or more compounds having a boiling point between that of said dialkyl carbonate and that of alkyl aryl carbonate formed during the preparation of said diaryl carbonate; and (e) feeding bottom product produced in said further reaction column in step (b), wherein said bottom product comprises diaryl carbonate, to a distillation column for purification, wherein said distillation column comprises a rectifying section in the upper part of said distillation column and a stripping section in the lower part of said distillation column;

wherein at least one of said first reaction column and said further reaction column is equipped with a condenser and the heat of condensation obtained by condensation in said condenser is directly or indirectly recycled back into said process;

wherein the evaporation temperature in the bottom of the at least one distillation column used in step (c) is below the condensation temperature in the condenser, and wherein the at least one distillation column used in step (c) can be operated fully or partly with the heat of condensation in the condenser;

wherein the diaryl carbonate-is a diaryl carbonate of formula (I)

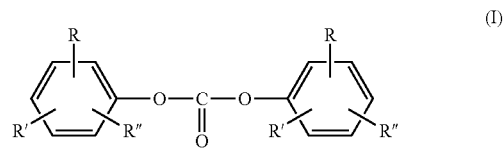

wherein R, R' and R" represent, independent of one another, H, linear or branched, optionally substituted $C_1$-$C_{34}$-alkyl, $C_1$-$C_{34}$-alkoxy, $C_5$-$C_{34}$-cycloalkyl, $C_7$-$C_{34}$-alkylaryl, $C_6$-$C_{34}$-aryl or a halogen radical, R may also represent —COO—R''' where R''' represents H, branched or unbranched $C_1$-$C_{34}$-alkyl, $C_1$-$C_{34}$-alkoxy, $C_5$-$C_{34}$-cycloalkyl, $C_7$-$C_{34}$-alkylaryl or $C_6$-$C_{34}$-aryl;

wherein the dialkyl carbonate is a dialkyl carbonate of formula (II)

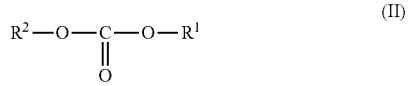

wherein $R^1$ and $R^2$ represent, independently of one another, a linear or branched, optionally substituted $C_1$-$C_{34}$-alkyl;

wherein the aromatic hydroxyl compound is an aromatic hydroxyl compound of formula (III)

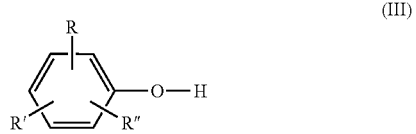

wherein R, R' and R" represent, independent of one another, H, linear or branched, optionally substituted $C_1$-$C_{34}$-alkyl, $C_1$-$C_{34}$-alkoxy, $C_5$-$C_{34}$-cycloalkyl, $C_7$-$C_{34}$-alkylaryl, $C_6$-$C_{34}$-aryl or a halogen radical, R may also represent —COO—R'" where R'" represents H, branched or unbranched $C_1$-$C_{34}$-alkyl, $C_1$-$C_{34}$-alkoxy, $C_5$-$C_{34}$-cycloalkyl, $C_7$-$C_{34}$-alkylaryl or $C_6$-$C_{34}$-aryl.

2. The process of claim 1, wherein said rectifying section of said first reaction column comprises an intermediate condenser and heat of condensation Obtained by condensation in said intermediate condenser is directly or indirectly recycled back into said process.

3. The process of claim 2, wherein at least a portion of said heat of condensation is directly or indirectly used to separate said dialkyl carbonate from said alkyl alcohol in step (c) and/or to evaporate said dialkyl carbonate fed into said first reaction column in step (a).

4. The process of claim 3, wherein said heat of condensation is directly or indirectly used to separate said dialkyl carbonate from said alkyl alcohol in step (c) and to evaporate said dialkyl carbonate fed into said first reaction column in step (a).

5. The process of claim 2, wherein said further reaction column comprises a condenser at the top of said further reaction column and heat of condensation obtained by condensation in said condenser is directly or indirectly recycled back into said process.

6. The process of claim 5, wherein said heat of condensation is directly or indirectly used to separate said dialkyl carbonate from said alkyl alcohol in step (c) and/or to evaporate said dialkyl carbonate fed into said first reaction column in step (a).

7. The process of claim 6, wherein said heat of condensation is directly or indirectly used to separate said dialkyl carbonate from said alkyl alcohol in step (c) and to evaporate said dialkyl carbonate fed into said first reaction column in step (a).

8. The process of claim 5, wherein at least a portion of said heat of condensation obtained by condensation in said condenser at the top of said further reaction column is used to separate said dialkyl carbonate from said alkyl alcohol in step (c) and at least a portion of said heat of condensation obtained by condensation in said intermediate condenser is directly or indirectly used to evaporate said dialkyl carbonate fed into said first reaction column in step (a).

9. The process of claim 1, wherein said further reaction column comprises a condenser at the top of said further reaction column and heat of condensation obtained by condensation in said condenser is directly or indirectly: recycled back into said process.

10. The process of claim 5, wherein said heat of condensation is directly or indirectly used to separate said dialkyl carbonate from said alkyl alcohol in step (c) and/or to evaporate said dialkyl carbonate fed into said first reaction column in step (a).

11. The process of claim 10, wherein said heat of condensation is directly or indirectly used to separate said dialkyl carbonate from said alkyl alcohol in step (c) and to evaporate said dialkyl carbonate fed into said first reaction column in step (a).

12. The process of claim 1, wherein said bottom product produced in said further reaction column in step (b) comprises said transesterification catalyst.

13. The process of claim 1, wherein said bottom product produced in said further reaction column in step (b) is fed to a distillation column for purification, wherein a diaryl carbonate-containing sidestream is withdrawn from said distillation column.

14. The process of claim 13, wherein said bottom product produced in said further reaction column in step (b) comprises a compound having a boiling point between that of said diaryl carbonate and that of alkyl aryl carbonate formed as a by-product during the preparation of said diaryl carbonate as an impurity, wherein said compound is withdrawn from said distillation column in a further sidestream and optionally recycled into said first reaction column of step (a) or said further reaction column of step (b).

15. The process of claim 13, wherein said distillation column is a dividing wall column.

16. The process of claim 1, wherein said dialkyl carbonate removed in step (c) is fed back to said first reaction column in step (a) optionally after further purification.

17. The process of claim 1, wherein said one or more compounds having a boiling point between that of said dialkyl carbonate and that of alkyl aryl carbonate formed during the preparation of said diaryl carbonate is said aromatic hydroxyl compound of said vapor and wherein said aromatic hydroxyl compound is fed to said first reaction column in step (a).

18. The process of claim 17, wherein said aromatic hydroxyl compound is withdrawn from a first and only distillation column as a bottom product or from a second or further distillation column as a sidestream.

19. The process of claim 17, wherein product withdrawn from the top of said first distillation column comprises dialkyl carbonate, wherein at least a portion of said product is fed to said distillation column in step (c).

20. The process of claim 1, wherein said vapour comprising said aromatic hydroxyl compound is fed to a first distillation column and at least one further distillation column, wherein the bottom product produced in said first distillation column is fed to a second distillation column.

21. The process of claim 1, wherein at least one of said reaction columns and/or at least one of said distillation columns used in said process comprises a top condenser integrated into said reaction column and/or distillation column, wherein the d/D ratio of the diameter of the vapour line from reaction column and/or distillation column to top condenser is in the range of from 0.2 to 1.

22. The process of claim 1, wherein lines and units which conduct mixtures having a melting point of more than 30° C. are heated to temperatures above this melting point.

23. The process of claim 1, wherein lines and units which conduct mixtures having a melting point of more than 40° C. are heated to temperatures above this melting point.

24. The process of claim 1, wherein
   a. at least a portion of a catalyst-containing stream is obtained from the bottom product produced in said distillation column of step (e) and is recycled, optionally after further purification, back into said process, preferably into process step (a),
   b. at least a portion of a stream comprising an aromatic hydroxyl compound and an alkyl aryl carbonate obtained from said distillation column of step (e) is recycled back into said process, and
   c. at least a portion of one or more compounds having a boiling point above the boiling point of said diaryl carbonate and at least a portion of one or more compounds whose boiling point is between that of said dialkyl carbonate and that of alkyl aryl carbonate formed during the preparation of said diaryl carbonate are discharged from said process, together or separately from one another, from said distillation column of step (e).

25. The process of claim 24, wherein at least a portion of said catalyst-containing stream obtained from the bottom product produced in said distillation column of step (e) is recycled, optionally after further purification, back into process step (a).

26. The process of claim 24, wherein at least a portion of said stream comprising an aromatic hydroxyl compound and an alkyl aryl carbonate obtained from said distillation column of step (e) is recycled back into process step (a) or (b).

27. The process of claim 1, wherein the bottom product produced in said first reaction column in step (a) is fed directly to a further reaction column.

* * * * *